US007037680B2

(12) United States Patent
Smith et al.

(10) Patent No.: US 7,037,680 B2
(45) Date of Patent: May 2, 2006

(54) **RECOMBINANT LIGHT CHAINS OF *BOTULINUM* NEUROTOXINS AND LIGHT CHAIN FUSION PROTEINS FOR USE IN RESEARCH AND CLINICAL THERAPY**

(75) Inventors: Leonard A. Smith, Clarksburg, MD (US); Melody Jensen, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 444 days.

(21) Appl. No.: 10/011,588

(22) Filed: Nov. 6, 2001

(65) Prior Publication Data

US 2002/0168727 A1 Nov. 14, 2002

Related U.S. Application Data

(63) Continuation-in-part of application No. 09/910,186, filed on Jul. 20, 2001, which is a continuation of application No. 09/611,419, filed on Jul. 6, 2000, which is a continuation of application No. 08/123,975, filed on Sep. 21, 1993, now abandoned, application No. 09/611,419.

(60) Provisional application No. 60/311,966, filed on Aug. 6, 2001, provisional application No. 60/246,774, filed on Nov. 6, 2000, provisional application No. 60/133,866, filed on May 12, 1999, provisional application No. 60/133,868, filed on May 12, 1999, provisional application No. 60/133,869, filed on May 12, 1999, provisional application No. 60/133,865, filed on May 12, 1999, provisional application No. 60/133,873, filed on May 12, 1999, provisional application No. 60/133,867, filed on May 12, 1999.

(51) Int. Cl.
*C12P 21/06* (2006.01)
*C12P 21/04* (2006.01)
*C12N 15/09* (2006.01)
*C12N 1/12* (2006.01)
*C12N 1/20* (2006.01)

(52) U.S. Cl. ............... 435/69.1; 435/69.7; 435/69.3; 435/70.1; 435/71.1; 435/71.2; 435/842; 435/252.3; 435/252.33; 435/254.23; 435/252.1; 435/320.1; 536/23.1; 536/23.4; 536/23.7; 536/24.1

(58) Field of Classification Search ............... 435/69.1, 435/69.3, 320.1, 235.1, 325, 172.3, 69.7, 435/70.1, 71.1, 71.2, 842, 252.1, 252.3, 252.33, 435/254.23; 536/23.1, 23.6, 23.4, 23.7, 24.1
See application file for complete search history.

(56) References Cited

U.S. PATENT DOCUMENTS 5,196,193 A 3/1993 Carroll
5,601,823 A * 2/1997 Williams et al. ......... 424/167.1
5,919,665 A 7/1999 Williams
5,939,070 A * 8/1999 Johnson et al. ......... 424/194.1
6,365,158 B1 * 4/2002 Williams et al. ......... 424/190.1
6,444,209 B1 * 9/2002 Johnson et al. ......... 424/194.1
6,461,617 B1 * 10/2002 Shone et al. ............. 424/236.1
6,495,143 B1 * 12/2002 Lee et al. ................ 424/199.1
6,573,003 B1 * 6/2003 Williams et al. ......... 424/190.1
6,613,329 B1 * 9/2003 Kink et al. ............... 424/164.1
6,670,148 B1 * 12/2003 Mundschenk et al. ..... 435/69.1
6,737,251 B1 * 5/2004 Marchetti et al. .......... 435/69.1
6,822,075 B1 * 11/2004 Bjorck et al. ............... 530/350
2003/0219457 A1 * 11/2003 Williams .................. 424/199.1
2005/0143289 A1 * 6/2005 Hunt ............................ 514/2
2005/0169442 A1 * 8/2005 Nakano ................... 379/88.16

FOREIGN PATENT DOCUMENTS

WO    WO 98/07864 A1 *  2/1998
WO       27 9715394        5/1998
WO       12 0012890       11/2000
WO    WO 00/67700 A2 *  11/2000

(Continued)

OTHER PUBLICATIONS

Hutson et al, Current Microbiology, 1994, 28:101-110.*

(Continued)

*Primary Examiner*—N. M. Minnifield
(74) *Attorney, Agent, or Firm*—Elizabeth Arwine

(57) ABSTRACT

*Botulinum* neurotoxins, the most potent of all toxins, induce lethal neuromuscular paralysis by inhibiting exocytosis at the neuromuscular junction. The light chains (LC) of these dichain neurotoxins are a new class of zinc-endopeptidases that specifically cleave the synaptosomal proteins, SNAP-25, VAMP, or syntaxin at discrete sites. The present invention relates to the construction, expression, purification, and use of synthetic or recombinant *botulinum* neutoroxin genes. For example, a synthetic gene for the LC of the *botulinum* neurotoxin serotype A (BoNT/A) was constructed and overexpressed in *Escherichia coli*. The gene product was purified from inclusion bodies. The methods of the invention can provide 1.1 g of the LC per liter of culture. The LC product was stable in solution at 4° C. for at least 6 months. This rBoNT/A LC was proteolytically active, specifically cleaving the Glu-Arg bond in a 17-residue synthetic peptide of SNAP-25, the reported cleavage site of BoNT/A. Its calculated catalytic efficiency $k_{cat}/K_m$ was higher than that reported for the native BoNT/A dichain. Treating the rBoNT/A LC with mercuric compounds completely abolished its activity, most probably by modifying the cysteine-164 residue located in the vicinity of the active site. About 70% activity of the LC was restored by adding $Zn^{2+}$ to a $Zn^{2+}$-free, apo-LC preparation. The LC was nontoxic to mice and failed to elicit neutralizing epitope(s) when the animals were vaccinated with this protein. In addition, injecting rBoNT/A LC into sea urchin eggs inhibited exocytosis-dependent plasma membrane resealing.

16 Claims, 20 Drawing Sheets

FOREIGN PATENT DOCUMENTS

WO        WO 02/08268 A2 *   1/2002
WO      WO 02/036758 A2 *   5/2002

OTHER PUBLICATIONS

Santos-Buelga et al, Current Microbiology, 1998, 37:312-318.*
Campbell et al, J. Clinical Microbiology, 1993, 31/9:2255-2262.*
Dasgupta et al, Biochimie, 1988, 70:811-817.*
Kiyatkin et al, Infection and Immuinty, Nov. 1997, 65/11: 4586-4591.*
Zhou et al, Protein Expression and Purification, 2004, 34: 8-16.*
Agarwal et al, Protein Expression and Purification, 2004, 34:95-102.*
Jensen et al, Toxicon, 2003, 41:691-701.*
Ahmed SA et al., 2001, "Enzymatic autocatalysis of botulinum A neurotoxin light chain" *J. Protein Chem.* 20 (3):221-231.
Schmidt JJ et al., 2001, "High-throughput assays for botulinum neurotoxin proteolytic activity: serotypes A, B, D, F" *Analytical Biochemistry* 296:130-137.
URL:http://www.cdc.gov/ncidod/srp/drugservice/immuodrugs.htm, 2001, "Immunobiologic Agents and Drugs Available from the Centers for Disease Control. Descriptions, Recommendations, Adverse Reactions and Serologic Response" Centers for Disease Control, Atlanta, GA.
Ahmed SA et al., 2000, "Light chain of botulinum A neurotoxin expressed as an inclusion body from a synthetic gene is catalytically and functionally active" *J. Protein Chem.* 19(6):475-487.
Alderton JM et al., 2000, "Evidence for a vesicle-mediated maintenance of store-operated calcium channels in a human embryonic kidney cell line" *Cell. Calcium* 28(3):161-169.
Byrne MP et al., 2000, "Fermentation, purification, and efficacy of a recombinant vaccine candidate against botulinum neurotoxin type F from *Pichia pastoris*" *Protein Expr Purif.* 18(3):327-337.
Dalbey RE et al., 2000, "Evolutionarily related insertion pathways of bacterial, mitochondrial, and thylakoid membrane proteins" *Annu. Rev. Cell Dev. Biol.* 16:51-87.
Ettinger RA et al., 2000, "Beta 57-Asp plays an essential role in the unique SDS stability of HLA-DQA1 *0102/DQB1 *0602 alpha beta protein dimer, the class II MHC allele associated with protection from insulin-dependent diabetes mellitus" *J. Immunol* 165:3232-3238.
Kadkhodayan S et al., 2000, "Cloning, expression, and one-step purification of the minimal essential domain of the light chain of botulinum neurotoxin type A" *Protein Expr. Purif.* 19(1):125-130.
Knapp M et al., 2000, "The crystal structure of botulinum toxin A zinc protease domain." Presented at the 37th Annual Meeting of the Interagency Botulinum Research Coordinating Committee, Oct. 17-20, 2000, Alisomar, California.
Li L et al., 2000, "Role of zinc binding in type A botulinum neurotoxin light chain's toxic structure" *Biochemistry* 39: 10581-10586.
Strasser A et al., 2000, "Apoptosis signaling" *Annu. Rev. Biochem* 69:217-245.
Cai S et al., 1999, "Enhancement of the endopeptidase activity of botulinum neurotoxin by its associated proteins and dithiothreitol" *Biochemistry* 38:6903-6910.

Claiborne A et al., 1999, "Protein-sulfenic acids: diverse roles for an unlikely player in enzyme catalysis and redox regulation" *Biochemistry* 38:15407-15416.
Lacy DB et al., 1999, "Sequence homology and structural analysis of the clostridial neurotoxins" *J. Mol. Biol.* 291: 1091-1104.
Li L et al., 1999, "High-level expression, purification, and characterization of recombinant type A botulinum neurotoxin light chain" *Protein Expr. Purif.* 17:339-344.
Li L et al., 1999, "In vitro translation of type A *Clostridium botulinum* neurotoxin heavy chain and analysis of its binding to rat synaptosomes" *J. Protein Chem.* 18(1):89-95.
Byrne MP et al., 1998, "Purification, Potency, and Efficacy of the *Botulinum neurotoxin* Type A Binding Domain from *Pichia pastoris* as a Recombinant Vaccine Candidate," *Infect. Immun.* 66:4817-4822.
Fu F et al., 1998, "Role of zinc in the structure and toxic activity of botulinum neurotoxin" *Biochemistry* 37:5267-5278.
Lacy DB et al., 1998, "Crystal Structure of *Botulinum neurotoxin* Type A and Implications for Toxicity," *Nat. Struct. Biol.* 5:898-902.
Nowakowski JL et al., 1998, "Production of an expression system for a synaptobrevin fragment to monitor cleavage by botulinum neurotoxin B" *J. Protein Chem.* 17:453-462.
Potter KJ et al., 1998, "Production and purification of the heavy-chain fragment C of botulinum neurotoxin, serotype B, expressed in the methylotrophic yeast *Pichia pastoris*" *Protein Expr Purif.* 13(3):357-365.
Schmidt JJ et al., 1998, "Type A botulinum neurotoxin proteolytic activity: development of competitive inhibitors and implications for substrate specificity at the S1' binding subsite" *FEBS Lett.* 435:61-64.
Smith LA, 1998, "Development of recombinant vaccines for botulinum neurotoxin" *Toxicon.* 36(11):1539-48.
Adler M et al., 1997, "Protection by the heavy metal chelator N,N,N',N'-tetrakis (2-pyridylmethyl)ethylenediamine (TPEN) against the lethal action of botulinum neurotoxin A and B" *Toxicon* 35:1089-1100.
Brown DR et al., 1997, "Identification and Characterization of a Neutralizing Monoclonal Antibody Against *Botulinum neurotoxin*, Serotype F, Following Vaccination with Active Toxin," *Hybridoma*, 16:447-456.
Chen F et al., 1997, "Antibody mapping to domains of botulinum neurotoxin serotype A in the complexed and uncomplexed forms" *Infect. Immun.* 65:1626-1630.
Chiruvolu V et al., 1997, Recombinant Protein Expression in an Alcohol Oxidase-Defective Strain of *Pichia pastoris* in Feed-Batch Fermentations, *Enzyme Microbiol. Technol.* 21: 277-283.
Kiyatkin N et al., 1997, "Induction of an immune response by oral administration of recombinant botulinum toxin" *Infect. Immun.* 65:4586-4591.
Lebeda FJ et al., 1997, "Predicting Differential Antigen-Antibody Contact Regions Based on Solvent Accessibility," *J. Protein Chem.* 16:607-618.
Schmidt JJ et al., 1997, "Endoproteinase activity of type A botulinum neurotoxin: substrate requirements and activation by serum albumin" *J. Protein Chem.* 16(1):19-26.
Sheridan RE et al., 1997, "Structural features of aminoquinolines necessary for antagonist activity against botulinum neurotoxin" *Toxicon* 35:1439-1451.
Washbourne P et al., 1997, "*Botulinum neurotoxin* types A and E require the SNARE motif in SNAP-25 for proteolysis" *FEBS Lett.* 418:1-5.

Dertzbaugh MT et al., 1996, "Mapping of protective and cross-reactive domains of the type A neurotoxin of *Clostridium botulinum*" *Vaccine* 14:1538-1544.

Foran P et al., 1996, "*Botulinum neurotoxin* C1 cleaves both syntaxin and SNAP-25 in intact and permeabilized chromaffin cells: correlation with its blockade of catecholamine release" *Biochemistry* 35:2630-2636.

Auld DS, 1995, "Removal and replacement of metal ions in metallopeptidases" *Meth. Enzymol.* 248:228-242.

Bi GQ et al., 1995, "Calcium-regulated exocytosis is required for cell membrane resealing" *J. Cell Biol.* 131:1747-1758.

Cardosa F et al., 1995, "Clinical use of botulinum neurotoxins". In *Current Topics in Microbiology and Immunology* (Capron A et al., eds.), Springer-Verlag, Germany, 195:123-141.

Clayton MA et al., 1995, "Protective vaccination with a recombinant fragment of *Clostridium botulinum* Neurotoxin serotype A expressed from a synthetic gene in *Escherichia coli*" *Infect Immun.* 63(7):2738-2742.

Klatt P et al., 1995, "Structural analysis of porcine brain nitric oxide synthase reveals a role for tetrahydrobiopterin and L-arginine in the formation of an SDS-resistant dimer" *EMBO J.* 14:3687-3695.

LaPenotiere HF et al., 1995, "Expression of a large, nontoxic fragment of botulinum neurotoxin serotype A and its use as an immunogen" *Toxicon*. 33:(10):1383-1386.

Montecucco C et al., 1995, "Structure and function of tetanus and botulinum neurotoxins" *Q. Rev. Biophys.* 28:423-472.

Oguma K et al., 1995, "Structure and Function of *Clostridium botulinum* Toxins" *Microbiol. Immunol.* 39:161-168.

Pace CN et al., 1995, "How to measure and predict the molar absorption coefficient of a protein" *Protein Sci.* 4:2411-2423.

Romanos MA et al., 1995, "Expression of Cloned Genes in Yeast," *DNA Cloning 2: Expression Systems*, (Glover D., et al., Eds.), Oxford Univ. Press, London, pp. 123-167.

Schiavo G et al., 1995, "Intracellular targets and metalloprotease activity of tetanus and botulinum neurotoxins." In *Clostridial neurotoxins: The Molecular Pathogenesis of Tetanus and Botulism* (Montecucco, C., ed.), Springer, New York, pp. 257-273.

Schmidt JJ et al., 1995, "Proteolysis of synthetic peptides by type A botulinum neurotoxin" *J. Protein Chem.* 14(8):703-708.

Shone CC et al., 1995, "Growth of clostridia and preparation of their neurotoxins" *Curr. Top. Microbiol. Immunol.* 195:143-160.

Zhou L et al., 1995, "Expression and purification of the light chain of botulinum neurotoxin A: a single mutation abolishes its cleavage of SNAP-25 and neurotoxicity after reconstitution with the heavy chain" *Biochemistry* 34(46):15175-15181.

Foran P et al., 1994, "Differences in the protease activities of tetanus and botulinum B toxins revealed by the cleavage of vesicle-associated membrane protein and various sized fragments" *Biochemistry* 33:15365-15374.

Krieglstein KG et al., 1994, "Covalent structure of botulinum neurotoxin type A: location of sulfhydryl groups, and disulfide bridges and identification of C-termini of light and heavy chains" *J. Protein Chem.* 13:49-57.

Lebeda FJ et al.: 1994, "Secondary structural predictions for the clostridial neurotoxins" *Proteins* 20:293-300.

Li Y et al., 1994, "A single mutation in the recombinant light chain of tetanus toxin abolishes its protcolytic activity and removes the toxicity seen after reconstitution with native heavy chain" *Biochemistry* 33:7014-7020.

Montecucco C et al., 1994, "Mechanism of action of tetanus and botulinum neurotoxins" *Mol. Microbiol* 13:1-8.

Nishiki TI et al., 1994, "Identification of Protein Receptor for *Clostridium botulinum* Type B Neurotoxin in Rat Brain Synaptosomes" *J. Biol. Chem.* 269:10498-10503.

Rossetto O et al., 1994, "SNARE motif and neurotoxins" *Nature* 372:415-416.

Schiavo G et al., 1994, "Botulinum G neurotoxin cleaves VAMP/synaptobrevin at a single Ala-Ala peptide bond" *J. Biol. Chem.* 269:20213-20216.

Scorer CA et al., 1994, "Rapid Selection Using G418 of High Copy Number Transformants of *Pichia pastoris* for High-Level Foreign Gene Expression," *Bio/Technology*, 12:181-184.

Shone CC et al., 1994, "Peptide substrate specificity and properties of the zinc-endopeptidase activity of botulinum type B neurotoxin" *Eur. J. Biochem.* 225:263-270.

Steinhardt RA et al., 1994, "Cell membrane resealing by a vesicular mechanism similar to neurotransmitter release" *Science* 263:390-393.

Baltz RH et al., eds., 1993, *Industrial Microorganisms: Basic and Applied Molecular Genetics*, American Society for Microbiology, Washington, D.C., pp. 122-126.

Blasi J et al., 1993, "*Botulinum neurotoxin* A selectively cleaves the synaptic protein SNAP-25" *Nature* 365:160-163.

Campbell KD et al., 1993 "Gene probes for identification of the botulinal neurotoxin gene and specific identification of neurotoxin types B, E, and F" *J Clin Microbiol*. 31(9):2255-2262.

Cregg JM et al., 1993, "Recent Advances in the Expression of Foreign Genes in *Pichia pastoris,* " *Bio/Technology*, 11:905-910.

de Paiva A et al., 1993, "A role for the interchain disulfide or its participating thiols in the internalization of botulinum neurotoxin A revealed by a toxin derivative that binds to ecto-acceptors and inhibits transmitter release intracellularly" *J. Biol. Chem.* 268:20838-20844.

Dertzbaugh M et al., May 1993, "Cloning and Expression of Peptides derived from the botulinum neurotoxin serotype A gene" 93rd American Society for Microbiology General Meeting, Atlanta, GA, Session 334, E-105, p. 161.

Gimenez JA et al., 1993, "Botulinum Type A neurotoxin digested with pepsin yields 132, 97, 72, 45, 42, and 18 kD fragments" *J Protein Chem*. 12(3):351-363.

LaPenotiere HF et al., 1993, "Development of a molecular engineered vaccine for C. botulinum neurotoxins" in Botulinum and Tetanus Toxins (DasGupta BR, ed.) Plenum Press, New York.

Schiavo G et al., 1993, "Identification of the Nerve Terminal Targets of *Botulinum neurotoxin* Serotypes A, D, and E" *J. Biol. Chem.* 268:23784-23787.

Shone CC et al., 1993, "Proteolytic Cleavage of Synthetic Fragments of Vesicle-Associated Membrane Protein, Isoform-2 by Botulinum Type B Neurotoxin" *Eur. J. Biochem.* 217:965-971.

Simpson LL et al., 1993, "Chelation of zinc antagonizes the neuromuscular blocking properties of the seven serotypes of botulinum neurotoxin as well as tetanus toxin" *J. Pharmacol. Exp. Ther*. 267:720-727.

Sreekrishna K, 1993, "Strategies for Optimizing Protein Expression and Secretion in the Methylotrophic Yeast

*Pichia pastoris,"* Industrial Microrganisms: Basic and Applied Molecular Genetics, Baltz, R. H., et al, Eds.), pp. 119-126, Am. Soc. Microbiol., Washington, DC.

Ahmed SA et al., 1992, "Active-site structural comparison of streptococcal NADH peroxidase and NADH oxidase. Reconstitution with artificial flavins" *J. Biol. Chem.* 267: 3832-3840.

Kurazono H et al., 1992, "Minimal essential domains specifying toxicity of the light chains of tetanus toxin and botulinum neurotoxin type A" *J Biol Chem.* 267(21):14721-14729.

Montal MS et al., 1992, "Identification of an Ion Channel-Forming Motif in the Primary Structure of Tetanus and *Botulinum neurotixins*" *FEBS* 313:12-18.

Romanos MA et al., 1992, "Foreign Gene Expression in Yeast: A Review," *Yeast*, 8:423-488.

Schiavo G et al., 1992, "Tetanus and *Botulinum-B nuerotoxins* Block Neurotransmitter Release by Proteolytic Cleavage of Synaptobrevin" *Nature* 359:832-835.

Schiavo G et al., 1992, "Tetanus Toxin is a Zinc Protein and its Inhibition of Neurotransmitter Release and Protease Activity Depend on Zinc" *EMBO J.* 11:3577-3583.

Whelan SM et al., 1992, "Molecular cloning of the *Clostridium botulinum* structural gene encoding the type B neurotoxin and determination of its entire nucleotide sequence" *Appl. Environ. Microbiol.* 58:2345-2354.

Clare JJ et al., 1991, "High-Level Expression of Tetanus Toxin Fragment C in *Pichia pastoris* Strains Containing Multiple Tandem Integrations of the Gene," *Bio/Technology* 9:455-460.

Niemann H et al., 1991, "*Clostridial neurotoxins*: from toxins to therapeutic tools?" *Behring Inst Mitt.* 89:153-162.

Poulain B et al., 1991, "Heterologous Combinations of Heavy and Light Chains from *Botulinum neurotoxin* A and Tetanus Toxin Inhibit Neurotransmitter Release in *Aplysia*" *J. Biol. Chem.* 266:9580-9585.

Romanos MA, et al., 1991, "Expression of Tetanus Toxin Fragment C in Yeast: Gene Synthesis is Required to Eliminate Fortuitous Polyadenylation Sites in AT-rich DNA, " *Nucleic Acids Res.* 19:1461-1467.

Ahnert-Hilger G et al., 1990, "Chains and fragments of tetanus toxin, and their contribution to toxicity" *J Physiol* (Paris) 84(3):229-236.

Andersson SG et al., 1990, "Codon preferences in free-living microorganisms" *Microbial. Rev.* 54(2):198-210.

DasGupta BR et al., 1990, "*Botulinum neurotoxin* type A: sequence of amino acids at the N-terminus and around the nicking site" *Biochemie* 72:661-664.

Dekleva ML et al., 1990, "Purification and characterization of a protease from *Clostridium botulinum* type A that nicks single-chain type A botulinum neurotoxin into the di-chain form" *J. Bacteriol.* 172:2498-2503.

Thompson DE et al., 1990, "The complete amino acid sequence of the *Clostridium botulinum* type A neurotoxin, deduced by nucleotide sequence analysis of the encoding gene" *Eur. J. Biochem.* 189:73-81.

Wadsworth JDF et al., 1990, "Botulinum Type F Neurotoxin" *Biochem. J.* 268:123-128.

Bittner MA et al., 1989, "Isolated light chains of botulinum neurotoxins inhibit exocytosis. Studies in digitonin-permeabilized chromaffin cells" *J. Biol. Chem.* 264:10354-10360.

DasGupta BR et al., 1989, "C. botulinum neurotoxin types A and E: isolated light chain breaks down into two fragments. Comparison of their amino acid sequences with tetanus neurotoxin" *Biochimie* 71:1193-1200.

DasGupta BR, 1989, "The Structure of *Botulinum neurotoxins*" *Botulinum neurotoxin and Tetanus Toxin*, (Simpson, L.L., Ed.) Academic Press, New York, pp. 53-67.

Kozaki S. et al., 1989, "Immunological characterization of papain-induced fragments of *Clostridium botulinum* type A neurotoxin and interaction of the fragments with brain synaposomes" *Infect Immun.* 57(9):2634-2639.

Kozaki et al., 1989, "Antibodies against Botulism Neurotoxin", L.L. Simpson, ed. Academic Press, New York, pp. 301-318.

Makoff AJ et al., 1989, "Expression of Tetanus Toxin Fragment C in *E. coli*: High Level Expression by Removing Rare Condons," *Nucleic Acids Res.* 17:10191-10201.

Middlebrook JL, 1989, "Cell Surface Receptors for Protein Toxins" *Botulinum neurotoxins and Tetanus Toxin*, (Simpson, L.L., Ed.) Academic Press, New York, pp. 95-119.

Maisey EA et al., 1988, "Involvement of the constituent chains of botulinum neurotoxins A and B in the blockade of neurotransmitter release" *Eur. J. Biochem.* 177:683-691.

Sathyamoorthy V et al., 1988, "*Botulinum neurotoxin* type A: cleavage of the heavy chain into two halves and their partial sequences" *Arch Biochem Biophys.* 266:(1):142-151.

Siegel LS, 1988, "Human Immune Response to Botulinum Pentavalent (ABCDE) Toxoid Determined by a Neutralization Test and by an Enzyme-Linked Immunosorbent Assay" *J. Clin. Microbiol.* 26:2351-2356.

Sreekrishna K et al., 1988, "High Level Expression of Heterologous Proteins in Methylotrophic Yeast *Pichia pastoris,"* J. Bas. Microbiol. 28:265-278.

Winkler HH et al., 1988, "Codon usage in selected AT-rich bacteria" *Biochimie* 70:977-986.

Schagger H et al., 1987, "Tricine-sodium dodecyl sulfate-polyacrylamide gel electrophoresis for the separation of proteins in the range from 1 to 100 kDa" *Anal. Biochem.* 166:368-379.

Shone CC et al., 1987, A 50-kDa Fragment from the $NH_2$-terminus of the Heavy Subunit of *Clostridium botulinum* Type A Neurotoxin Forms Channels in Lipid Vesicles, *Euro. J. Biochem.* 167:175-180.

Sonnabend WF et al., 1987, "Intestinal Toxicoinfection by *Clostridium botulinum* Type F in an Adult. Case Associated with Guillian-Barre Syndrome" *Lancet* 1:357-361.

Ahmed SA et al., 1986, "Identification of three sites of proteolytic cleavage in the hinge region between the two domains of the beta 2 subunit of tryptophan synthase of *Escherichia coli* or *Salmonella typhimurium"* Biochemistry 25, 3118-3124.

Black JD et al., 1986, "Interaction of $^{125}$I-botulinum Neurotoxins with Nerve Terminals. I. Ultrastructural Autoradiographic Localization and Quantitation of Distinct Membrane Accepters for Types A and B on Motor Nerves" *J. Cell Biol.* 103:521-534.

Habermann E et al., 1986, "*Clostridial neurotoxins* : Handling and Action at the Cellular and Molecular Level" *Cur. Top. Microbiol. Immunol.* 129:93-179.

Simpson LL, 1986, "Molecular Pharmacology of Botulinum Toxin and Tetanus Toxin" *Annu. Rev. Pharmacol. Toxicol.* 26:427-453.

Cregg JM et al., 1985, "*Pichia pastoris* as a Host System for Transformations," *Mol. Cell. Biol.* 5:3376-3385.

Sathyamoorthy V et al., 1985, "Separation, purification, partial characterization and comparison of the heavy and light chains of botulinum neurotoxin types A, B, and E" *J Biol Chem.* 260(19):10461-10466.

Schmidt JJ et al., 1985, "Partial amino acid sequences of botulinum neurotoxins types B and E" *Arch. Biochem. Biophys.* 238:544-548.

Shone CC et al., 1985, Inactivation of *Clostridium botulinum* Type A Neurotoxin by Trypsin and Purification of Two Tryptic Fragments. Proteolytic Action Near the COOH-terminus of the Heavy Subunit Destroys Toxin-Binding Activity, *Eur. J. Biochem.* 151:75-82.

Anderson JH et al., 1981, "Clinical Evaluation of Botulinum Toxoids" *Biomedical Aspects of Botulism*, (Lewis, G.E., Ed.) Academic Press, New York, pp. 233-246.

Syuto B et al., 1981, "Separation and characterization of heavy and light chains form *Clostridium botulinum* type C toxin and their reconstitution" *J. Biol. Chem.* 256:3712-3717.

Hatheway CL, 1976, "Toxoid of *Clostridium botulinum* Type F: Purification and Immunogenicity Studies" *Appl. Environ. Microbiol.* 31:234-242.

DasGupta BR et al., 1972, "A Common Subunit Structure in *Clostridium botulinum* Type A, B, and E Toxins" *Biophys. Res. Commun.* 48:108-112.

Midura TF et al., 1972, "*Clostridium botulinum* Type F: Isolation from Venison Jerky" *Appl. Microbiol.* 24:165-167.

Laemmli UK, 1970, "Cleavage of structural proteins during the assembly of the head of bacteriophage T4" *Nature* 227:680-685.

van Heyningen WE, 1968, "Tetanus" *Sci. Am.* 218:69-77.

Fiock MA et al., 1963, "Studies of Immunities to Toxins of *Clostridium botulinum*. IX. Immunologic Response of Man to Purified Pentavalent ABCDE Botulinum Toxoid" *J. Immunol.* 90:697-702.

* cited by examiner

| Purification of LcA, LcA+Belt, and LcA+Hn from *E. coli* cells | | | |
|---|---|---|---|
| Purification Step | Protein Conc. (mg/ml) | Volume (mL) | Percentage of desired protein in solute |
| LcA | | | |
| Load column 1 | 1.764 | 35 | 10% |
| Load column 2 | 0.557 | 12 | 85% |
| Peak column 2 | 0.748 | 4 | >95% |
| LcA+Belt | | | |
| Load column 1 | 1.749 | 35 | 7% |
| Load column 2 | 0.454 | 12 | 90% |
| Peak column 2 | 0.226 | 4 | >95% |
| LcA+Hn | | | |
| Load column 1 | 1.799 | 35 | 5% |
| Load column 2 | 0.816 | 12 | 85% |
| Peak column 2 | 0.401 | 4 | >95% |
| LcB | | | |
| Load column 1 | 1.42 | 20 | 9% |
| Load column 2 | 0.79 | 8 | 85% |
| Peak column 2 | 1.032 | 2 | >95% |

*Fig. 18*

SEQUENCE LISTING

<160> NUMBER OF SEQ ID NOS: 47

<210> SEQ ID NO 1
<211> LENGTH: 16
<212> TYPE: PRT
<213> ORGANISM: Clostridium botulinum
<220> FEATURE:
<221> NAME/KEY: PEPTIDE
<222> LOCATION: (0)...(0)
<223> OTHER INFORMATION: N-terminal residues of mature, wild-type botulinum neurotoxin

<400> SEQUENCE: 1

Pro Phe Val Asn Lys Gln Phe Asn Tyr Lys Asp Pro Val Asn Gly Val
 1               5                  10                  15

<210> SEQ ID NO 2
<211> LENGTH: 17
<212> TYPE: PRT
<213> ORGANISM: Human
<220> FEATURE:
<221> NAME/KEY: PEPTIDE
<222> LOCATION: (0)...(0)
<223> OTHER INFORMATION: Residues 187-203 of SNAP-25

<400> SEQUENCE: 2

Ser Asn Lys Thr Arg Ile Asp Glu Ala Asn Gln Arg Ala Thr Lys Met
 1               5                  10                  15

Leu

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide; control for phosphorylation
      experiments

<400> SEQUENCE: 3

Lys Val Glu Lys Ile Gly Glu Gly Thr Gly Val Val Tyr Lys
 1               5                  10

<210> SEQ ID NO 4
<211> LENGTH: 1403
<212> TYPE: DNA
<213> ORGANISM: Artificial Sequence
<220> FEATURE:
<223> OTHER INFORMATION: Synthetic botulinum neurotoxin light chain of
      serotype A based on wild-type Clostridium
      botulinum sequence

<400> SEQUENCE: 4

| | | | | | |
|---|---|---|---|---|---|
| gaattcccat | ggttcagttc | gttaacaaac | agttcaacta | caaagacccg | gttaacggtg | 60 |
| ttgacatcgc | ttacatcaaa | atcccgaacg | ttggtcagat | gcagccggtt | aaagcattca | 120 |
| aaatccacaa | caaaatctgg | ttatcccgg | aacgtgacac | tttcactaac | ccggaagaag | 180 |
| gtgacctgaa | cccgccgccg | gaagctaaac | aggttccggt | tcttactac | gactctactt | 240 |
| acctgtctac | tgacaacgaa | aaggacaact | acctgaaagg | tgttactaaa | ctgtttgaac | 300 |
| gtatctactc | tactgacctg | ggtcgcatgc | tgctcacttc | tatcgttcgt | ggtatcccgt | 360 |
| tctggggtgg | ttctactatc | gacactgaac | tgaaagttat | cgacactaac | tgcatcaacg | 420 |
| ttatccagcc | ggacggttct | taccgttctg | aagaactgaa | cctggttatc | atcggtccgt | 480 |
| ctgctgacat | catccagttt | gaatgcaaat | ctttcggtca | cgaagttctg | aacctgactc | 540 |
| gtaacggtta | cggttctact | cagtacatcc | gtttctctcc | ggacttcact | ttcggtttcg | 600 |
| aagaatctct | ggaagttgac | actaacccgc | tgctgggtgc | tggtaaattc | gctactgacc | 660 |
| cggctgttac | tctggctcac | gaactgatcc | acgctggtca | ccgtctgtac | ggtatcgcta | 720 |
| tcaacccgaa | ccgtgttttc | aaagttaaca | ctaacgctta | ctacgaaatg | tctggtctgg | 780 |
| aagtttcttt | tgaagaactg | cgtactttcg | gtggtcacga | cgctaaattc | atcgactctc | 840 |
| tgcaggaaaa | cgagttccgt | ctgtactact | acaacaaatt | caaagacatc | gcttctactc | 900 |
| tgaacaaagc | taaatctatc | gttggtacca | ctgcttctct | gcagtacatg | aagaacgttt | 960 |
| tcaaagaaaa | gtacctgctg | tctgaagaca | cttctggtaa | attctctgtt | gacaaactga | 1020 |
| aattcgacaa | actgtacaaa | atgctgactg | aaatctacac | tgaagacaac | ttcgttaaat | 1080 |
| tcttcaaagt | tctgaaccgt | aaaacttacc | tgaacttcga | caaagctgtt | ttcaaaatca | 1140 |
| acatcgttcc | gaaagttaac | tacactatct | acgacggttt | caacctgcgt | aacactaacc | 1200 |
| tggctgctaa | cttcaacggt | cagaacactg | aaatcaacaa | catgaacttc | actaaactga | 1260 |
| agaacttcac | tggtctgttt | gagttctaca | aactgctgtg | cgttcgtggt | atcatcactt | 1320 |
| ctaaaactaa | atctctggac | aaaggttaca | acaaactggt | tccgcgtggt | tctcatcatc | 1380 |
| atcatcatca | ttaatgagaa | tcc | | | | 1403 |

<210> SEQ ID NO 5
<211> LENGTH: 461
<212> TYPE: PRT
<213> ORGANISM: Artificial Sequence

```
<220> FEATURE:
<223> OTHER INFORMATION: Synthetic botulinum neurotoxin light chain of
      serotype A based on wild-type Clostridium
      botulinum sequence

<400> SEQUENCE: 5

Met Val Gln Phe Val Asn Lys Gln Phe Asn Tyr Lys Asp Pro Val Asn
1               5                   10                  15

Gly Val Asp Ile Ala Tyr Ile Lys Ile Pro Asn Val Gly Gln Met Gln
                20                  25                  30

Pro Val Lys Ala Phe Lys Ile His Asn Lys Ile Trp Val Ile Pro Glu
            35                  40                  45

Arg Asp Thr Phe Thr Asn Pro Glu Glu Gly Asp Leu Asn Pro Pro Pro
        50                  55                  60

Glu Ala Lys Gln Val Pro Val Ser Tyr Tyr Asp Ser Thr Tyr Leu Ser
65                  70                  75                  80

Thr Asp Asn Glu Lys Asp Asn Tyr Leu Lys Gly Val Thr Lys Leu Phe
                85                  90                  95

Glu Arg Ile Tyr Ser Thr Asp Leu Gly Arg Met Leu Leu Thr Ser Ile
                100                 105                 110

Val Arg Gly Ile Pro Phe Trp Gly Gly Ser Thr Ile Asp Thr Glu Leu
            115                 120                 125

Lys Val Ile Asp Thr Asn Cys Ile Asn Val Ile Gln Pro Asp Gly Ser
130                 135                 140

Tyr Arg Ser Glu Glu Leu Asn Leu Val Ile Ile Gly Pro Ser Ala Asp
145                 150                 155                 160

Ile Ile Gln Phe Glu Cys Lys Ser Phe Gly His Glu Val Leu Asn Leu
                165                 170                 175

Thr Arg Asn Gly Tyr Gly Ser Thr Gln Tyr Ile Arg Phe Ser Pro Asp
                180                 185                 190

Phe Thr Phe Gly Phe Glu Glu Ser Leu Glu Val Asp Thr Asn Pro Leu
            195                 200                 205

Leu Gly Ala Gly Lys Phe Ala Thr Asp Pro Ala Val Thr Leu Ala His
210                 215                 220

Glu Leu Ile His Ala Gly His Arg Leu Tyr Gly Ile Ala Ile Asn Pro
225                 230                 235                 240

Asn Arg Val Phe Lys Val Asn Thr Asn Ala Tyr Tyr Glu Met Ser Gly
                245                 250                 255

Leu Glu Val Ser Phe Glu Glu Leu Arg Thr Phe Gly Gly His Asp Ala
                260                 265                 270

Lys Phe Ile Asp Ser Leu Gln Glu Asn Glu Phe Arg Leu Tyr Tyr Tyr
            275                 280                 285

Asn Lys Phe Lys Asp Ile Ala Ser Thr Leu Asn Lys Ala Lys Ser Ile
290                 295                 300

Val Gly Thr Thr Ala Ser Leu Gln Tyr Met Lys Asn Val Phe Lys Glu
305                 310                 315                 320

Lys Tyr Leu Leu Ser Glu Asp Thr Ser Gly Lys Phe Ser Val Asp Lys
                325                 330                 335

Leu Lys Phe Asp Lys Leu Tyr Lys Met Leu Thr Glu Ile Tyr Thr Glu
                340                 345                 350

Asp Asn Phe Val Lys Phe Lys Val Leu Asn Arg Lys Thr Tyr Leu
            355                 360                 365

Asn Phe Asp Lys Ala Val Phe Lys Ile Asn Ile Val Pro Lys Val Asn
370                 375                 380
```

```
Tyr Thr Ile Tyr Asp Gly Phe Asn Leu Arg Asn Thr Asn Leu Ala Ala
385                 390                 395                 400

Asn Phe Asn Gly Gln Asn Thr Glu Ile Asn Asn Met Asn Phe Thr Lys
            405                 410                 415

Leu Lys Asn Phe Thr Gly Leu Phe Glu Phe Tyr Lys Leu Leu Cys Val
            420                 425                 430

Arg Gly Ile Ile Thr Ser Lys Thr Lys Ser Leu Asp Lys Gly Tyr Asn
            435                 440                 445

Lys Leu Val Pro Arg Gly Ser His His His His His His
450                 455                 460

<210> SEQ ID NO 6
<211> LENGTH: 1323
<212> TYPE: DNA
<213> ORGANISM: Artificial Sequence
<220> FEATURE:
<223> OTHER INFORMATION: Synthetic botulinum neurotoxin light chain of
      serotype B based on wild-type Clostridium
      botulinum sequence

<400> SEQUENCE: 6
atgccagtta ctattaacaa cttcaactac aacgacccaa ttgacaacaa caacattatt      60
atgatggagc caccattcgc tagaggtact ggtagatact acaaggcttt caagattact     120
gacagaattt ggattattcc agagagatac actttcggtt acaagccaga ggacttcaac     180
aagtcttctg gtattttcaa cagagacgtt tgtgagtact acgacccaga ctacttgaac     240
actaacgaca gaagaaacat tttcttgcaa actatgatta gttgttcaa cagaattaag      300 tctaagccat gggtgagaa gttgttggag atgattatta cggtattcc atacttgggt      360 gacagaagag ttccattgga ggagttcaac actaacattg cttctgttac tgttaacaag     420
ttgatttcta acccaggtga ggttgagaga aagaagggta ttttcgctaa cttgattatt     480
ttcggtccag gtccagtttt gaacgagaac gagactattg acattggtat tcaaaaccac     540
ttcgcttcta gagagggttt cggtggtatt atgcaaatga agttctgtcc agagtacgtt     600
tctgtttcca caacgttca agagaacaag ggtgcttcta ttttcaacag aagaggttac     660
ttctctgacc cagctttgat tttgatgcac gagttgattc acgttttgca cggtttgtac     720
ggtattaagg ttgacgactt gccaattgtt ccaaacgaga gaagttctt catgcaatct     780 actgacgcta tcaagctga ggagttgtac actttcggtg gtcaagaccc atctattatt     840
actccatcta ctgacaagtc tatttacgac aaggttttgc aaaacttcag aggtattgtt     900
gacagattga caaggttttt ggtttgtatt tctgacccaa acattaacat taacatttac     960
aagaacaagt tcaaggacaa gtacaagttc gttgaggact ctgagggtaa gtactctatt    1020
gacgttgagt ctttcgacaa gttgtacaag tctttgatgt tcggttttcac tgagactaac    1080 attgctgaga actacaagat taagactaga gcttcttact tctctgactc tttgccacca    1140
gttaagatta gaacttgtt ggacaacgag attatcacta ttgaggaggg tttcaacatt    1200
tctgacaagg acatggagaa ggagtacaga ggtcaaaaca aggctattaa caagcaagct    1260
tacgaggaga tttctaagga gcacttggct gtttacaaga ttcaaatgtg taagtctgtt    1320
aag                                                                  1323

<210> SEQ ID NO 7
<211> LENGTH: 441
<212> TYPE: PRT
<213> ORGANISM: Artificial Sequence
<220> FEATURE:
```

<223> OTHER INFORMATION: Synthetic botulinum neurotoxin light chain of serotype B based on wild-type Clostridium botulinum sequence

<400> SEQUENCE: 7

```
Met Pro Val Thr Ile Asn Asn Phe Asn Tyr Asn Asp Pro Ile Asp Asn
 1               5                  10                  15

Asn Asn Ile Ile Met Met Glu Pro Pro Phe Ala Arg Gly Thr Gly Arg
             20                  25                  30

Tyr Tyr Lys Ala Phe Lys Ile Thr Asp Arg Ile Trp Ile Ile Pro Glu
         35                  40                  45

Arg Tyr Thr Phe Gly Tyr Lys Pro Glu Asp Phe Asn Lys Ser Ser Gly
     50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                 85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
```

|   |   |   |   | 385 |   |   |   |   | 390 |   |   |   |   | 395 |   |   |   |   | 400 |
Ser Asp Lys Asp Met Glu Lys Glu Tyr Arg Gly Gln Asn Lys Ala Ile
            405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys
            435             440

<210> SEQ ID NO 8
<211> LENGTH: 1332
<212> TYPE: DNA
<213> ORGANISM: Artificial Sequence
<220> FEATURE:
<223> OTHER INFORMATION: Synthetic botulinum neurotoxin light chain of
      serotype C1 based on wild-type Clostridium
      botulinum sequence

<400> SEQUENCE: 8
atgccaatca ccatcaacaa cttcaactac tcagaccctg tcgacaacaa gaacattctg      60
tacctggaca ctcacctgaa caccctagct aacgagcctg agaaggcctt tcggatcacc     120
ggaaacatct gggtcatccc tgatcgtttc tcccgtaact ccaaccccaa cctgaacaag     180
cctcctcggg tcaccagccc taagagtggt tactacgacc taactacct gagtaccgac      240 tctgacaagg acaccttcct gaaggagatc atcaagctgt tcaagcgtat caactcccgt     300
gagatcggag aggagctcat ctacagactt cgaccgata tccccttccc tggtaacaac     360
aatactccaa tcaacacctt cgacttcgac gtcgacttca actccgtcga cgtcaagact     420
cggcagggta caactgggt taagactggt agcatcaacc cttccgtcat catcactgga     480
cctcgtgaga acatcatcga cccagagact tccacgttca gctgactaa caacaccttc     540 gcggctcaag aaggattcgg tgctctgtca atcatctcca tctcacctcg tttcatgctg     600
acctactcga acgcaaccaa cgacgtcgga gagggtaggt ctctctaagtc tgagttctgc     660 atggacccaa tcctgatcct gatgcatgag ctgaaccatg caatgcacaa cctgtacgga     720
atcgctatcc caaacgacca gaccatctcc tccgtgacct ccaacatctt ctactcccag     780
tacaacgtga agctggagta cgcagagatc tacgctttcg gaggtccaac tatcgacctt     840
atccctaagt ccgctaggaa gtacttcgag gagaaggctt tggattacta cagatccatc     900
gctaagagac tgaacagtat caccaccgca aacccttcca gcttcaacaa gtacatcggt     960
gagtacaagc agaagctgat cagaaagtac cgtttcgtcg tcgagtcttc aggtgaggtc    1020 acagtaaaacc gtaacaagtt cgtcgagctg tacaacgagc ttacccagat cttcacagag    1080
ttcaactacg ctaagatcta caacgtccag aacaggaaga tctacctgtc caacgtgtac    1140
actccggtga cggcgaacat cctggacgac aacgtctacg acatccagaa cggattcaac    1200
atccctaagt ccaacctgaa cgtactattc atgggtcaaa acctgtctcg aaacccagca    1260
ctgcgtaagg tcaaccctga gaacatgctg tacctgttca ccaagttctg ccacaaggca    1320
atcgacggta ga                                                         1332

<210> SEQ ID NO 9
<211> LENGTH: 444
<212> TYPE: PRT
<213> ORGANISM: Artificial Sequence
<220> FEATURE:
<223> OTHER INFORMATION: Synthetic botulinum neurotoxin light chain of
      serotype C1 based on wild-type Clostridium
      botulinum sequence -continued

<400> SEQUENCE: 9

```
Met Pro Ile Thr Ile Asn Asn Phe Asn Tyr Ser Asp Pro Val Asp Asn
  1               5                  10                  15

Lys Asn Ile Leu Tyr Leu Asp Thr His Leu Asn Thr Leu Ala Asn Glu
             20                  25                  30

Pro Glu Lys Ala Phe Arg Ile Thr Gly Asn Ile Trp Val Ile Pro Asp
         35                  40                  45

Arg Phe Ser Arg Asn Ser Asn Pro Asn Leu Asn Lys Pro Pro Arg Val
     50                  55                  60

Thr Ser Pro Lys Ser Gly Tyr Tyr Asp Pro Asn Tyr Leu Ser Thr Asp
 65                  70                  75                  80

Ser Asp Lys Asp Thr Phe Leu Lys Glu Ile Ile Lys Leu Phe Lys Arg
                 85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415
```

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg
            435                 440

<210> SEQ ID NO 10
<211> LENGTH: 1323
<212> TYPE: DNA
<213> ORGANISM: Artificial Sequence
<220> FEATURE:
<223> OTHER INFORMATION: Synthetic botulinum neurotoxin light chain of
      serotype D based on wild-type Clostridium
      botulinum sequence

<400> SEQUENCE: 10

| | | |
|---|---|---|
| atgacctggc cagtcaagga cttcaactac tccgacccag tcaacgacaa cgacatcttg | 60 |
| tacttgagaa tcccacaaaa caagttgatc accaccccag tcaaggcttt catgatcacc | 120 |
| cagaacacct gggttatccc agagagattc tcctccgaca ccaacccatc cctgtccaag | 180 |
| ccaccaagac caacctccaa gtaccagtct tactacgacc catcttactt gtctaccgac | 240 |
| gagcaaaagg acaccttctt gaagggtatt atcaagctgt tcaagagaat caacgagaga | 300 |
| gacatcggta agaagttgat caactacttg gtcgttggtt ccccattcat gggtgactcc | 360 |
| tctaccccag aggacaccct cgacttcacc agacacacca ccaacattgc cgtcgagaag | 420 |
| ttcgagaacg gttcctggaa ggtcaccaac atcatcaccc catctgtttt gatcttcggt | 480 |
| ccattgccaa acatcttgga ctacaccgcc tccctgacct gcaaggtca gcaatccaac | 540 |
| ccatccttcg agggtttcgg taccctgtct attttgaagg tcgctccaga gttcttgttg | 600 |
| accttctccg acgtcaccte caaccaatcc tccgccgtct gggtaagtc catcttctgt | 660 |
| atggacccag tcatcgcttt gatgcacgag ttgacccact ccctgcacca gttgtacggt | 720 |
| attaacatcc catctgacaa gagaatcaga ccacaggtct tgagggtt cttctcccaa | 780 |
| gacggtccaa cgttcagtt cgaggagttg tacaccttcg gtggtttgga cgtcgagatt | 840 |
| atccaaattg agagatccca attgagagag aaggctttgg gtcactacaa ggacatcgcc | 900 |
| aagagactga acaacatcaa caagaccatt ccatcttcct ggatctccaa cattgacaag | 960 |
| tacaagaaga ttttctccga agtacaac ttcgacaagg acaacaccgg taacttcgtc | 1020 |
| gttaacatcg acaagttcaa ctctttgtac tccgacttga ccaacgttat gtctgaggtt | 1080 |
| gtctactcct cccaatacaa cgtcaagaac agaaccccact acttctccag acactacttg | 1140 |
| ccagttttcg ctaacatctt ggacgacaac atttacacca tcagagacgg tttcaacttg | 1200 |
| accaacaagg gtttcaacat cgagaactcc ggtcaaaaca tcgagagaaa cccagccctg | 1260 |
| caaaagctgt cctccgagtc tgtcgtcgac ttgttcacca aggtctgttt gagattgacc | 1320 |
| aag | 1323 |

<210> SEQ ID NO 11
<211> LENGTH: 441
<212> TYPE: PRT
<213> ORGANISM: Artificial Sequence
<220> FEATURE:
<223> OTHER INFORMATION: Synthetic botulinum neurotoxin light chain of
      serotype D based on wild-type Clostridium
      botulinum sequence

<400> SEQUENCE: 11

Met Thr Trp Pro Val Lys Asp Phe Asn Tyr Ser Asp Pro Val Asn Asp
1               5                   10                  15

```
Asn Asp Ile Leu Tyr Leu Arg Ile Pro Gln Asn Lys Leu Ile Thr Thr
             20                  25                  30
Pro Val Lys Ala Phe Met Ile Thr Gln Asn Thr Trp Val Ile Pro Glu
         35                  40                  45
Arg Phe Ser Ser Asp Thr Asn Pro Ser Leu Ser Lys Pro Pro Arg Pro
     50                  55                  60
Thr Ser Lys Tyr Gln Ser Tyr Tyr Asp Pro Ser Tyr Leu Ser Thr Asp
 65                  70                  75                  80
Glu Gln Lys Asp Thr Phe Leu Lys Gly Ile Ile Lys Leu Phe Lys Arg
                 85                  90                  95
Ile Asn Glu Arg Asp Ile Gly Lys Lys Leu Ile Asn Tyr Leu Val Val
            100                 105                 110
Gly Ser Pro Phe Met Gly Asp Ser Thr Pro Glu Asp Thr Phe Asp
        115                 120                 125
Phe Thr Arg His Thr Thr Asn Ile Ala Val Glu Lys Phe Glu Asn Gly
    130                 135                 140
Ser Trp Lys Val Thr Asn Ile Ile Thr Pro Ser Val Leu Ile Phe Gly
145                 150                 155                 160
Pro Leu Pro Asn Ile Leu Asp Tyr Thr Ala Ser Leu Thr Leu Gln Gly
                165                 170                 175
Gln Gln Ser Asn Pro Ser Phe Glu Gly Phe Gly Thr Leu Ser Ile Leu
            180                 185                 190
Lys Val Ala Pro Glu Phe Leu Leu Thr Phe Ser Asp Val Thr Ser Asn
        195                 200                 205
Gln Ser Ser Ala Val Leu Gly Lys Ser Ile Phe Cys Met Asp Pro Val
    210                 215                 220
Ile Ala Leu Met His Glu Leu Thr His Ser Leu His Gln Leu Tyr Gly
225                 230                 235                 240
Ile Asn Ile Pro Ser Asp Lys Arg Ile Arg Pro Gln Val Ser Glu Gly
                245                 250                 255
Phe Phe Ser Gln Asp Gly Pro Asn Val Gln Phe Glu Glu Leu Tyr Thr
            260                 265                 270
Phe Gly Gly Leu Asp Val Glu Ile Ile Gln Ile Glu Arg Ser Gln Leu
        275                 280                 285
Arg Glu Lys Ala Leu Gly His Tyr Lys Asp Ile Ala Lys Arg Leu Asn
    290                 295                 300
Asn Ile Asn Lys Thr Ile Pro Ser Ser Trp Ile Ser Asn Ile Asp Lys
305                 310                 315                 320
Tyr Lys Lys Ile Phe Ser Glu Lys Tyr Asn Phe Asp Lys Asp Asn Thr
                325                 330                 335
Gly Asn Phe Val Val Asn Ile Asp Lys Phe Asn Ser Leu Tyr Ser Asp
            340                 345                 350
Leu Thr Asn Val Met Ser Glu Val Val Tyr Ser Ser Gln Tyr Asn Val
        355                 360                 365
Lys Asn Arg Thr His Tyr Phe Ser Arg His Tyr Leu Pro Val Phe Ala
    370                 375                 380
Asn Ile Leu Asp Asp Asn Ile Tyr Thr Ile Arg Asp Gly Phe Asn Leu
385                 390                 395                 400
Thr Asn Lys Gly Phe Asn Ile Glu Asn Ser Gly Gln Asn Ile Glu Arg
                405                 410                 415
Asn Pro Ala Leu Gln Lys Leu Ser Ser Glu Ser Val Val Asp Leu Phe
            420                 425                 430
```

```
Thr Lys Val Cys Leu Arg Leu Thr Lys
        435                 440
```

<210> SEQ ID NO 12
<211> LENGTH: 1266
<212> TYPE: DNA
<213> ORGANISM: Artificial Sequence
<220> FEATURE:
<223> OTHER INFORMATION: Synthetic botulinum neurotoxin light chain of
      serotype E based on wild-type Clostridium
      botulinum sequence

<400> SEQUENCE: 12

```
atgccaaaga ttaactcctt caactacaac gaccctgtca acgacagaac catcttgtac     60
atcaagccag gcggttgcca ggagttctac aagtccttca acatcatgaa gaacatctgg    120
atcatccccg agagaaacgt cattggtacc accccccaag acttccaccc cctacttcc    180
ttgaagaacg gagactccag ttactacgac cctaactact gcaaagtga cgaggagaag    240
gacagattct tgaagatcgt cacaaagatc ttcaacagaa tcaacaacaa cctttcagga    300
ggcatcttgt tggaggagct gtccaaggct aacccatact gggcaacga caacactcca    360
gataaccagt tccacattgg tgacgcatcc gcagttgaga ttaagttctc caacggtagc    420
caggacatcc tattgcctaa cgttatcatc atgggagcag agcctgactt gtttgagacc    480
aactcctcca acatctctct acgtaacaac tacatgccaa gcaatcacgg tttcggatcc    540
atcgctatcg tcaccttctc ccctgaatat tccttcaggt tcaacgacaa cagcatgaac    600
gagttcattc aggatcctgc tctcacgctg atgcacgaat tgatccactc cttacatgga    660
ctatatggcg ctaagggcat tactaccaag tacactatca cacagaagca gaacccccta    720
ataaccaaca tccgggtac caacatcgag gagttcttga ctttcggagg tactgacttg    780
aacatcatta ctagtgctca gtccaacgac atctacacta accttctggc tgactacaag    840
aagatcgcgt ctaagcttag caaggtccaa gtctctaacc cactgcttaa cccttacaag    900
gacgtcttcg aagcaaagta tggattggac aaggatgcta gcggaattta ctcggtcaac    960
atcaacaagt tcaacgacat cttcaagaag ctctacagct tcacggagtt cgacttggcc   1020
accaagttcc aggttaagtg taggcagact tacatcggac agtacaagta cttcaagctg   1080
tccaacctgt tgaacgactc tatctacaac atctcagaag ctacaacat caacaacttg   1140
aaggtcaact tcagaggaca gaatgcaaac ttgaacccta gaatcattac cccaatcacc   1200
ggtagaggac tggtcaagaa gatcatccgt ttctgcaaga acattgtctc tgtcaagggc   1260
atcagg                                                              1266
```

<210> SEQ ID NO 13
<211> LENGTH: 422
<212> TYPE: PRT
<213> ORGANISM: Artificial Sequence
<220> FEATURE:
<223> OTHER INFORMATION: Synthetic botulinum neurotoxin light chain of
      serotype E based on wild-type Clostridium
      botulinum sequence

<400> SEQUENCE: 13

```
Met Pro Lys Ile Asn Ser Phe Asn Tyr Asn Asp Pro Val Asn Asp Arg
  1               5                  10                  15

Thr Ile Leu Tyr Ile Lys Pro Gly Gly Cys Gln Glu Phe Tyr Lys Ser
             20                  25                  30

Phe Asn Ile Met Lys Asn Ile Trp Ile Ile Pro Glu Arg Asn Val Ile
         35                  40                  45
```

```
Gly Thr Thr Pro Gln Asp Phe His Pro Pro Thr Ser Leu Lys Asn Gly
 50                  55                  60

Asp Ser Ser Tyr Tyr Asp Pro Asn Tyr Leu Gln Ser Asp Glu Glu Lys
 65                  70                  75                  80

Asp Arg Phe Leu Lys Ile Val Thr Lys Ile Phe Asn Arg Ile Asn Asn
                 85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg
            420

<210> SEQ ID NO 14
<211> LENGTH: 1308
<212> TYPE: DNA
<213> ORGANISM: Artificial Sequence
<220> FEATURE:
```

<223> OTHER INFORMATION: Synthetic botulinum neurotoxin light chain of
      serotype F based on wild-type Clostridium
      botulinum sequence

<400> SEQUENCE: 14

| | | | | | |
|---|---|---|---|---|---|
| atgccagtcg | ctatcaactc | cttcaactac | aacgacccag | tcaacgacga | caccattttg | 60 |
| tacatgcaga | tcccatacga | ggagaagtct | aagaagtact | acaaggcttt | cgagatcatg | 120 |
| agaaacgtct | ggattatcga | gagaaacacc | atcggtacca | acccatccga | cttcgaccca | 180 |
| ccagcctctt | tgaagaacgg | ttcctccgct | tactacgacc | caaactactt | gaccaccgac | 240 |
| gccgagaagg | acagatactt | gaagaccacc | atcaagttgt | tcaagagaat | taactctaac | 300 |
| ccagccggta | aggtcttgtt | gcaagagatc | tcctacgcta | agccatacct | gggtaacgac | 360 |
| cacaccccaa | ttgacgagtt | ctccccagtc | accagaacca | cctccgtcaa | catcaagtct | 420 |
| accaacgttg | agtcctccat | gttgttgaac | ttgttggttc | tgggtgctgg | tccagacatt | 480 |
| ttcgagtctt | gttgttaccc | agtcagaaag | ctgatcgacc | agacgttgt | ttacgaccca | 540 |
| tctaactacg | gtttcggttc | cattaacatc | gttaccttct | ctccagagta | cgagtacacc | 600 |
| ttcaacgaca | tctccggtgg | tcacaactcc | tccaccgagt | ctttcattgc | tgacccagcc | 660 |
| atctccctgg | ctcacgagct | gattcacgct | ttgcacggtt | tgtacggtgc | tagaggtgtc | 720 |
| acctacgagg | agaccattga | ggtcaagcaa | gccccattga | tgatcgccga | aagccaatc | 780 |
| agattggagg | agttcttgac | cttcggtggt | caggacttga | acatcatcac | tccgctatg | 840 |
| aaggagaaga | tctacaacaa | cctgctggcc | aactacgaga | gattgccac | cagattgtcc | 900 |
| gaggtcaact | ctgccccacc | agagtacgac | atcaacgagt | acaaggacta | cttccaatgg | 960 |
| aagtacggtt | tggacaagaa | cgccgacggt | tcctacaccg | tcaacgagaa | caagtccaac | 1020 |
| gagatttaca | agaagttgta | ctctttcacc | gagtccgacc | tggctaacaa | gttcaaggtt | 1080 |
| aagtgtagaa | acacctactt | catcaagtac | gagttcttga | aggttccaaa | cctgttggac | 1140 |
| gacgacatct | acaccgtttc | tgagggtttc | aacatcggta | cttggctgt | caacaacaga | 1200 |
| ggtcagtcca | ttaagctgaa | cccaaagatc | attgactccc | agacaaggg | tctggttgag | 1260 |
| aagattgtca | agttctgtaa | gtccgtcatc | ccaagaaagg | gtaccaag | | 1308 |

<210> SEQ ID NO 15
<211> LENGTH: 436
<212> TYPE: PRT
<213> ORGANISM: Artificial Sequence
<220> FEATURE:
<223> OTHER INFORMATION: Synthetic botulinum neurotoxin light chain of
      serotype F based on wild-type Clostridium
      botulinum sequence

<400> SEQUENCE: 15

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Glu Arg
            35                  40                  45

Asn Thr Ile Gly Thr Asn Pro Ser Asp Phe Asp Pro Ala Ser Leu
        50                  55                  60

Lys Asn Gly Ser Ser Ala Tyr Tyr Asp Pro Asn Tyr Leu Thr Thr Asp
65                  70                  75                  80

Ala Glu Lys Asp Arg Tyr Leu Lys Thr Thr Ile Lys Leu Phe Lys Arg
                85                  90                  95

```
Ile Asn Ser Asn Pro Ala Gly Lys Val Leu Leu Gln Glu Ile Ser Tyr
            100                 105                 110

Ala Lys Pro Tyr Leu Gly Asn Asp His Thr Pro Ile Asp Glu Phe Ser
        115                 120                 125

Pro Val Thr Arg Thr Thr Ser Val Asn Ile Lys Ser Thr Asn Val Glu
    130                 135                 140

Ser Ser Met Leu Leu Asn Leu Val Leu Gly Ala Gly Pro Asp Ile
145                 150                 155                 160

Phe Glu Ser Cys Cys Tyr Pro Val Arg Lys Leu Ile Asp Pro Asp Val
                165                 170                 175

Val Tyr Asp Pro Ser Asn Tyr Gly Phe Gly Ser Ile Asn Ile Val Thr
            180                 185                 190

Phe Ser Pro Glu Tyr Glu Tyr Thr Phe Asn Asp Ile Ser Gly Gly His
        195                 200                 205

Asn Ser Ser Thr Glu Ser Phe Ile Ala Asp Pro Ala Ile Ser Leu Ala
    210                 215                 220

His Glu Leu Ile His Ala Leu His Gly Leu Tyr Gly Ala Arg Gly Val
225                 230                 235                 240

Thr Tyr Glu Glu Thr Ile Glu Val Lys Gln Ala Pro Leu Met Ile Ala
                245                 250                 255

Glu Lys Pro Ile Arg Leu Glu Glu Phe Leu Thr Phe Gly Gly Gln Asp
            260                 265                 270

Leu Asn Ile Ile Thr Ser Ala Met Lys Glu Lys Ile Tyr Asn Asn Leu
        275                 280                 285

Leu Ala Asn Tyr Glu Lys Ile Ala Thr Arg Leu Ser Glu Val Asn Ser
    290                 295                 300

Ala Pro Pro Glu Tyr Asp Ile Asn Glu Tyr Lys Asp Tyr Phe Gln Trp
305                 310                 315                 320

Lys Tyr Gly Leu Asp Lys Asn Ala Asp Gly Ser Tyr Thr Val Asn Glu
                325                 330                 335

Asn Lys Ser Asn Glu Ile Tyr Lys Lys Leu Tyr Ser Phe Thr Glu Ser
            340                 345                 350

Asp Leu Ala Asn Lys Phe Lys Val Lys Cys Arg Asn Thr Tyr Phe Ile
        355                 360                 365

Lys Tyr Glu Phe Leu Lys Val Pro Asn Leu Leu Asp Asp Asp Ile Tyr
    370                 375                 380

Thr Val Ser Glu Gly Phe Asn Ile Gly Asn Leu Ala Val Asn Asn Arg
385                 390                 395                 400

Gly Gln Ser Ile Lys Leu Asn Pro Lys Ile Ile Asp Ser Pro Asp Lys
                405                 410                 415

Gly Leu Val Glu Lys Ile Val Lys Phe Cys Lys Ser Val Ile Pro Arg
            420                 425                 430

Lys Gly Thr Lys
        435

<210> SEQ ID NO 16
<211> LENGTH: 1317
<212> TYPE: DNA
<213> ORGANISM: Artificial Sequence
<220> FEATURE:
<223> OTHER INFORMATION: Synthetic botulinum neurotoxin light chain of
      serotype G based on wild-type Clostridium
      botulinum sequence

<400> SEQUENCE: 16
```

-continued

```
atgccagtca acatcaagaa cttcaactac aacgacccaa ttaacaacga cgacatcatg      60
atggagccat tcaacgaccc aggtccaggt acctactaca aggctttcag aatcattgac    120
agaatttgga tcgttccaga gagattcacc tacggtttcc aaccagacca gttcaacgcc    180
tccaccggtg tcttctctaa ggacgtctac gagtactacg acccaaccta cttgaagacc    240
gacgctgaga aggacaagtt cttgaagacc atgatcaagt tgttcaacag aattaactct    300
aagccatccg gtcaaagatt gttggacatg attgttgacg ctattccata cttgggtaac    360
gcctccaccc caccagacaa gttcgctgcc aacgtcgcta acgtttctat caacaagaag    420
attatccaac aggtgctga ggaccagatc aagggtttga tgaccaactt gattattttc     480
ggtccaggtc cagtcttgtc cgacaacttc accgactcta tgatcatgaa cggtcactcc    540
ccaatttccg ggtttcgg tgctagaatg atgatcagat ctgtccatc ctgtttgaac       600
gttttcaaca cgtccaaga gaacaaggac acctctatct tctctagaag agcttacttc    660
gctgacccga ctctgaccct gatgcacgag ttgatccacg tcttgcacgg tctgtacggt    720
attaagatct ccaacctgcc aattaccca acaccaagg agttcttcat gcaacactcc     780
gacccagttc aagccgagga gctgtacacc ttcggtggtc acgacccatc tgtttcccca    840
tctaccgaca tgaacattta caacaaggct ctgcagaact ccaagacat tgctaacaga     900
ctgaacatcg tctcctctgc caaggttct ggtatcgaca tttccttgta caagcaaatc     960
tacaagaaca gtacgactt cgtcgaggac ccaaacggta agtactctgt tgacaaggac   1020
aagttcgaca gctgtacaa ggctttgatg ttcggttta ccgagaccaa cttggccggt    1080
gagtacggta ttaagaccag atactcttac ttctctgagt acctgccacc aatcaagacc   1140
gagaagttgt tggacaacac catctacacc cagaacgagg gtttcaacat tgcttccaag   1200
aacttgaaga acgagttcaa cggtcagaac aaggccgtca acaaggaggc ctacgaggag   1260
atttccctgg agcacttggt catctacaga atcgctatgt gtaagccagt catgtac      1317
```

<210> SEQ ID NO 17
<211> LENGTH: 439
<212> TYPE: PRT
<213> ORGANISM: Artificial Sequence
<220> FEATURE:
<223> OTHER INFORMATION: Synthetic botulinum neurotoxin light chain of serotype G based on wild-type Clostridium botulinum sequence

<400> SEQUENCE: 17

```
Met Pro Val Asn Ile Lys Asn Phe Asn Tyr Asn Asp Pro Ile Asn Asn
  1               5                  10                  15

Asp Asp Ile Met Met Glu Pro Phe Asn Asp Pro Gly Pro Gly Thr Tyr
             20                  25                  30

Tyr Lys Ala Phe Arg Ile Ile Asp Arg Ile Trp Ile Val Pro Glu Arg
         35                  40                  45

Phe Thr Tyr Gly Phe Gln Pro Asp Gln Phe Asn Ala Ser Thr Gly Val
     50                  55                  60

Phe Ser Lys Asp Val Tyr Glu Tyr Tyr Asp Pro Thr Tyr Leu Lys Thr
 65                  70                  75                  80

Asp Ala Glu Lys Asp Lys Phe Leu Lys Thr Met Ile Lys Leu Phe Asn
                 85                  90                  95

Arg Ile Asn Ser Lys Pro Ser Gly Gln Arg Leu Leu Asp Met Ile Val
            100                 105                 110

Asp Ala Ile Pro Tyr Leu Gly Asn Ala Ser Thr Pro Pro Asp Lys Phe
        115                 120                 125
```

Ala Ala Asn Val Ala Asn Val Ser Ile Asn Lys Lys Ile Ile Gln Pro
            130                 135                 140

Gly Ala Glu Asp Gln Ile Lys Gly Leu Met Thr Asn Leu Ile Ile Phe
145                 150                 155                 160

Gly Pro Gly Pro Val Leu Ser Asp Asn Phe Thr Asp Ser Met Ile Met
                165                 170                 175

Asn Gly His Ser Pro Ile Ser Glu Gly Phe Gly Ala Arg Met Met Ile
            180                 185                 190

Arg Phe Cys Pro Ser Cys Leu Asn Val Phe Asn Asn Val Gln Glu Asn
        195                 200                 205

Lys Asp Thr Ser Ile Phe Ser Arg Arg Ala Tyr Phe Ala Asp Pro Ala
    210                 215                 220

Leu Thr Leu Met His Glu Leu Ile His Val Leu His Gly Leu Tyr Gly
225                 230                 235                 240

Ile Lys Ile Ser Asn Leu Pro Ile Thr Pro Asn Thr Lys Glu Phe Phe
                245                 250                 255

Met Gln His Ser Asp Pro Val Gln Ala Glu Glu Leu Tyr Thr Phe Gly
            260                 265                 270

Gly His Asp Pro Ser Val Ser Pro Ser Thr Asp Met Asn Ile Tyr Asn
        275                 280                 285

Lys Ala Leu Gln Asn Phe Gln Asp Ile Ala Asn Arg Leu Asn Ile Val
    290                 295                 300

Ser Ser Ala Gln Gly Ser Gly Ile Asp Ile Ser Leu Tyr Lys Gln Ile
305                 310                 315                 320

Tyr Lys Asn Lys Tyr Asp Phe Val Glu Asp Pro Asn Gly Lys Tyr Ser
                325                 330                 335

Val Asp Lys Asp Lys Phe Asp Lys Leu Tyr Lys Ala Leu Met Phe Gly
            340                 345                 350

Phe Thr Glu Thr Asn Leu Ala Gly Glu Tyr Gly Ile Lys Thr Arg Tyr
        355                 360                 365

Ser Tyr Phe Ser Glu Tyr Leu Pro Pro Ile Lys Thr Glu Lys Leu Leu
    370                 375                 380

Asp Asn Thr Ile Tyr Thr Gln Asn Glu Gly Phe Asn Ile Ala Ser Lys
385                 390                 395                 400

Asn Leu Lys Asn Glu Phe Asn Gly Gln Asn Lys Ala Val Asn Lys Glu
                405                 410                 415

Ala Tyr Glu Glu Ile Ser Leu Glu His Leu Val Ile Tyr Arg Ile Ala
            420                 425                 430

Met Cys Lys Pro Val Met Tyr
        435

<210> SEQ ID NO 18
<211> LENGTH: 1239
<212> TYPE: DNA
<213> ORGANISM: Artificial Sequence
<220> FEATURE:
<223> OTHER INFORMATION: Synthetic N-terminal region of the heavy chain
      of botulinum neurotoxin serotype A based on wild-type
      Clostridium botulinum sequence

<400> SEQUENCE: 18
atggctctga acgacctgtg catcaaagtt aacaactggg acctgttctt ctccccgtct      60
gaagacaact tcactaacga cctgaacaaa ggcgaagaaa tcacctccga cactaacatc     120
gaagctgctg aagaaaacat ctctctggac ctgatccagc agtactacct gacttttcaac    180

```
ttcgacaacg aaccggaaaa catctccatc gaaaacctgt cttccgacat catcggtcag    240
ctggaactga tgccgaacat cgaacgcttc ccgaacggca agaaatacga actggacaaa    300
tacaccatgt tccactacct gcgtgctcag gaattcgaac acggtaaatc tcgtatcgct    360
ctgactaact ccgttaacga agctctgctg aacccgtctc gcgtttacac cttcttctct    420
tccgactacg ttaagaaagt taacaaagct actgaagctg ctatgttcct gggttgggtt    480
gaacagctgg tttacgactt caccgacgaa acttctgaag tttccaccac tgacaaaatc    540
gctgacatca ctatcatcat cccgtacatc ggcccggctc tgaacatcgg taacatgctg    600
tacaaagaca cttcgttgg tgctctgatc ttctctggcg ctgttatcct gctggaattc    660
atcccggaaa tcgctatccc ggttctgggt accttcgctc tggtttccta catcgctaac    720
aaagttctga ctgttcagac catcgacaac gctctgtcta acgtaacga aaatgggac    780 gaagtttaca atacatcgt tactaactgg ctggctaaag ttaacactca gatcgacctg    840
atccgtaaga agatgaaaga agctctggaa accaggctg aagctactaa agctatcatc    900
aactaccagt acaaccagta caccgaagaa gaaaagaaca acatcaactt caacatcgat    960
gacctgtcct ctaaactgaa cgaatccatc aacaaagcta tgatcaacat caacaaattc   1020
ctgaaccagt gctctgtttc ctacctgatg aactctatga tcccgtacgg cgttaaacgc   1080
ctggaagact cgacgcttc cctgaaagac gctctgctga aatacatccg tgacaactac   1140
ggtactctga tcggccaggt tgaccgtctg aaagacaagg ttaacaacac cctgtctact   1200
gacatcccgt tccagctgtc caaatacgtt gacaaccag                          1239

<210> SEQ ID NO 19
<211> LENGTH: 413
<212> TYPE: PRT
<213> ORGANISM: Artificial Sequence
<220> FEATURE:
<223> OTHER INFORMATION: Synthetic N-terminal region of the heavy chain
      of botulinum neurotoxin serotype A based on wild-type
      Clostridium botulinum sequence

<400> SEQUENCE: 19

Met Ala Leu Asn Asp Leu Cys Ile Lys Val Asn Asn Trp Asp Leu Phe
 1               5                  10                  15

Phe Ser Pro Ser Glu Asp Asn Phe Thr Asn Asp Leu Asn Lys Gly Glu
                20                  25                  30

Glu Ile Thr Ser Asp Thr Asn Ile Glu Ala Ala Glu Glu Asn Ile Ser
            35                  40                  45

Leu Asp Leu Ile Gln Gln Tyr Tyr Leu Thr Phe Asn Phe Asp Asn Glu
     50                  55                  60

Pro Glu Asn Ile Ser Ile Glu Asn Leu Ser Ser Asp Ile Ile Gly Gln
65                  70                  75                  80

Leu Glu Leu Met Pro Asn Ile Glu Arg Phe Pro Asn Gly Lys Lys Tyr
                85                  90                  95

Glu Leu Asp Lys Tyr Thr Met Phe His Tyr Leu Arg Ala Gln Glu Phe
            100                 105                 110

Glu His Gly Lys Ser Arg Ile Ala Leu Thr Asn Ser Val Asn Glu Ala
        115                 120                 125

Leu Leu Asn Pro Ser Arg Val Tyr Thr Phe Phe Ser Ser Asp Tyr Val
    130                 135                 140

Lys Lys Val Asn Lys Ala Thr Glu Ala Ala Met Phe Leu Gly Trp Val
145                 150                 155                 160

Glu Gln Leu Val Tyr Asp Phe Thr Asp Glu Thr Ser Glu Val Ser Thr
```

```
                  165                 170                 175
Thr Asp Lys Ile Ala Asp Ile Thr Ile Ile Pro Tyr Ile Gly Pro
                180                 185                 190

Ala Leu Asn Ile Gly Asn Met Leu Tyr Lys Asp Asp Phe Val Gly Ala
            195                 200                 205

Leu Ile Phe Ser Gly Ala Val Ile Leu Glu Phe Ile Pro Glu Ile
        210                 215                 220

Ala Ile Pro Val Leu Gly Thr Phe Ala Leu Val Ser Tyr Ile Ala Asn
225                 230                 235                 240

Lys Val Leu Thr Val Gln Thr Ile Asp Asn Ala Leu Ser Lys Arg Asn
                245                 250                 255

Glu Lys Trp Asp Glu Val Tyr Lys Tyr Ile Val Thr Asn Trp Leu Ala
            260                 265                 270

Lys Val Asn Thr Gln Ile Asp Leu Ile Arg Lys Lys Met Lys Glu Ala
                275                 280                 285

Leu Glu Asn Gln Ala Glu Ala Thr Lys Ala Ile Ile Asn Tyr Gln Tyr
        290                 295                 300

Asn Gln Tyr Thr Glu Glu Glu Lys Asn Asn Ile Asn Phe Asn Ile Asp
305                 310                 315                 320

Asp Leu Ser Ser Lys Leu Asn Glu Ser Ile Asn Lys Ala Met Ile Asn
                325                 330                 335

Ile Asn Lys Phe Leu Asn Gln Cys Ser Val Ser Tyr Leu Met Asn Ser
            340                 345                 350

Met Ile Pro Tyr Gly Val Lys Arg Leu Glu Asp Phe Asp Ala Ser Leu
        355                 360                 365

Lys Asp Ala Leu Leu Lys Tyr Ile Arg Asp Asn Tyr Gly Thr Leu Ile
    370                 375                 380

Gly Gln Val Asp Arg Leu Lys Asp Lys Val Asn Asn Thr Leu Ser Thr
385                 390                 395                 400

Asp Ile Pro Phe Gln Leu Ser Lys Tyr Val Asp Asn Gln
                405                 410
```

<210> SEQ ID NO 20
<211> LENGTH: 2583
<212> TYPE: DNA
<213> ORGANISM: Artificial Sequence
<220> FEATURE:
<223> OTHER INFORMATION: Synthetic polynucleotide sequence for the light chain with Hn of C. botulinum Type A.

<400> SEQUENCE: 20

```
atggttcagt tcgttaacaa acagttcaac tacaaagacc cggttaacgg tgttgacatc      60
gcttacatca aaatcccgaa cgttggtcag atgcagccgg ttaaagcatt caaaatccac     120
aacaaaatct gggttatccc ggaacgtgac actttcacta acccggaaga aggtgacctg     180
aacccgccgc cggaagctaa acaggttccg gtttcttact acgactctac ttacctgtct     240
actgacaacg aaaaggacaa ctacctgaaa ggtgttacta actgtttga cgtatctac      300 tctactgacc tgggtcgcat gctgctcact tctatcgttc gtggtatccc gttctggggt     360
ggttctacta tcgacactga actgaaagtt atcgacacta actgcatcaa cgttatccag     420
ccggacggtt cttaccgttc tgaagaactg aacctggtta tcatcggtcc gtctgctgac     480
atcatccagt ttgaatgcaa atctttcggt cacgaagttc tgaacctgac tcgtaacggt     540
tacggttcta tcagtacat ccgtttctct ccggacttca ctttcggttt cgaagaatct     600
ctggaagttg acactaaccc gctgctgggt gctggtaaat tcgctactga cccggctgtt     660
```

-continued

```
actctggctc acgaactgat ccacgctggt caccgtctgt acggtatcgc tatcaacccg      720
aaccgtgttt tcaaagttaa cactaacgct tactacgaaa tgtctggtct ggaagtttct      780
tttgaagaac tgcgtacttt cggtggtcac gacgctaaat tcatcgactc tctgcaggaa      840
aacgagttcc gtctgtacta ctactacaaa ttcaaagaca tcgcttctac tctgaacaaa      900
gctaaatcta tcgttggtac cactgcttct ctgcagtaca tgaagaacgt tttcaaagaa      960
aagtacctgc tgtctgaaga cacttctggt aaattctctg ttgacaaact gaaattcgac     1020
aaactgtaca aaatgctgac tgaaatctac actgaagaca cttcgttaa  attcttcaaa     1080 gttctgaacc gtaaaactta cctgaacttc gacaaagctg ttttcaaaat caacatcgtt     1140
ccgaaagtta actacactat ctcgacggt  ttcaacctgc gtaacactaa cctggctgct     1200
aacttcaacg gtcagaacac tgaaatcaac aacatgaact tcactaaact gaagaacttc     1260
actggtctgt ttgagttcta caaactgctg tgcgttcgtg gtatcatcac ttctaaaact     1320
aaatctctgg acaaaggtta acaaagct ctgaacgacc tgtgcatcaa agttaacaac      1380
tgggacctgt tcttctcccc gtctgaagac aacttcacta cgacctgaa  caaaggcgaa     1440 gaaatcacct ccgacactaa catcgaagct gctgaagaaa acatctctct ggacctgatc     1500
cagcagtact acctgacttt caacttcgac aacgaaccgg aaaacatctc catcgaaaac     1560
ctgtcttccg acatcatcgg tcagctggaa ctgatgccga catcgaacg  cttcccgaac     1620 ggcaagaaat acgaactgga caaatacacc atgttccact acctgcgtgc tcaggaattc     1680
gaacacggta atctcgtat  cgctctgact aactccgtta cgaagctct  gctgaacccg     1740 tctcgcgttt acaccttctt ctcttccgac tacgttaaga agttaacaa  agctactgaa     1800 gctgctatgt tcctgggttg ggttaacag ctggtttacg acttcaccga cgaaacttct     1860
gaagtttcca ccactgacaa aatcgctgac atcactatca tcatcccgta catcggcccg     1920
gctctgaaca tcgtaacat gctgtacaaa gacgacttcg ttggtgctct gatcttctct     1980
ggcgctgtta tcctgctgga attcatcccg gaaatcgcta tcccggttct gggtaccttc     2040
gctctggttt cctacatcgc taacaaagtt ctgactgttc agaccatcga caacgctctg     2100
tctaaacgta acgaaaaatg ggacgaagtt tacaaataca tcgttactaa ctggctggct     2160
aaagttaaca ctcagatcga cctgatccgt aagaagatga agaagctct  ggaaaaccag     2220 gctgaagcta ctaaagctat catcaactac cagtacaacc agtacaccga agaagaaaag     2280
aacaacatca cttcaacat  cgatgacctg tcctctaaac tgaacgaatc catcaacaaa     2340
gctatgatca acatcaacaa attcctgaac cagtgctctg tttcctacct gatgaactct     2400
atgatcccgt acggcgttaa acgcctggaa gacttcgacg cttccctgaa agacgctctg     2460
ctgaaataca tccgtgacaa ctacggtact ctgatcggcc aggttgaccg tctgaaagac     2520
aaggttaaca cacccctgtc tactgacatc ccgttccagc tgtccaaata cgttgacaac     2580
cag                                                                  2583
```

<210> SEQ ID NO 21
<211> LENGTH: 861
<212> TYPE: PRT
<213> ORGANISM: Artificial Sequence
<220> FEATURE:
<223> OTHER INFORMATION: Recombinant protein encoded by SEQ ID NO:20

<400> SEQUENCE: 21

Met Val Gln Phe Val Asn Lys Gln Phe Asn Tyr Lys Asp Pro Val Asn
 1               5                  10                  15

-continued

```
Gly Val Asp Ile Ala Tyr Ile Lys Ile Pro Asn Val Gly Gln Met Gln
             20                  25                  30
Pro Val Lys Ala Phe Lys Ile His Asn Lys Ile Trp Val Ile Pro Glu
             35                  40                  45
Arg Asp Thr Phe Thr Asn Pro Glu Glu Gly Asp Leu Asn Pro Pro Pro
         50                  55                  60
Glu Ala Lys Gln Val Pro Val Ser Tyr Tyr Asp Ser Thr Tyr Leu Ser
 65                  70                  75                  80
Thr Asp Asn Glu Lys Asp Asn Tyr Leu Lys Gly Val Thr Lys Leu Phe
                 85                  90                  95
Glu Arg Ile Tyr Ser Thr Asp Leu Gly Arg Met Leu Leu Thr Ser Ile
             100                 105                 110
Val Arg Gly Ile Pro Phe Trp Gly Gly Ser Thr Ile Asp Thr Glu Leu
             115                 120                 125
Lys Val Ile Asp Thr Asn Cys Ile Asn Val Ile Gln Pro Asp Gly Ser
 130                 135                 140
Tyr Arg Ser Glu Glu Leu Asn Leu Val Ile Ile Gly Pro Ser Ala Asp
 145                 150                 155                 160
Ile Ile Gln Phe Glu Cys Lys Ser Phe Gly His Glu Val Leu Asn Leu
             165                 170                 175
Thr Arg Asn Gly Tyr Gly Ser Thr Gln Tyr Ile Arg Phe Ser Pro Asp
             180                 185                 190
Phe Thr Phe Gly Phe Glu Glu Ser Leu Glu Val Asp Thr Asn Pro Leu
             195                 200                 205
Leu Gly Ala Gly Lys Phe Ala Thr Asp Pro Ala Val Thr Leu Ala His
 210                 215                 220
Glu Leu Ile His Ala Gly His Arg Leu Tyr Gly Ile Ala Ile Asn Pro
 225                 230                 235                 240
Asn Arg Val Phe Lys Val Asn Thr Asn Ala Tyr Tyr Glu Met Ser Gly
             245                 250                 255
Leu Glu Val Ser Phe Glu Glu Leu Arg Thr Phe Gly Gly His Asp Ala
             260                 265                 270
Lys Phe Ile Asp Ser Leu Gln Glu Asn Glu Phe Arg Leu Tyr Tyr Tyr
             275                 280                 285
Tyr Lys Phe Lys Asp Ile Ala Ser Thr Leu Asn Lys Ala Lys Ser Ile
 290                 295                 300
Val Gly Thr Thr Ala Ser Leu Gln Tyr Met Lys Asn Val Phe Lys Glu
 305                 310                 315                 320
Lys Tyr Leu Leu Ser Glu Asp Thr Ser Gly Lys Phe Ser Val Asp Lys
             325                 330                 335
Leu Lys Phe Asp Lys Leu Tyr Lys Met Leu Thr Glu Ile Tyr Thr Glu
             340                 345                 350
Asp Asn Phe Val Lys Phe Phe Lys Val Leu Asn Arg Lys Thr Tyr Leu
             355                 360                 365
Asn Phe Asp Lys Ala Val Phe Lys Ile Asn Ile Val Pro Lys Val Asn
             370                 375                 380
Tyr Thr Ile Tyr Asp Gly Phe Asn Leu Arg Asn Thr Asn Leu Ala Ala
 385                 390                 395                 400
Asn Phe Asn Gly Gln Asn Thr Glu Ile Asn Asn Met Asn Phe Thr Lys
             405                 410                 415
Leu Lys Asn Phe Thr Gly Leu Phe Glu Phe Tyr Lys Leu Leu Cys Val
             420                 425                 430
```

-continued

```
Arg Gly Ile Ile Thr Ser Lys Thr Lys Ser Leu Asp Lys Gly Tyr Asn
        435                 440                 445

Lys Ala Leu Asn Asp Leu Cys Ile Lys Val Asn Asn Trp Asp Leu Phe
    450                 455                 460

Phe Ser Pro Ser Glu Asp Asn Phe Thr Asn Asp Leu Asn Lys Gly Glu
465                 470                 475                 480

Glu Ile Thr Ser Asp Thr Asn Ile Glu Ala Ala Glu Glu Asn Ile Ser
                485                 490                 495

Leu Asp Leu Ile Gln Gln Tyr Tyr Leu Thr Phe Asn Phe Asp Asn Glu
            500                 505                 510

Pro Glu Asn Ile Ser Ile Glu Asn Leu Ser Ser Asp Ile Ile Gly Gln
        515                 520                 525

Leu Glu Leu Met Pro Asn Ile Glu Arg Phe Pro Asn Gly Lys Lys Tyr
    530                 535                 540

Glu Leu Asp Lys Tyr Thr Met Phe His Tyr Leu Arg Ala Gln Glu Phe
545                 550                 555                 560

Glu His Gly Lys Ser Arg Ile Ala Leu Thr Asn Ser Val Asn Glu Ala
                565                 570                 575

Leu Leu Asn Pro Ser Arg Val Tyr Thr Phe Phe Ser Ser Asp Tyr Val
            580                 585                 590

Lys Lys Val Asn Lys Ala Thr Glu Ala Ala Met Phe Leu Gly Trp Val
        595                 600                 605

Glu Gln Leu Val Tyr Asp Phe Thr Asp Glu Thr Ser Glu Val Ser Thr
    610                 615                 620

Thr Asp Lys Ile Ala Asp Ile Thr Ile Ile Pro Tyr Ile Gly Pro
625                 630                 635                 640

Ala Leu Asn Ile Gly Asn Met Leu Tyr Lys Asp Asp Phe Val Gly Ala
                645                 650                 655

Leu Ile Phe Ser Gly Ala Val Ile Leu Leu Glu Phe Ile Pro Glu Ile
            660                 665                 670

Ala Ile Pro Val Leu Gly Thr Phe Ala Leu Val Ser Tyr Ile Ala Asn
        675                 680                 685

Lys Val Leu Thr Val Gln Thr Ile Asp Asn Ala Leu Ser Lys Arg Asn
    690                 695                 700

Glu Lys Trp Asp Glu Val Tyr Lys Tyr Ile Val Thr Asn Trp Leu Ala
705                 710                 715                 720

Lys Val Asn Thr Gln Ile Asp Leu Ile Arg Lys Met Lys Glu Ala
                725                 730                 735

Leu Glu Asn Gln Ala Glu Ala Thr Lys Ala Ile Ile Asn Tyr Gln Tyr
            740                 745                 750

Asn Gln Tyr Thr Glu Glu Lys Asn Asn Ile Asn Phe Asn Ile Asp
        755                 760                 765

Asp Leu Ser Ser Lys Leu Asn Glu Ser Ile Asn Lys Ala Met Ile Asn
770                 775                 780

Ile Asn Lys Phe Leu Asn Gln Cys Ser Val Ser Tyr Leu Met Asn Ser
785                 790                 795                 800

Met Ile Pro Tyr Gly Val Lys Arg Leu Glu Asp Phe Asp Ala Ser Leu
                805                 810                 815

Lys Asp Ala Leu Leu Lys Tyr Ile Arg Asp Asn Tyr Gly Thr Leu Ile
            820                 825                 830

Gly Gln Val Asp Arg Leu Lys Asp Lys Val Asn Asn Thr Leu Ser Thr
        835                 840                 845

Asp Ile Pro Phe Gln Leu Ser Lys Tyr Val Asp Asn Gln
```

-continued

```
                  850              855              860
```

<210> SEQ ID NO 22
<211> LENGTH: 1329
<212> TYPE: DNA
<213> ORGANISM: Artificial Sequence
<220> FEATURE:
<223> OTHER INFORMATION: Synthetic polynucleotide sequence for the
      light chain of C. botulinum Type B,
      optimized for expression in E. coli.

<400> SEQUENCE: 22

```
atgccagtta ccatcaacaa cttcaactac aacgacccaa tcgacaacaa caacatcatt    60
atgatggagc caccattcgc tagaggtacc ggtagatact acaaggcttt caagatcacc   120
gacagaattt ggattattcc agagagatac actttcggtt acaagccaga ggacttcaac   180
aagtcttctg gtattttcaa cagagacgtc tgcgagtact acgacccaga ctacctgaac   240
accaacgaca gaagaacat cttcctgcag accatgatca gctgttcaa cagaatcaag   300
tccaagccat gggtgagaa gctgctggag atgatcatta cggtatccc atacctgggt   360
gacagaagag tcccactgga ggagttcaac accaacatcg cctccgtcac cgtcaacaag   420
ctgatctcca acccgggtga ggtcgagcgt aagaagggca tcttcgccaa cctgatcatc   480
ttcggcccag gtccagtctt gaacgagaac gagactattg acattggcat tcaaaaccac   540
ttcgcctcca gagagggttt cggcggtatc atgcaaatga gttctgtcc agagtacgtc   600
tccgttttca caacgtcca agagaacaag ggtgcctcca tcttcaacag aagaggctac   660
ttctccgacc cagccttgat cttgatgcac gagttgatcc acgtcttgca cggtttgtac   720
ggtatcaagg tcgacgactt gccaattgtc ccaaacgaga agaagttctt catgcagtcc   780
accgacgcca tccaggccga ggagctgtac accttcggtg gtcaggaccc atccatcatt   840
accccatcca ccgacaagtc catctacgac aaggtcttgc agaacttcag aggtatcgtc   900
gatagactga acaaggtctt ggtctgcatc tccgacccaa acatcaacat caacatttac   960
aagaacaagt tcaaggacaa gtacaagttc gtcgaggact ccgagggtaa gtactccatc  1020
gacgtcgagt ccttcgacaa gctgtacaag tccctgatgt tcggtttcac cgagaccaac  1080
atcgccgaga actacaagat caagaccaga gcctcctact ctccgactc cctgccacca  1140
gtcaagatca gaacttgtt ggacaacgaa atctacacta ttgaggaggg tttcaacatt  1200
tccgacaagg catggagaa ggagtacaga ggtcaaaaca aggctattaa caagcaagct  1260
tacgaggaga tttctaagga gcacttggct gtttacaaga ttcaaatgtg taagtctgtt  1320
aagtaatag                                                            1329
```

<210> SEQ ID NO 23
<211> LENGTH: 441
<212> TYPE: PRT
<213> ORGANISM: Artificial Sequence
<220> FEATURE:
<223> OTHER INFORMATION: Recombinant protein encoded by SEQ ID NO:22

<400> SEQUENCE: 23

```
Met Pro Val Thr Ile Asn Asn Phe Asn Tyr Asn Asp Pro Ile Asp Asn
  1               5                  10                  15

Asn Asn Ile Ile Met Met Glu Pro Pro Phe Ala Arg Gly Thr Gly Arg
             20                  25                  30

Tyr Tyr Lys Ala Phe Lys Ile Thr Asp Arg Ile Trp Ile Ile Pro Glu
         35                  40                  45
```

```
Arg Tyr Thr Phe Gly Tyr Lys Pro Glu Asp Phe Asn Lys Ser Ser Gly
 50                  55                  60

Ile Phe Asn Arg Asp Val Cys Glu Tyr Tyr Asp Pro Asp Tyr Leu Asn
 65                  70                  75                  80

Thr Asn Asp Lys Lys Asn Ile Phe Leu Gln Thr Met Ile Lys Leu Phe
                 85                  90                  95

Asn Arg Ile Lys Ser Lys Pro Leu Gly Glu Lys Leu Leu Glu Met Ile
                100                 105                 110

Ile Asn Gly Ile Pro Tyr Leu Gly Asp Arg Arg Val Pro Leu Glu Glu
                115                 120                 125

Phe Asn Thr Asn Ile Ala Ser Val Thr Val Asn Lys Leu Ile Ser Asn
                130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Ile Met Gln
                180                 185                 190

Met Lys Phe Cys Pro Glu Tyr Val Ser Val Phe Asn Asn Val Gln Glu
                195                 200                 205

Asn Lys Gly Ala Ser Ile Phe Asn Arg Arg Gly Tyr Phe Ser Asp Pro
                210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
                260                 265                 270

Gly Gly Gln Asp Pro Ser Ile Ile Thr Pro Ser Thr Asp Lys Ser Ile
                275                 280                 285

Tyr Asp Lys Val Leu Gln Asn Phe Arg Gly Ile Val Asp Arg Leu Asn
                290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
                340                 345                 350

Met Phe Gly Phe Thr Glu Thr Asn Ile Ala Glu Asn Tyr Lys Ile Lys
                355                 360                 365

Thr Arg Ala Ser Tyr Phe Ser Asp Ser Leu Pro Pro Val Lys Ile Lys
                370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
                420                 425                 430

Lys Ile Gln Met Cys Lys Ser Val Lys
                435                 440

<210> SEQ ID NO 24
<211> LENGTH: 2559
<212> TYPE: DNA
```

<213> ORGANISM: Artificial Sequence
<220> FEATURE:
<223> OTHER INFORMATION: Synthetic polynucleotide sequence for the
     light chain with Hn segment of of C.
     botulinum Type B, optimized for expression
     in E. coli.

<400> SEQUENCE: 24

| | | | | |
|---|---|---|---|---|
| atgccagtta | ccatcaacaa | cttcaactac | aacgacccaa | tcgacaacaa caacatcatt | 60 |
| atgatggagc | caccattcgc | tagaggtacc | ggtagatact | acaaggcttt caagatcacc | 120 |
| gacagaattt | ggattattcc | agagagatac | actttcggtt | acaagccaga ggacttcaac | 180 |
| aagtcttctg | gtattttcaa | cagagacgtc | tgcgagtact | acgacccaga ctacctgaac | 240 |
| accaacgaca | gaagaacat | cttcctgcag | accatgatca | agctgttcaa cagaatcaag | 300 |
| tccaagccat | tgggtgagaa | gctgctggag | atgatcatta | acggtatccc ataccctggt | 360 |
| gacagaagag | tcccactgga | ggagttcaac | accaacatcg | cctccgtcac cgtcaacaag | 420 |
| ctgatctcca | acccgggtga | ggtcgagcgt | aagaagggca | tcttcgccaa cctgatcatc | 480 |
| ttcggcccag | tccagtctt | gaacgagaac | gagactattg | acattggcat tcaaaaccac | 540 |
| ttcgcctcca | gagagggttt | cggcggtatc | atgcaaatga | agttctgtcc agagtacgtc | 600 |
| tccgttttca | caacgtcca | agagaacaag | ggtgcctcca | tcttcaacag aagaggctac | 660 |
| ttctccgacc | cagccttgat | cttgatgcac | gagttgatcc | acgtcttgca cggtttgtac | 720 |
| ggtatcaagg | tcgacgactt | gccaattgtc | ccaaacgaga | gaagttctt catgcagtcc | 780 |
| accgacgcca | tccaggccga | ggagctgtac | accttcggtg | gtcaggaccc atccatcatt | 840 |
| accccatcca | ccgacaagtc | catctacgac | aaggtcttgc | agaacttcag aggtatcgtc | 900 |
| gatagactga | caaggtcttg | gtctgcatc | tccgacccaa | acatcaacat caacatttac | 960 |
| aagaacaagt | tcaaggacaa | gtacaagttc | gtcgaggact | ccgagggtaa gtactccatc | 1020 |
| gacgtcgagt | ccttcgacaa | gctgtacaag | tccctgatgt | tcggtttcac cgagaccaac | 1080 |
| atcgccgaga | actacaagat | caagaccaga | gcctcctact | ctccgactc cctgccacca | 1140 |
| gtcaagatca | gaacttgtt | ggacaacgaa | atctacacta | ttgaggaggg tttcaacatt | 1200 |
| tccgacaagg | acatggagaa | ggagtacaga | ggtcaaaaca | aggctattaa caagcaagct | 1260 |
| tacgaggaga | tttctaagga | gcacttggct | gtttacaaga | ttcaaatgtg taagtctgtt | 1320 |
| aaggctccag | gaatctgtat | cgacgtcgac | aacgaggact | gttcttcat cgctgacaag | 1380 |
| aactccttct | ccgacgactt | gtccaagaac | gagagaatcg | agtacaacac ccagtccaac | 1440 |
| tacatcgaga | acgacttccc | aatcaacgag | ttgatcttgg | acaccgactt gatctccaag | 1500 |
| atcgagttgc | catccgagaa | caccgagtcc | ttgactgact | caacgtcga cgtcccagtc | 1560 |
| tacgagaagc | aaccagctat | caagaagatt | ttcaccgacg | agaacaccat cttccaatac | 1620 |
| ctgtactctc | agaccttccc | tttggacatc | agagacatct | ccttgacctc ttccttcgac | 1680 |
| gacgccctgc | tgttctccaa | caaggtctac | tccttcttct | ccatggacta catcaagact | 1740 |
| gctaacaagg | tcgtcgaggc | cggtttgttc | gctggttggg | tcaagcagat cgtcaacgat | 1800 |
| ttcgtcatcg | aggctaacaa | gtccaacacc | atggacaaga | ttgccgacat ctccttgatt | 1860 |
| gtcccataca | tcggtttggc | cttgaacgtc | ggtaacgaga | ccgccaaggg taacttcgag | 1920 |
| aacgctttcg | agatcgctgg | tgcctccatc | ttgttggagt | tcatcccaga gttgttgatc | 1980 |
| ccagtcgtcg | gtgccttctt | gttggagtcc | tacatcgaca | caagaacaa gatcatcaag | 2040 |
| accatcgaca | acgctttgac | caagagaaac | gagaagtggt | ccgacatgta cggtttgatc | 2100 |

-continued

```
gtcgcccaat ggttgtccac cgtcaacacc caattctaca ccatcaagga gggtatgtac    2160
aaggccttga actaccagge ccaagctttg gaggagatca tcaagtacag atacaacatc    2220
tactccgaga aggagaagtc caacattaac atcgacttca cgacatcaa ctccaagctg    2280 aacgaggta ttaaccaggc catcgacaac atcaacaact tcatcaacgg ttgttccgtc    2340
tcctacttga tgaagaagat gattccattg gccgtcgaga agttgttgga cttcgacaac    2400
accctgaaga agaacttgtt gaactacatc gacgagaaca agttgtactt gatcggttcc    2460
gctgagtacg agaagtccaa ggtcaacaag tacttgaaga ccatcatgcc attcgacttg    2520
tccatctaca ccaacgacac catcttgatc gagatgttc                          2559
```

<210> SEQ ID NO 25
<211> LENGTH: 852
<212> TYPE: PRT
<213> ORGANISM: Artificial Sequence
<220> FEATURE:
<223> OTHER INFORMATION: Recombinant protein encoded by SEQ ID NO:24

<400> SEQUENCE: 25

```
Pro Val Thr Ile Asn Asn Phe Asn Tyr Asn Asp Pro Ile Asp Asn Asn
  1               5                  10                  15

Asn Ile Ile Met Met Glu Pro Pro Phe Ala Arg Gly Thr Gly Arg Tyr
                 20                  25                  30

Tyr Lys Ala Phe Lys Ile Thr Asp Arg Ile Trp Ile Ile Pro Glu Arg
             35                  40                  45

Tyr Thr Phe Gly Tyr Lys Pro Glu Asp Phe Asn Lys Ser Ser Gly Ile
         50                  55                  60

Phe Asn Arg Asp Val Cys Glu Tyr Tyr Asp Pro Asp Tyr Leu Asn Thr
 65                  70                  75                  80

Asn Asp Lys Lys Asn Ile Phe Leu Gln Thr Met Ile Lys Leu Phe Asn
                 85                  90                  95

Arg Ile Lys Ser Lys Pro Leu Gly Glu Lys Leu Leu Glu Met Ile Ile
            100                 105                 110

Asn Gly Ile Pro Tyr Leu Gly Asp Arg Arg Val Pro Leu Glu Glu Phe
        115                 120                 125

Asn Thr Asn Ile Ala Ser Val Thr Val Asn Lys Leu Ile Ser Asn Pro
    130                 135                 140

Gly Glu Val Glu Arg Lys Lys Gly Ile Phe Ala Asn Leu Ile Ile Phe
145                 150                 155                 160

Gly Pro Gly Pro Val Leu Asn Glu Asn Glu Thr Ile Asp Ile Gly Ile
                165                 170                 175

Gln Asn His Phe Ala Ser Arg Glu Gly Phe Gly Gly Ile Met Gln Met
            180                 185                 190

Lys Phe Cys Pro Glu Tyr Val Ser Val Phe Asn Asn Val Gln Glu Asn
        195                 200                 205

Lys Gly Ala Ser Ile Phe Asn Arg Arg Gly Tyr Phe Ser Asp Pro Ala
    210                 215                 220

Leu Ile Leu Met His Glu Leu Ile His Val Leu His Gly Leu Tyr Gly
225                 230                 235                 240

Ile Lys Val Asp Asp Leu Pro Ile Val Pro Asn Glu Lys Lys Phe Phe
                245                 250                 255

Met Gln Ser Thr Asp Ala Ile Gln Ala Glu Glu Leu Tyr Thr Phe Gly
            260                 265                 270

Gly Gln Asp Pro Ser Ile Ile Thr Pro Ser Thr Asp Lys Ser Ile Tyr
        275                 280                 285
```

```
Asp Lys Val Leu Gln Asn Phe Arg Gly Ile Val Asp Arg Leu Asn Lys
    290                 295                 300

Val Leu Val Cys Ile Ser Asp Pro Asn Ile Asn Ile Asn Ile Tyr Lys
305                 310                 315                 320

Asn Lys Phe Lys Asp Lys Tyr Lys Phe Val Glu Asp Ser Glu Gly Lys
                325                 330                 335

Tyr Ser Ile Asp Val Glu Ser Phe Asp Lys Leu Tyr Lys Ser Leu Met
                340                 345                 350

Phe Gly Phe Thr Glu Thr Asn Ile Ala Glu Asn Tyr Lys Ile Lys Thr
            355                 360                 365

Arg Ala Ser Tyr Phe Ser Asp Ser Leu Pro Val Lys Ile Lys Asn
    370                 375                 380

Leu Leu Asp Asn Glu Ile Tyr Thr Ile Glu Glu Gly Phe Asn Ile Ser
385                 390                 395                 400

Asp Lys Asp Met Glu Lys Glu Tyr Arg Gly Gln Asn Lys Ala Ile Asn
                405                 410                 415

Lys Gln Ala Tyr Glu Glu Ile Ser Lys Glu His Leu Ala Val Tyr Lys
                420                 425                 430

Ile Gln Met Cys Lys Ser Val Lys Ala Pro Gly Ile Cys Ile Asp Val
            435                 440                 445

Asp Asn Glu Asp Leu Phe Phe Ile Ala Asp Lys Asn Ser Phe Ser Asp
    450                 455                 460

Asp Leu Ser Lys Asn Glu Arg Ile Glu Tyr Asn Thr Gln Ser Asn Tyr
465                 470                 475                 480

Ile Glu Asn Asp Phe Pro Ile Asn Glu Leu Ile Leu Asp Thr Asp Leu
                485                 490                 495

Ile Ser Lys Ile Glu Leu Pro Ser Glu Asn Thr Glu Ser Leu Thr Asp
            500                 505                 510

Phe Asn Val Asp Val Pro Val Tyr Glu Lys Gln Pro Ala Ile Lys Lys
    515                 520                 525

Ile Phe Thr Asp Glu Asn Thr Ile Phe Gln Tyr Leu Tyr Ser Gln Thr
    530                 535                 540

Phe Pro Leu Asp Ile Arg Asp Ile Ser Leu Thr Ser Ser Phe Asp Asp
545                 550                 555                 560

Ala Leu Leu Phe Ser Asn Lys Val Tyr Ser Phe Ser Met Asp Tyr
                565                 570                 575

Ile Lys Thr Ala Asn Lys Val Val Glu Ala Gly Leu Phe Ala Gly Trp
            580                 585                 590

Val Lys Gln Ile Val Asn Asp Phe Val Ile Glu Ala Asn Lys Ser Asn
            595                 600                 605

Thr Met Asp Lys Ile Ala Asp Ile Ser Leu Ile Val Pro Tyr Ile Gly
    610                 615                 620

Leu Ala Leu Asn Val Gly Asn Glu Thr Ala Lys Gly Asn Phe Glu Asn
625                 630                 635                 640

Ala Phe Glu Ile Ala Gly Ala Ser Ile Leu Leu Glu Phe Ile Pro Glu
                645                 650                 655

Leu Leu Ile Pro Val Val Gly Ala Phe Leu Leu Glu Ser Tyr Ile Asp
                660                 665                 670

Asn Lys Asn Lys Ile Ile Lys Thr Ile Asp Asn Ala Leu Thr Lys Arg
                675                 680                 685

Asn Glu Lys Trp Ser Asp Met Tyr Gly Leu Ile Val Ala Gln Trp Leu
    690                 695                 700
```

-continued

```
Ser Thr Val Asn Thr Gln Phe Tyr Thr Ile Lys Glu Gly Met Tyr Lys
705                 710                 715                 720

Ala Leu Asn Tyr Gln Ala Gln Ala Leu Glu Glu Ile Ile Lys Tyr Arg
            725                 730                 735

Tyr Asn Ile Tyr Ser Glu Lys Glu Lys Ser Asn Ile Asn Ile Asp Phe
        740                 745                 750

Asn Asp Ile Asn Ser Lys Leu Asn Glu Gly Ile Asn Gln Ala Ile Asp
    755                 760                 765

Asn Ile Asn Asn Phe Ile Asn Gly Cys Ser Val Ser Tyr Leu Met Lys
770                 775                 780

Lys Met Ile Pro Leu Ala Val Glu Lys Leu Leu Asp Phe Asp Asn Thr
785                 790                 795                 800

Leu Lys Lys Asn Leu Leu Asn Tyr Ile Asp Glu Asn Lys Leu Tyr Leu
            805                 810                 815

Ile Gly Ser Ala Glu Tyr Glu Lys Ser Lys Val Asn Lys Tyr Leu Lys
        820                 825                 830

Thr Ile Met Pro Phe Asp Leu Ser Ile Tyr Thr Asn Asp Thr Ile Leu
    835                 840                 845

Ile Glu Met Phe
    850
```

<210> SEQ ID NO 26
<211> LENGTH: 1311
<212> TYPE: DNA
<213> ORGANISM: Artificial Sequence
<220> FEATURE:
<223> OTHER INFORMATION: Synthetic polynucleotide sequence for the
      light chain of of C. botulinum Type C,
      optimized for expression in E. coli.

<400> SEQUENCE: 26

| | | |
|---|---|---|
| atgccaatca ccatcaacaa cttcaactac tcagaccctg tcgacaacaa gaacattctg | 60 |
| tacctggaca ctcacctgaa cacccctagct aacgagcctg agaaggcctt tcggatcacc | 120 |
| ggaaacatct gggtcatccc tgatcgtttc tcccgtaact ccaacccaa cctgaacaag | 180 |
| cctcctcggg tcaccagccc taagagtggt tactacgacc ctaactacct gagtaccgac | 240 |
| tctgacaagg acaccttcct gaaggagatc atcaagctgt tcaagcgtat caactcccgt | 300 |
| gagatcggag aggagctcat ctacagactt tcgaccgata tccccttccc tggtaacaac | 360 |
| aatactccaa tcaacacctt cgacttcgac gtcgacttca actccgtcga cgtcaagact | 420 |
| cggcagggta caactgggt taagactggt agcatcaacc cttccgtcat catcactgga | 480 |
| cctcgtgaga acatcatcga cccagagact ccacgttca agctgactaa caacaccttc | 540 |
| gcggctcaag aaggattcgg tgctctgtca atcatctcca tctcacctcg tttcatgctg | 600 |
| acctactcga acgcaaccaa cgacgtcgga gagggtaggt tctctaagtc tgagttctgc | 660 |
| atggacccaa tcctgatcct gatgcatgag ctgaaccatg caatgcacaa cctgtacgga | 720 |
| atcgctatcc caaacgacca gaccatctcc tccgtgacct ccaacatctt ctactcccag | 780 |
| tacaacgtga gctggagta cgcagagatc tacgctttcg gaggtccaac tatcgacctt | 840 |
| atccctaagt ccgctaggaa gtacttcgag gagaaggctt tggattacta cagatccatc | 900 |
| gctaagagac tgaacagtat caccaccgca aacccttcca gcttcaacaa gtacatcggt | 960 |
| gagtacaagc agaagctgat cagaaagtac cgtttcgtcg tcgagtcttc aggtgaggtc | 1020 |
| acagtaaacc gtaacaagtt cgtcgagctg tacaacgagc ttacccagat cttcacagag | 1080 |
| ttcaactacg ctaagatcta caacgtccag aacaggaaga tctacctgtc caacgtgtac | 1140 |

```
actccggtga cggcgaacat cctggacgac aacgtctacg acatccagaa cggattcaac    1200
atccctaagt ccaacctgaa cgtactattc atgggtcaaa acctgtctcg aaacccagca    1260
ctgcgtaagg tcaaccctga gaacatgctg tacctgttca ccaagttctg c             1311
```

<210> SEQ ID NO 27
<211> LENGTH: 436
<212> TYPE: PRT
<213> ORGANISM: Artificial Sequence
<220> FEATURE:
<223> OTHER INFORMATION: Recombinant protein encoded by SEQ ID NO:26

<400> SEQUENCE: 27

```
Pro Ile Thr Ile Asn Asn Phe Asn Tyr Ser Asp Pro Val Asp Asn Lys
  1               5                  10                  15

Asn Ile Leu Tyr Leu Asp Thr His Leu Asn Thr Leu Ala Asn Glu Pro
             20                  25                  30

Glu Lys Ala Phe Arg Ile Thr Gly Asn Ile Trp Val Ile Pro Asp Arg
         35                  40                  45

Phe Ser Arg Asn Ser Asn Pro Asn Leu Asn Lys Pro Pro Arg Val Thr
     50                  55                  60

Ser Pro Lys Ser Gly Tyr Tyr Asp Pro Asn Tyr Leu Ser Thr Asp Ser
 65                  70                  75                  80

Asp Lys Asp Thr Phe Leu Lys Glu Ile Ile Lys Leu Phe Lys Arg Ile
                 85                  90                  95

Asn Ser Arg Glu Ile Gly Glu Glu Leu Ile Tyr Arg Leu Ser Thr Asp
            100                 105                 110

Ile Pro Phe Pro Gly Asn Asn Asn Thr Pro Ile Asn Thr Phe Asp Phe
        115                 120                 125

Asp Val Asp Phe Asn Ser Val Asp Val Lys Thr Arg Gln Gly Asn Asn
    130                 135                 140

Trp Val Lys Thr Gly Ser Ile Asn Pro Ser Val Ile Ile Thr Gly Pro
145                 150                 155                 160

Arg Glu Asn Ile Ile Asp Pro Glu Thr Ser Thr Phe Lys Leu Thr Asn
                165                 170                 175

Asn Thr Phe Ala Ala Gln Glu Gly Phe Gly Ala Leu Ser Ile Ile Ser
            180                 185                 190

Ile Ser Pro Arg Phe Met Leu Thr Tyr Ser Asn Ala Thr Asn Asp Val
        195                 200                 205

Gly Glu Gly Arg Phe Ser Lys Ser Glu Phe Cys Met Asp Pro Ile Leu
    210                 215                 220

Ile Leu Met His Glu Leu Asn His Ala Met His Asn Leu Tyr Gly Ile
225                 230                 235                 240

Ala Ile Pro Asn Asp Gln Thr Ile Ser Ser Val Thr Ser Asn Ile Phe
                245                 250                 255

Tyr Ser Gln Tyr Asn Val Lys Leu Glu Tyr Ala Glu Ile Tyr Ala Phe
            260                 265                 270

Gly Gly Pro Thr Ile Asp Leu Ile Pro Lys Ser Ala Arg Lys Tyr Phe
        275                 280                 285

Glu Glu Lys Ala Leu Asp Tyr Tyr Arg Ser Ile Ala Lys Arg Leu Asn
    290                 295                 300

Ser Ile Thr Thr Ala Asn Pro Ser Ser Phe Asn Lys Tyr Ile Gly Glu
305                 310                 315                 320

Tyr Lys Gln Lys Leu Ile Arg Lys Tyr Arg Phe Val Val Glu Ser Ser
                325                 330                 335
```

```
Gly Glu Val Thr Val Asn Arg Asn Lys Phe Val Glu Leu Tyr Asn Glu
            340                 345                 350

Leu Thr Gln Ile Phe Thr Glu Phe Asn Tyr Ala Lys Ile Tyr Asn Val
        355                 360                 365

Gln Asn Arg Lys Ile Tyr Leu Ser Asn Val Tyr Thr Pro Val Thr Ala
    370                 375                 380

Asn Ile Leu Asp Asp Asn Val Tyr Asp Ile Gln Asn Gly Phe Asn Ile
385                 390                 395                 400

Pro Lys Ser Asn Leu Asn Val Leu Phe Met Gly Gln Asn Leu Ser Arg
                405                 410                 415

Asn Pro Ala Leu Arg Lys Val Asn Pro Glu Asn Met Leu Tyr Leu Phe
            420                 425                 430

Thr Lys Phe Cys
        435
```

<210> SEQ ID NO 28
<211> LENGTH: 2436
<212> TYPE: DNA
<213> ORGANISM: Artificial Sequence
<220> FEATURE:
<223> OTHER INFORMATION: Synthetic polynucleotide sequence for the
      light chain with Hn segment of of C.
      botulinum Type C, optimized for expression
      in E. coli.

<400> SEQUENCE: 28

| | | | | | |
|---|---|---|---|---|---|
| atgccaatca | ccatcaacaa | cttcaactac | tcagaccctg | tcgacaacaa | gaacattctg | 60 |
| tacctggaca | ctcacctgaa | caccctagct | aacgagcctg | agaaggcctt | tcggatcacc | 120 |
| ggaaacatct | gggtcatccc | tgatcgtttc | tcccgtaact | ccaaccccaa | cctgaacaag | 180 |
| cctcctcggg | tcaccagccc | taagagtggt | tactacgacc | taactacct | gagtaccgac | 240 |
| tctgacaagg | cacccttcct | gaaggagatc | atcaagctgt | tcaagcgtat | caactcccgt | 300 |
| gagatcggag | aggagctcat | ctacagactt | cgaccgata | tccccttccc | tggtaacaac | 360 |
| aatactccaa | tcaacacctt | cgacttcgac | gtcgacttca | actccgtcga | cgtcaagact | 420 |
| cggcaggta | caactgggt | taagactggt | agcatcaacc | cttccgtcat | catcactgga | 480 |
| cctcgtgaga | acatcatcga | cccagagact | tccacgttca | agctgactaa | caccacttc | 540 |
| gcggctcaag | aaggattcgg | tgctctgtca | atcatctcca | tctcacctcg | tttcatgctg | 600 |
| acctactcga | acgcaaccaa | cgacgtcgga | gagggtaggt | tctctaagtc | tgagttctgc | 660 |
| atggacccaa | tcctgatcct | gatgcatgag | ctgaaccatg | caatgcacaa | cctgtacgga | 720 |
| atcgctatcc | caaacgacca | gaccatctcc | tccgtgacct | ccaacatctt | ctactcccag | 780 |
| tacaacgtga | agctggagta | cgcagagatc | tacgctttcg | gaggtccaac | tatcgacctt | 840 |
| atccctaagt | ccgctaggaa | gtacttcgag | gagaaggctt | tggattacta | cagatccatc | 900 |
| gctaagagac | tgaacagtat | caccaccgca | aaccccttca | gcttcaacaa | gtacatcggt | 960 |
| gagtacaagc | agaagctgat | cagaaagtac | cgtttcgtcg | tcgagtcttc | aggtgaggtc | 1020 |
| acagtaaacc | gtaacaagtt | cgtcgagctg | tacaacgagc | ttacccagat | cttcacagag | 1080 |
| ttcaactacg | ctaagatcta | caacgtccag | aacaggaaga | tctacctgtc | caacgtgtac | 1140 |
| actccggtga | cggcgaacat | cctggacgac | aacgtctacg | acatccagaa | cggattcaac | 1200 |
| atccctaagt | ccaacctgaa | cgtactattc | atgggtcaaa | acctgtctcg | aaacccagca | 1260 |
| ctgcgtaagg | tcaaccctga | gaacatgctg | tacctgttca | ccaagttctg | ctccctgtac | 1320 |

```
aacaagaccc ttgactgtag agagctgctg gtgaagaaca ctgacctgcc attcatcggt    1380
gacatcagtg acgtgaagac tgacatcttc ctgcgtaagg acatcaacga ggagactgag    1440
gtgatctact acccagacaa cgtgtcagta gaccaagtga tcctcagtaa gaacacctcc    1500
gagcatggac aactagacct gctctaccct agtatcgaca gtgagagtga gatcctgcca    1560
ggggagaatc aagtcttcta cgacaaccgt acccagaacg tggactacct gaactcctac    1620
tactacctag agtctcagaa gctgagtgac aacgtggagg acttcacttt cacgcgttca    1680
atcgaggagg ctctggacaa cagtgcaaag gtgtacactt acttccctac cctggctaac    1740
aaggtgaatg ccggtgtgca aggtggtctg ttcctgatgt gggcaaacga cgtggttgag    1800
gacttcacta ccaacatcct gcgtaaggac acactggaca agatctcaga tgtgtcagct    1860
atcatcccct acatcggacc cgcactgaac atctccaact ctgtgcgtcg tggaaacttc    1920
actgaggcat tcgcagtcac tggtgtcacc atcctgctgg aggcattccc tgagttcaca    1980
atccctgctc tgggtgcatt cgtgatctac agtaaggtcc aggagcgaaa cgagatcatc    2040
aagaccatcg acaactgtct ggagcagagg atcaagagat ggaaggactc ctacgagtgg    2100
atgatgggaa cgtggttgtc caggatcatc acccagttca acaacatctc ctaccagatg    2160
tacgactccc tgaactacca ggcaggtgca atcaaggcta agatcgacct ggagtacaag    2220
aagtactccg gaagcgacaa ggagaacatc aagagccagg ttgagaacct gaagaacagt    2280
ctggacgtca agatctcgga ggcaatgaac aacatcaaca agttcatccg agagtgctcc    2340
gtcacctacc tgttcaagaa catgctgcct aaggtcatcg acgagctgaa cgagttcgac    2400
cgaaacacca aggcaaagct gatcaacctg atcgac                              2436

<210> SEQ ID NO 29
<211> LENGTH: 811
<212> TYPE: PRT
<213> ORGANISM: Artificial Sequence
<220> FEATURE:
<223> OTHER INFORMATION: Recombinant protein encoded by SEQ ID NO:28

<400> SEQUENCE: 29

Pro Ile Thr Ile Asn Asn Phe Asn Tyr Ser Asp Pro Val Asp Asn Lys
 1               5                   10                  15

Asn Ile Leu Tyr Leu Asp Thr His Leu Asn Thr Leu Ala Asn Glu Pro
            20                  25                  30

Glu Lys Ala Phe Arg Ile Thr Gly Asn Ile Trp Val Ile Pro Asp Arg
        35                  40                  45

Phe Ser Arg Asn Ser Asn Pro Asn Leu Asn Lys Pro Pro Arg Val Thr
    50                  55                  60

Ser Pro Lys Ser Gly Tyr Tyr Asp Pro Asn Tyr Leu Ser Thr Asp Ser
65                  70                  75                  80

Asp Lys Asp Thr Phe Leu Lys Glu Ile Ile Lys Leu Phe Lys Arg Ile
                85                  90                  95

Asn Ser Arg Glu Ile Gly Glu Glu Leu Ile Tyr Arg Leu Ser Thr Asp
            100                 105                 110

Ile Pro Phe Pro Gly Asn Asn Asn Thr Pro Ile Asn Thr Phe Asp Phe
        115                 120                 125

Asp Val Asp Phe Asn Ser Val Asp Val Lys Thr Arg Gln Gly Asn Asn
    130                 135                 140

Trp Val Lys Thr Gly Ser Ile Asn Pro Ser Val Ile Ile Thr Gly Pro
145                 150                 155                 160

Arg Glu Asn Ile Ile Asp Pro Glu Thr Ser Thr Phe Lys Leu Thr Asn
```

```
                  165                 170                 175
Asn Thr Phe Ala Ala Gln Glu Gly Phe Gly Ala Leu Ser Ile Ile Ser
            180                 185                 190
Ile Ser Pro Arg Phe Met Leu Thr Tyr Ser Asn Ala Thr Asn Asp Val
            195                 200                 205
Gly Glu Gly Arg Phe Ser Lys Ser Glu Phe Cys Met Asp Pro Ile Leu
            210                 215                 220
Ile Leu Met His Glu Leu Asn His Ala Met His Asn Leu Tyr Gly Ile
225                 230                 235                 240
Ala Ile Pro Asn Asp Gln Thr Ile Ser Ser Val Thr Ser Asn Ile Phe
            245                 250                 255
Tyr Ser Gln Tyr Asn Val Lys Leu Glu Tyr Ala Glu Ile Tyr Ala Phe
            260                 265                 270
Gly Gly Pro Thr Ile Asp Leu Ile Pro Lys Ser Ala Arg Lys Tyr Phe
            275                 280                 285
Glu Glu Lys Ala Leu Asp Tyr Tyr Arg Ser Ile Ala Lys Arg Leu Asn
            290                 295                 300
Ser Ile Thr Thr Ala Asn Pro Ser Ser Phe Asn Lys Tyr Ile Gly Glu
305                 310                 315                 320
Tyr Lys Gln Lys Leu Ile Arg Lys Tyr Arg Phe Val Val Glu Ser Ser
            325                 330                 335
Gly Glu Val Thr Val Asn Arg Asn Lys Phe Val Glu Leu Tyr Asn Glu
            340                 345                 350
Leu Thr Gln Ile Phe Thr Glu Phe Asn Tyr Ala Lys Ile Tyr Asn Val
            355                 360                 365
Gln Asn Arg Lys Ile Tyr Leu Ser Asn Val Tyr Thr Pro Val Thr Ala
            370                 375                 380
Asn Ile Leu Asp Asp Asn Val Tyr Asp Ile Gln Asn Gly Phe Asn Ile
385                 390                 395                 400
Pro Lys Ser Asn Leu Asn Val Leu Phe Met Gly Gln Asn Leu Ser Arg
            405                 410                 415
Asn Pro Ala Leu Arg Lys Val Asn Pro Glu Asn Met Leu Tyr Leu Phe
            420                 425                 430
Thr Lys Phe Cys Ser Leu Tyr Asn Lys Thr Leu Asp Cys Arg Glu Leu
            435                 440                 445
Leu Val Lys Asn Thr Asp Leu Pro Phe Ile Gly Asp Ile Ser Asp Val
            450                 455                 460
Lys Thr Asp Ile Phe Leu Arg Lys Asp Ile Asn Glu Glu Thr Glu Val
465                 470                 475                 480
Ile Tyr Tyr Pro Asp Asn Val Ser Val Asp Gln Val Ile Leu Ser Lys
            485                 490                 495
Asn Thr Ser Glu His Gly Gln Leu Asp Leu Leu Tyr Pro Ser Ile Asp
            500                 505                 510
Ser Glu Ser Glu Ile Leu Pro Gly Glu Asn Gln Val Phe Tyr Asp Asn
            515                 520                 525
Arg Thr Gln Asn Val Asp Tyr Leu Asn Ser Tyr Tyr Tyr Leu Glu Ser
            530                 535                 540
Gln Lys Leu Ser Asp Asn Val Glu Asp Phe Thr Phe Thr Arg Ser Ile
545                 550                 555                 560
Glu Glu Ala Leu Asp Asn Ser Ala Lys Val Tyr Thr Tyr Phe Pro Thr
            565                 570                 575
Leu Ala Asn Lys Val Asn Ala Gly Val Gln Gly Gly Leu Phe Leu Met
            580                 585                 590
```

Trp Ala Asn Asp Val Val Glu Asp Phe Thr Thr Asn Ile Leu Arg Lys
            595                 600                 605

Asp Thr Leu Asp Lys Ile Ser Asp Val Ser Ala Ile Ile Pro Tyr Ile
        610                 615                 620

Gly Pro Ala Leu Asn Ile Ser Asn Ser Val Arg Arg Gly Asn Phe Thr
625                 630                 635                 640

Glu Ala Phe Ala Val Thr Gly Val Thr Ile Leu Leu Glu Ala Phe Pro
                645                 650                 655

Glu Phe Thr Ile Pro Ala Leu Gly Ala Phe Val Ile Tyr Ser Lys Val
            660                 665                 670

Gln Glu Arg Asn Glu Ile Ile Lys Thr Ile Asp Asn Cys Leu Glu Gln
        675                 680                 685

Arg Ile Lys Arg Trp Lys Asp Ser Tyr Glu Trp Met Met Gly Thr Trp
690                 695                 700

Leu Ser Arg Ile Ile Thr Gln Phe Asn Asn Ile Ser Tyr Gln Met Tyr
705                 710                 715                 720

Asp Ser Leu Asn Tyr Gln Ala Gly Ala Ile Lys Ala Lys Ile Asp Leu
                725                 730                 735

Glu Tyr Lys Lys Tyr Ser Gly Ser Asp Lys Glu Asn Ile Lys Ser Gln
            740                 745                 750

Val Glu Asn Leu Lys Asn Ser Leu Asp Val Lys Ile Ser Glu Ala Met
        755                 760                 765

Asn Asn Ile Asn Lys Phe Ile Arg Glu Cys Ser Val Thr Tyr Leu Phe
770                 775                 780

Lys Asn Met Leu Pro Lys Val Ile Asp Glu Leu Asn Glu Phe Asp Arg
785                 790                 795                 800

Asn Thr Lys Ala Lys Leu Ile Asn Leu Ile Asp
                805                 810

<210> SEQ ID NO 30
<211> LENGTH: 1323
<212> TYPE: DNA
<213> ORGANISM: Artificial Sequence
<220> FEATURE:
<223> OTHER INFORMATION: Synthetic polynucleotide sequence for the
      light chain of of C. botulinum Type D,
      optimized for expression in E. coli.

<400> SEQUENCE: 30
atgacctggc cagtcaagga cttcaactac tccgacccag tcaacgacaa cgacatcttg      60
tacttgagaa tcccacaaaa caagttgatc accaccccag tcaaggcttt catgatcacc     120
cagaacacct gggttatccc agagagattc tcctccgaca ccaacccatc cctgtccaag     180
ccaccaagac caacctccaa gtaccagtct tactacgacc atcttactt gtctaccgac      240 gagcaaaagg acaccttctt gaagggtatt atcaagctgt tcaagagaat caacgagaga     300
gacatcggta agaagttgat caactacttg gtcgttggtt ccccattcat gggtgactcc     360
tctaccccag aggacacctt cgacttcacc agacacacca ccaacattgc cgtcgagaag     420
ttcgagaacg gttcctggaa ggtcaccaac atcatcaccc catctgtttt gatcttcggt     480
ccattgccaa acatcttgga ctacaccgcc tccctgacct gcaaggtca gcaatccaac      540 ccatccttcg agggtttcgg taccctgtct attttgaagg tcgctccaga gttcttgttg     600
accttctccg acgtcacctc caaccaatcc tccgccgtct tgggtaagtc catcttctgt     660
atggacccag tcatcgcttt gatgcacgag ttgacccact ccctgcacca gttgtacggt     720

-continued

```
attaacatcc catctgacaa gagaatcaga ccacaggtct ctgagggttt cttctcccaa    780
gacggtccaa acgttcagtt cgaggagttg tacaccttcg gtggtttgga cgtcgagatt    840
atccaaattg agagatccca attgagagag aaggctttgg gtcactacaa ggacatcgcc    900
aagagactga acaacatcaa caagaccatt ccatcttcct ggatctccaa cattgacaag    960
tacaagaaga ttttctccga gaagtacaac ttcgacaagg acaacaccgg taacttcgtc   1020
gttaacatcg acaagttcaa ctctttgtac tccgacttga ccaacgttat gtctgaggtt   1080
gtctactcct cccaatacaa cgtcaagaac agaacccact acttctccag acactacttg   1140
ccagttttcg ctaacatctt ggacgacaac atttacacca tcagagacgg tttcaacttg   1200
accaacaagg gtttcaacat cgagaactcc ggtcaaaaca tcgagagaaa cccagccctg   1260
caaaagctgt cctccgagtc tgtcgtcgac ttgttcacca aggtctgttt gagattgacc   1320
aag                                                                 1323
```

<210> SEQ ID NO 31
<211> LENGTH: 440
<212> TYPE: PRT
<213> ORGANISM: Artificial Sequence
<220> FEATURE:
<223> OTHER INFORMATION: Recombinant protein encoded by SEQ ID NO:30

<400> SEQUENCE: 31

```
Thr Trp Pro Val Lys Asp Phe Asn Tyr Ser Asp Pro Val Asn Asp Asn
 1               5                  10                  15

Asp Ile Leu Tyr Leu Arg Ile Pro Gln Asn Lys Leu Ile Thr Thr Pro
            20                  25                  30

Val Lys Ala Phe Met Ile Thr Gln Asn Thr Trp Val Ile Pro Glu Arg
        35                  40                  45

Phe Ser Ser Asp Thr Asn Pro Ser Leu Ser Lys Pro Pro Arg Pro Thr
    50                  55                  60

Ser Lys Tyr Gln Ser Tyr Tyr Asp Pro Ser Tyr Leu Ser Thr Asp Glu
65                  70                  75                  80

Gln Lys Asp Thr Phe Leu Lys Gly Ile Ile Lys Leu Phe Lys Arg Ile
                85                  90                  95

Asn Glu Arg Asp Ile Gly Lys Lys Leu Ile Asn Tyr Leu Val Val Gly
            100                 105                 110

Ser Pro Phe Met Gly Asp Ser Ser Thr Pro Glu Asp Thr Phe Asp Phe
        115                 120                 125

Thr Arg His Thr Thr Asn Ile Ala Val Glu Lys Phe Glu Asn Gly Ser
    130                 135                 140

Trp Lys Val Thr Asn Ile Ile Thr Pro Ser Val Leu Ile Phe Gly Pro
145                 150                 155                 160

Leu Pro Asn Ile Leu Asp Tyr Thr Ala Ser Leu Thr Leu Gln Gly Gln
                165                 170                 175

Gln Ser Asn Pro Ser Phe Glu Gly Phe Gly Thr Leu Ser Ile Leu Lys
            180                 185                 190

Val Ala Pro Glu Phe Leu Leu Thr Phe Ser Asp Val Thr Ser Asn Gln
        195                 200                 205

Ser Ser Ala Val Leu Gly Lys Ser Ile Phe Cys Met Asp Pro Val Ile
    210                 215                 220

Ala Leu Met His Glu Leu Thr His Ser Leu His Gln Leu Tyr Gly Ile
225                 230                 235                 240

Asn Ile Pro Ser Asp Lys Arg Ile Arg Pro Gln Val Ser Glu Gly Phe
                245                 250                 255
```

```
Phe Ser Gln Asp Gly Pro Asn Val Gln Phe Glu Glu Leu Tyr Thr Phe
            260                 265                 270
Gly Gly Leu Asp Val Glu Ile Ile Gln Ile Glu Arg Ser Gln Leu Arg
        275                 280                 285
Glu Lys Ala Leu Gly His Tyr Lys Asp Ile Ala Lys Arg Leu Asn Asn
    290                 295                 300
Ile Asn Lys Thr Ile Pro Ser Ser Trp Ile Ser Asn Ile Asp Lys Tyr
305                 310                 315                 320
Lys Lys Ile Phe Ser Glu Lys Tyr Asn Phe Asp Lys Asp Asn Thr Gly
                325                 330                 335
Asn Phe Val Val Asn Ile Asp Lys Phe Asn Ser Leu Tyr Ser Asp Leu
            340                 345                 350
Thr Asn Val Met Ser Glu Val Val Tyr Ser Ser Gln Tyr Asn Val Lys
        355                 360                 365
Asn Arg Thr His Tyr Phe Ser Arg His Tyr Leu Pro Val Phe Ala Asn
    370                 375                 380
Ile Leu Asp Asp Asn Ile Tyr Thr Ile Arg Asp Gly Phe Asn Leu Thr
385                 390                 395                 400
Asn Lys Gly Phe Asn Ile Glu Asn Ser Gly Gln Asn Ile Glu Arg Asn
                405                 410                 415
Pro Ala Leu Gln Lys Leu Ser Ser Glu Ser Val Val Asp Leu Phe Thr
            420                 425                 430
Lys Val Cys Leu Arg Leu Thr Lys
        435                 440

<210> SEQ ID NO 32
<211> LENGTH: 2475
<212> TYPE: DNA
<213> ORGANISM: Artificial Sequence
<220> FEATURE:
<223> OTHER INFORMATION: Synthetic polynucleotide sequence for the
      light chain with Hn segment of of C.
      botulinum Type D, optimized for expression
      in E. coli.

<400> SEQUENCE: 32
atgacctggc cagtcaagga cttcaactac tccgacccag tcaacgacaa cgacatcttg     60
tacttgagaa tcccacaaaa caagttgatc accaccccag tcaaggcttt catgatcacc    120
cagaacacct gggttatccc agagagattc cctccgaca ccaacccatc cctgtccaag    180
ccaccaagac caacctccaa gtaccagtct tactacgacc atcttactt gtctaccgac    240 gagcaaaagg acaccttctt gaagggtatt atcaagctgt tcaagagaat caacgagaga    300
gacatcggta agaagttgat caactacttg gtcgttggtt ccccattcat gggtgactcc    360
tctaccccag aggacacctt cgacttcacc agacacacca ccaacattgc cgtcgagaag    420
ttcgagaacg ttcctggaa ggtcaccaac atcatcaccc atctgttttt gatcttcggt    480
ccattgccaa acatcttgga ctacaccgcc tccctgacct gcaaggtca gcaatccaac    540 ccatccttcg agggtttcgg taccctgtct attttgaagg tcgctccaga gttcttgttg    600
accttctccg acgtcaccct caaccaatcc tccgccgtct gggtaagtc catcttctgt    660 atggacccga tcatcgcttt gatgcacgag ttgacccact ccctgcacca gttgtacggt    720
attaacatcc catctgacaa gagaatcaga ccacaggtct ctgagggttt cttctcccaa    780
gacggtccaa acgttcagtt cgaggagttg tacaccttcg gtggtttgga cgtcgagatt    840
atccaaattg agagatccca attgagagag aaggctttgg gtcactacaa ggacatcgcc    900
```

-continued

```
aagagactga acaacatcaa caagaccatt ccatcttcct ggatctccaa cattgacaag    960
tacaagaaga ttttctccga agtacaac ttcgacaagg acaacaccgg taacttcgtc    1020
gttaacatcg acaagttcaa ctctttgtac tccgacttga ccaacgttat gtctgaggtt    1080
gtctactcct cccaatacaa cgtcaagaac agaacccact acttctccag acactacttg    1140
ccagttttcg ctaacatctt ggacgacaac atttacacca tcagagacgg tttcaacttg    1200
accaacaagg gtttcaacat cgagaactcc ggtcaaaaca tcgagagaaa cccagccctg    1260
caaaagctgt cctccgagtc tgtcgtcgac ttgttcacca aggtctgttt gagattgacc    1320
aagaactccc gtgacgactc cacctgcatc aaggtcaaga caacagact gccatacgtt    1380 gccgacaagg actccatctc caggagatc ttcgagaaca agatcatcac cgacgagacc    1440
aacgttcaaa actactccga caagttctct ttggacgagt ccatcctgga cggtcaggtc    1500
ccaatcaacc cagagatcgt cgacccactg ttgccaaacg tcaacatgga gccattgaac    1560
ttgccaggtg aggagatcgt cttctacgac gacatcacca agtacgtcga ctacttgaac    1620
tcctactact acttggagtc tcaaaagttg tctaacaacg tcgagaacat caccttgacc    1680
acctccgtcg aggaggcctt gggttactct aacaagatct acaccttcct gccatccttg    1740
gctgagaagg ttaacaaggg tgttcaagct ggtttgttcc tgaactgggc aacgaggtc    1800 gtcgaggact tcaccaccaa catcatgaag aaggacaccc tggacaagat ctccgacgtc    1860
tccgtcatca tcccatacat cggtccagcc ttgaacatcg gtaactccgc cctgagaggt    1920
aacttcaacc aggccttcgc caccgccggt gtcgccttcc tgctggaggg tttcccagag    1980
ttcaccatcc cagccctggg tgtcttcacc ttctactcct ccatccagga gagagaaag    2040 atcatcaaga ccatcgagaa ctgcttggag cagagagtca agagatggaa ggactcctac    2100
cagtggatgg tttccaactg gctgtccaga atcaccaccc aattcaacca catcaactac    2160
cagatgtacg actccctgtc ctaccaggcc gacgccatca aggccaagat cgacctggag    2220
tacaagaagt actccggttc cgacaaggag aacatcaagt cccaggtcga aacctgaag    2280 aactccttgg acgtcaagat ctccgaggcc atgaacaaca tcaacaagtt catccgtgag    2340
tgttccgtca cctacctgtt caagaacatg ctgccaaagg tcatcgacga gctgaacaag    2400
ttcgacctga aaccaagac cgagctgatc aacctgatcg actcccacaa catcatcctg    2460
gttggtgagg ttgac    2475
```

<210> SEQ ID NO 33
<211> LENGTH: 824
<212> TYPE: PRT
<213> ORGANISM: Artificial Sequence
<220> FEATURE:
<223> OTHER INFORMATION: Recombinant protein encoded by SEQ ID NO:32

<400> SEQUENCE: 33

```
Thr Trp Pro Val Lys Asp Phe Asn Tyr Ser Asp Pro Val Asn Asp Asn
  1               5                  10                  15

Asp Ile Leu Tyr Leu Arg Ile Pro Gln Asn Lys Leu Ile Thr Thr Pro
             20                  25                  30

Val Lys Ala Phe Met Ile Thr Gln Asn Thr Trp Val Ile Pro Glu Arg
         35                  40                  45

Phe Ser Ser Asp Thr Asn Pro Ser Leu Ser Lys Pro Pro Arg Pro Thr
     50                  55                  60

Ser Lys Tyr Gln Ser Tyr Tyr Asp Pro Ser Tyr Leu Ser Thr Asp Glu
 65                  70                  75                  80
```

```
Gln Lys Asp Thr Phe Leu Lys Gly Ile Ile Lys Leu Phe Lys Arg Ile
                85                  90                  95

Asn Glu Arg Asp Ile Gly Lys Lys Leu Ile Asn Tyr Leu Val Val Gly
            100                 105                 110

Ser Pro Phe Met Gly Asp Ser Thr Pro Glu Asp Thr Phe Asp Phe
            115                 120                 125

Thr Arg His Thr Thr Asn Ile Ala Val Glu Lys Phe Glu Asn Gly Ser
        130                 135                 140

Trp Lys Val Thr Asn Ile Ile Thr Pro Ser Val Leu Ile Phe Gly Pro
145                 150                 155                 160

Leu Pro Asn Ile Leu Asp Tyr Thr Ala Ser Leu Thr Leu Gln Gly Gln
                165                 170                 175

Gln Ser Asn Pro Ser Phe Glu Gly Phe Gly Thr Leu Ser Ile Leu Lys
            180                 185                 190

Val Ala Pro Glu Phe Leu Leu Thr Phe Ser Asp Val Thr Ser Asn Gln
        195                 200                 205

Ser Ser Ala Val Leu Gly Lys Ser Ile Phe Cys Met Asp Pro Val Ile
    210                 215                 220

Ala Leu Met His Glu Leu Thr His Ser Leu His Gln Leu Tyr Gly Ile
225                 230                 235                 240

Asn Ile Pro Ser Asp Lys Arg Ile Arg Pro Gln Val Ser Glu Gly Phe
                245                 250                 255

Phe Ser Gln Asp Gly Pro Asn Val Gln Phe Glu Glu Leu Tyr Thr Phe
            260                 265                 270

Gly Gly Leu Asp Val Glu Ile Ile Gln Ile Glu Arg Ser Gln Leu Arg
        275                 280                 285

Glu Lys Ala Leu Gly His Tyr Lys Asp Ile Ala Lys Arg Leu Asn Asn
    290                 295                 300

Ile Asn Lys Thr Ile Pro Ser Ser Trp Ile Ser Asn Ile Asp Lys Tyr
305                 310                 315                 320

Lys Lys Ile Phe Ser Glu Lys Tyr Asn Phe Asp Lys Asp Asn Thr Gly
                325                 330                 335

Asn Phe Val Val Asn Ile Asp Lys Phe Asn Ser Leu Tyr Ser Asp Leu
            340                 345                 350

Thr Asn Val Met Ser Glu Val Val Tyr Ser Ser Gln Tyr Asn Val Lys
        355                 360                 365

Asn Arg Thr His Tyr Phe Ser Arg His Tyr Leu Pro Val Phe Ala Asn
    370                 375                 380

Ile Leu Asp Asp Asn Ile Tyr Thr Ile Arg Asp Gly Phe Asn Leu Thr
385                 390                 395                 400

Asn Lys Gly Phe Asn Ile Glu Asn Ser Gly Gln Asn Ile Glu Arg Asn
                405                 410                 415

Pro Ala Leu Gln Lys Leu Ser Ser Glu Ser Val Val Asp Leu Phe Thr
            420                 425                 430

Lys Val Cys Leu Arg Leu Thr Lys Asn Ser Arg Asp Asp Ser Thr Cys
        435                 440                 445

Ile Lys Val Lys Asn Asn Arg Leu Pro Tyr Val Ala Asp Lys Asp Ser
    450                 455                 460

Ile Ser Gln Glu Ile Phe Glu Asn Lys Ile Ile Thr Asp Glu Thr Asn
465                 470                 475                 480

Val Gln Asn Tyr Ser Asp Lys Phe Ser Leu Asp Glu Ser Ile Leu Asp
                485                 490                 495
```

```
Gly Gln Val Pro Ile Asn Pro Glu Ile Val Asp Pro Leu Leu Pro Asn
            500                 505                 510
Val Asn Met Glu Pro Leu Asn Leu Pro Gly Glu Glu Ile Val Phe Tyr
            515                 520                 525
Asp Asp Ile Thr Lys Tyr Val Asp Tyr Leu Asn Ser Tyr Tyr Tyr Leu
            530                 535                 540
Glu Ser Gln Lys Leu Ser Asn Asn Val Glu Asn Ile Thr Leu Thr Thr
545                 550                 555                 560
Ser Val Glu Glu Ala Leu Gly Tyr Ser Asn Lys Ile Tyr Thr Phe Leu
                565                 570                 575
Pro Ser Leu Ala Glu Lys Val Asn Lys Gly Val Gln Ala Gly Leu Phe
            580                 585                 590
Leu Asn Trp Ala Asn Glu Val Val Glu Asp Phe Thr Thr Asn Ile Met
            595                 600                 605
Lys Lys Asp Thr Leu Asp Lys Ile Ser Asp Val Ser Val Ile Ile Pro
610                 615                 620
Tyr Ile Gly Pro Ala Leu Asn Ile Gly Asn Ser Ala Leu Arg Gly Asn
625                 630                 635                 640
Phe Asn Gln Ala Phe Ala Thr Ala Gly Val Ala Phe Leu Leu Glu Gly
                645                 650                 655
Phe Pro Glu Phe Thr Ile Pro Ala Leu Gly Val Phe Thr Phe Tyr Ser
            660                 665                 670
Ser Ile Gln Glu Arg Glu Lys Ile Ile Lys Thr Ile Glu Asn Cys Leu
            675                 680                 685
Glu Gln Arg Val Lys Arg Trp Lys Asp Ser Tyr Gln Trp Met Val Ser
            690                 695                 700
Asn Trp Leu Ser Arg Ile Thr Thr Gln Phe Asn His Ile Asn Tyr Gln
705                 710                 715                 720
Met Tyr Asp Ser Leu Ser Tyr Gln Ala Asp Ala Ile Lys Ala Lys Ile
                725                 730                 735
Asp Leu Glu Tyr Lys Lys Tyr Ser Gly Ser Asp Lys Glu Asn Ile Lys
            740                 745                 750
Ser Gln Val Glu Asn Leu Lys Asn Ser Leu Asp Val Lys Ile Ser Glu
            755                 760                 765
Ala Met Asn Asn Ile Asn Lys Phe Ile Arg Glu Cys Ser Val Thr Tyr
770                 775                 780
Leu Phe Lys Asn Met Leu Pro Lys Val Ile Asp Glu Leu Asn Lys Phe
785                 790                 795                 800
Asp Leu Arg Thr Lys Thr Glu Leu Ile Asn Leu Ile Asp Ser His Asn
                805                 810                 815
Ile Ile Leu Val Gly Glu Val Asp
            820
```

<210> SEQ ID NO 34
<211> LENGTH: 1283
<212> TYPE: DNA
<213> ORGANISM: Artificial Sequence
<220> FEATURE:
<223> OTHER INFORMATION: Synthetic polynucleotide sequence for the
      light chain of of C. botulinum Type E,
      optimized for expression in E. coli.

<400> SEQUENCE: 34

```
catatgccga aaatcaactc gttcaactac aacgacccgg tgaatgaccg cacaatcctg      60
tacattaagc cgggcggttg ccaggagttc tacaagagct ttaacattat gaagaacatc    120
```

-continued

```
tggatcatcc ctgaacgcaa tgtgatcggg acaacgccac aagatttcca ccctccgact      180
tcgctcaaaa acggggactc ctcctactac gacccaaatt acttgcaaag cgatgaggag      240
aaagatcggt tcctgaagat tgtgacaaag atcttcaacc gtattaacaa caatctctcg      300 ggggcatcc tcctggagga attatccaag gcgaacccctt acctgggcaa cgacaacact      360
ccagacaacc agttccacat tggcgacgcc tccgcggtgg agatcaagtt ctcgaatggc      420
agtcaggaca tccttctccc taatgtcatt attatgggcg ccgagccgga cctttttgaa      480
accaattcca gcaacatctc gctgcgcaac aactacatgc cgagcaatca cggctttggg      540
tcgatcgcga tcgtgacttt ctcgccggag tactcctttc gcttcaacga caactccatg      600
aacgagttca ttcaggaccc ggcgctcacc ctcatgcacg agctgatcca ctcgttacat      660
ggcttgtacg gcgcgaaggg gatcacgacc aagtatacca ttacgcagaa acagaaccca      720
cttatcacga acatccgtgg gacgaacatc gaggagttcc tcacgttcgg ggggaccgac      780
ctgaacatta tcaccagcgc ccagtccaac gacatttaca cgaacctgct ggcagattac      840
aaaaaaattg cctccaagct ctccaaggtc caggtatcga acccgttgct caatccttac      900
aaggacgtct tcgaggctaa gtatgggctg gataaggatg cctcaggaat ctactctgtg      960
aacatcaaca aattcaacga catcttcaag aagctgtaca gcttcaccga gtttgacctc     1020
gccaccaagt tccaggtcaa atgtcggcaa acgtacattg ccagtataaa atattttaag     1080
ctgtcgaatc ttctcaacga ctctatctat aacatctccg agggtacaa tattaacaac      1140 ttaaaagtca acttccgagg gcagaacgca aatctcaacc cacggattat tactcctatt     1200
acaggccgcg ggctcgtcaa gaagatcatc cgattttgca aaaacattgt cagcgttaaa     1260
ggcatccgta agtaatagga tcc                                             1283
```

<210> SEQ ID NO 35
<211> LENGTH: 427
<212> TYPE: PRT
<213> ORGANISM: Artificial Sequence
<220> FEATURE:
<223> OTHER INFORMATION: Recombinant protein encoded by SEQ ID NO:34
<221> NAME/KEY: UNSURE
<222> LOCATION: (424)...(425)
<223> OTHER INFORMATION: Any amino acid at each position
<221> NAME/KEY: UNSURE
<222> LOCATION: (427)...(427)
<223> OTHER INFORMATION: Any amino acid

<400> SEQUENCE: 35

```
Met Pro Lys Ile Asn Ser Phe Asn Tyr Asn Asp Pro Val Asn Asp Arg
  1               5                  10                  15

Thr Ile Leu Tyr Ile Lys Pro Gly Gly Cys Gln Glu Phe Tyr Lys Ser
             20                  25                  30

Phe Asn Ile Met Lys Asn Ile Trp Ile Ile Pro Glu Arg Asn Val Ile
         35                  40                  45

Gly Thr Thr Pro Gln Asp Phe His Pro Pro Thr Ser Leu Lys Asn Gly
     50                  55                  60

Asp Ser Ser Tyr Tyr Asp Pro Asn Tyr Leu Gln Ser Asp Glu Glu Lys
 65                  70                  75                  80

Asp Arg Phe Leu Lys Ile Val Thr Lys Ile Phe Asn Arg Ile Asn Asn
                 85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125
```

Ala Ser Ala Val Glu Ile Lys Phe Ser Asn Gly Ser Gln Asp Ile Leu
        130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Xaa Xaa Asp Xaa
            420                 425

<210> SEQ ID NO 36
<211> LENGTH: 2415
<212> TYPE: DNA
<213> ORGANISM: Artificial Sequence
<220> FEATURE:
<223> OTHER INFORMATION: Synthetic polynucleotide gene sequence for
      the light chain with Hn segment of of C.
      botulinum Type E, optimized for expression
      in E. coli.

<400> SEQUENCE: 36
catatgccga aaatcaactc gttcaactac aacgacccgg tgaatgaccg cacaatcctg      60
tacattaagc cgggcggttg ccaggagttc tacaagagct taacattat gaagaacatc     120 tggatcatcc ctgaacgcaa tgtgatcggg acaacgccac aagatttcca ccctccgact     180
tcgctcaaaa acgggactc ctcctactac gacccaaatt acttgcaaag cgatgaggag     240

```
aaagatcggt tcctgaagat tgtgacaaag atcttcaacc gtattaacaa caatctctcg    300
gggggcatcc tcctggagga attatccaag gcgaacccct taacctgggcaa cgacaacact   360
ccagacaacc agttccacat tggcgacgcc tccgcggtgg agatcaagtt ctcgaatggc    420
agtcaggaca tccttctccc taatgtcatt attatgggcg ccgagccgga ccttttgaa    480
accaattcca gcaacatctc gctgcgcaac aactacatgc cgagcaatca cggctttggg    540
tcgatcgcga tcgtgacttt ctcgccggag tactcctttc gcttcaacga caactccatg    600
aacgagttca ttcaggaccc ggcgctcacc ctcatgcacg agctgatcca ctcgttacat    660
ggcttgtacg gcgcgaaggg gatcacgacc aagtatacca ttacgcagaa acagaaccca    720
cttatcacga acatccgtgg gacgaacatc gaggagttcc tcacgttcgg ggggaccgac    780
ctgaacatta tcaccagcgc ccagtccaac gacatttaca cgaacctgct ggcagattac    840
aaaaaaattg cctccaagct ctccaaggtc caggtatcga acccgttgct caatccttac    900
aaggacgtct tcgaggctaa gtatgggctg gataaggatg cctcaggaat ctactctgtg    960
aacatcaaca aattcaacga catcttcaag aagctgtaca gcttcaccga gtttgacctc   1020
gccaccaagt tccaggtcaa atgtcggcaa acgtacattg ccagtataaa ataattttaag   1080
ctgtcgaatc ttctcaacga ctctatctat aacatctccg aggggtacaa tattaacaac   1140
ttaaaagtca acttccgagg gcagaacgca aatctcaacc cacggattat tactcctatt   1200
acaggccgcg ggctcgtcaa agaagatcatc cgattttgca aaaacattgt cagcgttaaa   1260
ggcatccgta agtccatctg catcgagatc aacaacggtg agctgttctt cgtggcttcc   1320
gagaacagtt acaacgatga caacatcaac actcctaagg agattgacga caccgtcact   1380
tctaacaaca actacgaaaa cgacctggac caggtcatcc taaacttcaa ctccgagtcc   1440
gcccctggtc tgtccgacga gaagctgaac ctgaccatcc agaacgacgc ttacatccca   1500
aagtacgact ccaacggtac atccgatatc gagcagcatg acgttaacga gcttaacgtc   1560
ttcttctact tagacgctca gaaggtgccc gagggtgaga acaacgtcaa tctcacctct   1620
tcaattgaca cagccttgtt ggagcagcct aagatctaca ccttcttctc ctccgagttc   1680
atcaacaacg tcaacaagcc tgtgcaggcc gcattgttcg taagctggat tcagcaggtg   1740
ttagtagact tcactactga ggctaaccag aagtccactg ttgacaagat cgctgacatc   1800
tccatcgtcg tcccatacat cggtctggct ctgaacatcg gcaacgaggc acagaagggc   1860
aacttcaagg atgcccttga gttgttgggt gccggtattt tgttggagtt cgaacccgag   1920
ctgctgatcc ctaccatcct ggtcttcacg atcaagtcct tcctgggttc ctccgacaac   1980
aagaacaagg tcattaaggc catcaacaac gcccctgaagg agcgtgacga gaagtggaag   2040
gaagtctatt ccttcatcgt ctcgaactgg atgaccaaga tcaacaccca gttcaacaag   2100
cgaaaggagc agatgtacca ggctctgcag aaccaggtca acgccatcaa gaccatcatc   2160
gagtccaagt acaactccta caccctggag gagaagaacg agcttaccaa caagtacgat   2220
atcaagcaga tcgagaacga gctgaaccag aaggtctcca tcgccatgaa caacatcgac   2280
aggttcctga ccgagtcctc catctcctac ctgatgaagc tcatcaacga ggtcaagatc   2340
aacaagctgc gagagtacga cgagaatgtc aagacgtacc tgctgaacta catcatccag   2400
cacggatcca tcctg                                                   2415
```

<210> SEQ ID NO 37
<211> LENGTH: 804
<212> TYPE: PRT
<213> ORGANISM: Artificial Sequence -continued

```
<220> FEATURE:
<223> OTHER INFORMATION: Recombinant protein encoded by SEQ ID NO:36

<400> SEQUENCE: 37

Met Pro Lys Ile Asn Ser Phe Asn Tyr Asn Asp Pro Val Asn Asp Arg
 1               5                  10                  15

Thr Ile Leu Tyr Ile Lys Pro Gly Gly Cys Gln Glu Phe Tyr Lys Ser
             20                  25                  30

Phe Asn Ile Met Lys Asn Ile Trp Ile Ile Pro Glu Arg Asn Val Ile
         35                  40                  45

Gly Thr Thr Pro Gln Asp Phe His Pro Pro Thr Ser Leu Lys Asn Gly
     50                  55                  60

Asp Ser Ser Tyr Tyr Asp Pro Asn Tyr Leu Gln Ser Asp Glu Glu Lys
 65                  70                  75                  80

Asp Arg Phe Leu Lys Ile Val Thr Lys Ile Phe Asn Arg Ile Asn Asn
                 85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400
```

-continued

```
Gly Arg Gly Leu Val Lys Lys Ile Ile Arg Phe Cys Lys Asn Ile Val
            405                 410                 415
Ser Val Lys Gly Ile Arg Lys Ser Ile Cys Ile Glu Ile Asn Asn Gly
            420                 425                 430
Glu Leu Phe Phe Val Ala Ser Glu Asn Ser Tyr Asn Asp Asp Asn Ile
            435                 440                 445
Asn Thr Pro Lys Glu Ile Asp Asp Thr Val Thr Ser Asn Asn Asn Tyr
            450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
            485                 490                 495
Tyr Ile Pro Lys Tyr Asp Ser Asn Gly Thr Ser Asp Ile Glu Gln His
            500                 505                 510
Asp Val Asn Glu Leu Asn Val Phe Phe Tyr Leu Asp Ala Gln Lys Val
            515                 520                 525
Pro Glu Gly Glu Asn Asn Val Asn Leu Thr Ser Ser Ile Asp Thr Ala
            530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Ser Trp Ile
            565                 570                 575
Gln Gln Val Leu Val Asp Phe Thr Thr Glu Ala Asn Gln Lys Ser Thr
            580                 585                 590
Val Asp Lys Ile Ala Asp Ile Ser Ile Val Val Pro Tyr Ile Gly Leu
            595                 600                 605
Ala Leu Asn Ile Gly Asn Glu Ala Gln Lys Gly Asn Phe Lys Asp Ala
            610                 615                 620
Leu Glu Leu Leu Gly Ala Gly Ile Leu Leu Glu Phe Glu Pro Glu Leu
625                 630                 635                 640
Leu Ile Pro Thr Ile Leu Val Phe Thr Ile Lys Ser Phe Leu Gly Ser
            645                 650                 655
Ser Asp Asn Lys Asn Lys Val Ile Lys Ala Ile Asn Asn Ala Leu Lys
            660                 665                 670
Glu Arg Asp Glu Lys Trp Lys Glu Val Tyr Ser Phe Ile Val Ser Asn
            675                 680                 685
Trp Met Thr Lys Ile Asn Thr Gln Phe Asn Lys Arg Lys Glu Gln Met
            690                 695                 700
Tyr Gln Ala Leu Gln Asn Gln Val Asn Ala Ile Lys Thr Ile Ile Glu
705                 710                 715                 720
Ser Lys Tyr Asn Ser Tyr Thr Leu Glu Glu Lys Asn Glu Leu Thr Asn
            725                 730                 735
Lys Tyr Asp Ile Lys Gln Ile Glu Asn Glu Leu Asn Gln Lys Val Ser
            740                 745                 750
Ile Ala Met Asn Asn Ile Asp Arg Phe Leu Thr Glu Ser Ser Ile Ser
            755                 760                 765
Tyr Leu Met Lys Leu Ile Asn Glu Val Lys Ile Asn Lys Leu Arg Glu
            770                 775                 780
Tyr Asp Glu Asn Val Lys Thr Tyr Leu Leu Asn Tyr Ile Ile Gln His
785                 790                 795                 800
Gly Ser Ile Leu
```

-continued

```
<210> SEQ ID NO 38
<211> LENGTH: 1334
<212> TYPE: DNA
<213> ORGANISM: Artificial Sequence
<220> FEATURE:
<223> OTHER INFORMATION: Synthetic polynucleotide sequence for the
      light chain of of C. botulinum Type F,
      optimized for expression in E. coli.

<400> SEQUENCE: 38
catatgccgg ttgtcatcaa ttcttttaac tacaacgacc cggtgaacga cgacacgatt      60
ctgtacatgc aaatcccttta cgaggagaag tctaaaaagt attataaggc gttcgagatc    120
atgcgcaacg tgtggatcat cccggaacgc aacactattg gacagaccc gtcggacttc     180 gatccgcctg cgtcgcttga aaacggctca tcagcatact atgacccaaa ttatttgact    240
acggacgcgg aaaaggaccg ttatctcaag accacaatca agctcttcaa gcgtattaac    300
tccaacccgg cgggcgaggt attgcttcag gagatttcct acgccaagcc ttacctcggc    360
aatgagcata ctcctatcaa cgagttccac cctgtgaccc gaaccacgtc tgtaaacatt    420
aagagttcga cgaatgtaaa gtcgtcaatt attctcaacc tcttggtcct ggcgcggg     480 ccggacatct tcgagaactc ttcctacccg gttcgcaagc tcatggacag tgggggggtc    540
tatgacccga gcaacgacgg gttcggttcc atcaatatcg tgaccttctc acctgagtac    600
gagtatacat taacgacat cagcggcggc tacaacagta gcaccgagtc ctttatcgcc    660
gacccggcca tcagcctcgc tcacgagctc atccacgccc tgcacgggct gtacggggcc    720
cggggcgtta catataagga gaccatcaaa gtgaagcagg cgccactcat gattgccgaa    780
aagccaatcc gattggagga gttcctgaca ttcggggcc aggacctgaa tattatcact    840
agtgcaatga aggagaagat ttataacaac ctgctcgcga actatgagaa gatcgccact    900
cgcttatccc gggtgaactc cgccccaccg gagtatgaca ttaacgagta aagactac    960 ttccagtgga agtatggact ggataaaaac gcggacgggt cttacaccgt gaacgagaac   1020
aaattcaacg agatctacaa gaagctctac agcttcacgg agatcgacct cgcgaacaag   1080
ttcaaggtga agtgccggaa cacgtatttc atcaagtacg gcttcttaaa ggtgccaaac   1140
ctgttagacg acgacatttta taccgtatcg gagggcttca atattggtaa tctggccgtg   1200
aacaatcgcg gccagaatat taaacttaac ccgaaaatta tcgactcgat cccagacaag   1260
gggttagttg agaagatcgt caagttctgc aagtcggtca tccctcgcaa ggggacgaag   1320
aattaatagg atcc                                                     1334

<210> SEQ ID NO 39
<211> LENGTH: 443
<212> TYPE: PRT
<213> ORGANISM: Artificial Sequence
<220> FEATURE:
<223> OTHER INFORMATION: Recombinant protein encoded by SEQ ID NO:38
<221> NAME/KEY: UNSURE
<222> LOCATION: (441)...(442)
<223> OTHER INFORMATION: Any amino acid at each position

<400> SEQUENCE: 39

Met Pro Val Val Ile Asn Ser Phe Asn Tyr Asn Asp Pro Val Asn Asp
 1               5                  10                  15

Asp Thr Ile Leu Tyr Met Gln Ile Pro Tyr Glu Glu Lys Ser Lys Lys
             20                  25                  30

Tyr Tyr Lys Ala Phe Glu Ile Met Arg Asn Val Trp Ile Ile Pro Glu
         35                  40                  45
```

```
Arg Asn Thr Ile Gly Thr Asp Pro Ser Asp Phe Asp Pro Pro Ala Ser
 50                  55                  60
Leu Glu Asn Gly Ser Ser Ala Tyr Tyr Asp Pro Asn Tyr Leu Thr Thr
 65                  70                  75                  80
Asp Ala Glu Lys Asp Arg Tyr Leu Lys Thr Thr Ile Lys Leu Phe Lys
                 85                  90                  95
Arg Ile Asn Ser Asn Pro Ala Gly Glu Val Leu Leu Gln Glu Ile Ser
                100                 105                 110
Tyr Ala Lys Pro Tyr Leu Gly Asn Glu His Thr Pro Ile Asn Glu Phe
            115                 120                 125
His Pro Val Thr Arg Thr Thr Ser Val Asn Ile Lys Ser Ser Thr Asn
130                 135                 140
Val Lys Ser Ser Ile Ile Leu Asn Leu Val Leu Gly Ala Gly Pro
145                 150                 155                 160
Asp Ile Phe Glu Asn Ser Ser Tyr Pro Val Arg Lys Leu Met Asp Ser
                165                 170                 175
Gly Gly Val Tyr Asp Pro Ser Asn Asp Gly Phe Gly Ser Ile Asn Ile
            180                 185                 190
Val Thr Phe Ser Pro Glu Tyr Glu Tyr Thr Phe Asn Asp Ile Ser Gly
            195                 200                 205
Gly Tyr Asn Ser Ser Thr Glu Ser Phe Ile Ala Asp Pro Ala Ile Ser
210                 215                 220
Leu Ala His Glu Leu Ile His Ala Leu His Gly Leu Tyr Gly Ala Arg
225                 230                 235                 240
Gly Val Thr Tyr Lys Glu Thr Ile Lys Val Lys Gln Ala Pro Leu Met
                245                 250                 255
Ile Ala Glu Lys Pro Ile Arg Leu Glu Glu Phe Leu Thr Phe Gly Gly
                260                 265                 270
Gln Asp Leu Asn Ile Ile Thr Ser Ala Met Lys Glu Lys Ile Tyr Asn
            275                 280                 285
Asn Leu Leu Ala Asn Tyr Glu Lys Ile Ala Thr Arg Leu Ser Arg Val
290                 295                 300
Asn Ser Ala Pro Pro Glu Tyr Asp Ile Asn Glu Tyr Lys Asp Tyr Phe
305                 310                 315                 320
Gln Trp Lys Tyr Gly Leu Asp Lys Asn Ala Asp Gly Ser Tyr Thr Val
                325                 330                 335
Asn Glu Asn Lys Phe Asn Glu Ile Tyr Lys Lys Leu Tyr Ser Phe Thr
                340                 345                 350
Glu Ile Asp Leu Ala Asn Lys Phe Lys Val Lys Cys Arg Asn Thr Tyr
            355                 360                 365
Phe Ile Lys Tyr Gly Phe Leu Lys Val Pro Asn Leu Leu Asp Asp Asp
            370                 375                 380
Ile Tyr Thr Val Ser Glu Gly Phe Asn Ile Gly Asn Leu Ala Val Asn
385                 390                 395                 400
Asn Arg Gly Gln Asn Ile Lys Leu Asn Pro Lys Ile Ile Asp Ser Ile
                405                 410                 415
Pro Asp Lys Gly Leu Val Glu Lys Ile Val Lys Phe Cys Lys Ser Val
            420                 425                 430
Ile Pro Arg Lys Gly Thr Lys Asn Xaa Xaa Asp
            435                 440
```

<210> SEQ ID NO 40
<211> LENGTH: 2577
<212> TYPE: DNA

-continued

<213> ORGANISM: Artificial Sequence
<220> FEATURE:
<223> OTHER INFORMATION: Synthetic polynucleotide sequence for the
      light chain with Hn segment of of C.
      botulinum Type F, optimized for expression
      in E. coli.

<400> SEQUENCE: 40

| | |
|---|---|
| catatgccgg ttgtcatcaa ttcttttaac tacaacgacc cggtgaacga cgacacgatt | 60 |
| ctgtacatgc aaatccctta cgaggagaag tctaaaaagt attataaggc gttcgagatc | 120 |
| atgcgcaacg tgtggatcat cccggaacgc aacactattg gacagaccc gtcggacttc | 180 |
| gatccgcctg cgtcgcttga aaacggctca tcagcatact atgacccaaa ttatttgact | 240 |
| acggacgcgg aaaaggaccg ttatctcaag accacaatca agctcttcaa gcgtattaac | 300 |
| tccaacccgg cgggcgaggt attgcttcag gagatttcct acgccaagcc ttacctcggc | 360 |
| aatgagcata ctcctatcaa cgagttccac cctgtgaccc gaaccacgtc tgtaaacatt | 420 |
| aagagttcga cgaatgtaaa gtcgtcaatt attctcaacc tcttggtcct ggcgcgggg | 480 |
| ccggacatct tcgagaactc ttcctacccg gttcgcaagc tcatggacag tgggggggtc | 540 |
| tatgacccga gcaacgacgg gttcggttcc atcaatatcg tgaccttctc acctgagtac | 600 |
| gagtatacat ttaacgacat cagcggcggc tacaacagta gcaccgagtc ctttatcgcc | 660 |
| gacccggcca tcagcctcgc tcacgagctc atccacgccc tgcacgggct gtacggggcc | 720 |
| cggggcgtta catataagga gaccatcaaa gtgaagcagg cgccactcat gattgccgaa | 780 |
| aagccaatcc gattggagga gttcctgaca ttcgggggcc aggacctgaa tattatcact | 840 |
| agtgcaatga ggagaagat ttataacaac ctgctcgcga actatgagaa gatcgccact | 900 |
| cgcttatccc gggtgaactc cgccccaccg gagtatgaca ttaacgagta taagagactac | 960 |
| ttccagtgga gtatggact ggataaaaac gcggacgggt cttacaccgt gaacgagaac | 1020 |
| aaattcaacg agatctacaa gaagctctac agcttcacgg agatcgacct cgcgaacaag | 1080 |
| ttcaaggtga gtgccggaaa cacgtatttc atcaagtacg gcttcttaaa ggtgccaaac | 1140 |
| ctgttagaca cgacatttta taccgtatcg gagggcttca atattggtaa tctggccgtg | 1200 |
| aacaatcgcg gccagaatat taaacttaac ccgaaaatta tcgactcgat cccagacaag | 1260 |
| gggttagttg agaagatcgt caagttctgc aagtcggtca tccctcgcaa ggggacgaag | 1320 |
| aattgcaagt ccgtcatccc acgtaagggt accaaggccc caccacgtct gtgtattaga | 1380 |
| gtcaacaact cagaattatt ctttgtcgct tccgagtcaa gctacaacga gaacgatatt | 1440 |
| aacacaccta agagattga cgatactacc aacctaaaca caactaccg gaacaacttg | 1500 |
| gatgaggtta ttttggatta caactcacag accatccctc aaatttccaa ccgtaccta | 1560 |
| aacactcttg tccaagacaa ctcctacgtt ccaagatacg attctaacgg tacctcagag | 1620 |
| atcgaggagt atgatgttgt tgactttaac gtctttttct atttgcatgc ccagaaggtg | 1680 |
| ccagaaggtg aaaccaacat ctcattgact tcttccattg ataccgcctt gttggaagag | 1740 |
| tccaaggata tcttcttttc ttcggagttt atcgatacta tcaacaagcc tgtcaacgcc | 1800 |
| gctctgttca ttgattggat tagcaaggtc atcagagatt ttaccactga gctactcaa | 1860 |
| aagtccactg ttgataagat tgctgacatc tcttttgattg tccctatgt cggtcttgct | 1920 |
| ttgaacatca ttattgaggc agaaaagggt aactttgagg aggcttttga attgttggga | 1980 |
| gttggtattt tgttggagtt tgttccagaa cttaccattc ctgtcatttt agttttttacg | 2040 |
| atcaagtcct acatcgattc atacgagaac aagaataaag caattaaagc tattaacaac | 2100 |

```
tccttgatcg aaagagaggc taagtggaag gaaatctact catggattgt atcaaactgg   2160
cttactagaa ttaacactca atttaacaag agaaaggagc aaatgtacca ggctctgcaa   2220
aaccaagtcg atgctatcaa gactgcaatt gaatacaagt acaacaacta tacttccgat   2280
gagaagaaca gacttgaatc tgaatacaat atcaacaaca ttgaagaaga gttgaacaag   2340
aaagtttctt tggctatgaa gaatatcgaa agatttatga ccgaatcctc tatctcttac   2400
ttgatgaagt tgatcaatga ggccaaggtt ggtaagttga agaagtacga taaccacgtt   2460
aagagcgatc tgctgaacta cattctcgac cacagatcaa tcctgggaga gcagacaaac   2520
gagctgagtg atttggttac ttccactttg aactcctcca ttccatttga gctttct      2577
```

<210> SEQ ID NO 41
<211> LENGTH: 858
<212> TYPE: PRT
<213> ORGANISM: Artificial Sequence
<220> FEATURE:
<223> OTHER INFORMATION: Recombinant protein encoded by SEQ ID NO:40

<400> SEQUENCE: 41

```
Met Pro Val Val Ile Asn Ser Phe Asn Tyr Asn Asp Pro Val Asn Asp
  1               5                  10                  15

Asp Thr Ile Leu Tyr Met Gln Ile Pro Tyr Glu Glu Lys Ser Lys Lys
             20                  25                  30

Tyr Tyr Lys Ala Phe Glu Ile Met Arg Asn Val Trp Ile Ile Pro Glu
         35                  40                  45

Arg Asn Thr Ile Gly Thr Asp Pro Ser Asp Phe Asp Pro Pro Ala Ser
     50                  55                  60

Leu Glu Asn Gly Ser Ser Ala Tyr Tyr Asp Pro Asn Tyr Leu Thr Thr
 65                  70                  75                  80

Asp Ala Glu Lys Asp Arg Tyr Leu Lys Thr Thr Ile Lys Leu Phe Lys
                 85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285
```

```
Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Gly Thr Lys Asn Cys Lys Ser Val Ile Pro Arg Lys
        435                 440                 445

Gly Thr Lys Ala Pro Pro Arg Leu Cys Ile Arg Val Asn Asn Ser Glu
    450                 455                 460

Leu Phe Phe Val Ala Ser Glu Ser Ser Tyr Asn Glu Asn Asp Ile Asn
465                 470                 475                 480

Thr Pro Lys Glu Ile Asp Asp Thr Thr Asn Leu Asn Asn Asn Tyr Arg
                485                 490                 495

Asn Asn Leu Asp Glu Val Ile Leu Asp Tyr Asn Ser Gln Thr Ile Pro
            500                 505                 510

Gln Ile Ser Asn Arg Thr Leu Asn Thr Leu Val Gln Asp Asn Ser Tyr
        515                 520                 525

Val Pro Arg Tyr Asp Ser Asn Gly Thr Ser Glu Ile Glu Glu Tyr Asp
530                 535                 540

Val Val Asp Phe Asn Val Phe Phe Tyr Leu His Ala Gln Lys Val Pro
545                 550                 555                 560

Glu Gly Glu Thr Asn Ile Ser Leu Thr Ser Ser Ile Asp Thr Ala Leu
                565                 570                 575

Leu Glu Glu Ser Lys Asp Ile Phe Phe Ser Ser Glu Phe Ile Asp Thr
            580                 585                 590

Ile Asn Lys Pro Val Asn Ala Ala Leu Phe Ile Asp Trp Ile Ser Lys
        595                 600                 605

Val Ile Arg Asp Phe Thr Thr Glu Ala Thr Gln Lys Ser Thr Val Asp
    610                 615                 620

Lys Ile Ala Asp Ile Ser Leu Ile Val Pro Tyr Val Gly Leu Ala Leu
625                 630                 635                 640

Asn Ile Ile Ile Glu Ala Glu Lys Gly Asn Phe Glu Glu Ala Phe Glu
                645                 650                 655

Leu Leu Gly Val Gly Ile Leu Leu Glu Phe Val Pro Glu Leu Thr Ile
            660                 665                 670

Pro Val Ile Leu Val Phe Thr Ile Lys Ser Tyr Ile Asp Ser Tyr Glu
        675                 680                 685

Asn Lys Asn Lys Ala Ile Lys Ala Ile Asn Asn Ser Leu Ile Glu Arg
    690                 695                 700
```

```
Glu Ala Lys Trp Lys Glu Ile Tyr Ser Trp Ile Val Ser Asn Trp Leu
705                 710                 715                 720

Thr Arg Ile Asn Thr Gln Phe Asn Lys Arg Lys Glu Gln Met Tyr Gln
            725                 730                 735

Ala Leu Gln Asn Gln Val Asp Ala Ile Lys Thr Ala Ile Glu Tyr Lys
            740                 745                 750

Tyr Asn Asn Tyr Thr Ser Asp Glu Lys Asn Arg Leu Glu Ser Glu Tyr
            755                 760                 765

Asn Ile Asn Asn Ile Glu Glu Glu Leu Asn Lys Lys Val Ser Leu Ala
            770                 775                 780

Met Lys Asn Ile Glu Arg Phe Met Thr Glu Ser Ser Ile Ser Tyr Leu
785                 790                 795                 800

Met Lys Leu Ile Asn Glu Ala Lys Val Gly Lys Leu Lys Lys Tyr Asp
            805                 810                 815

Asn His Val Lys Ser Asp Leu Leu Asn Tyr Ile Leu Asp His Arg Ser
            820                 825                 830

Ile Leu Gly Glu Gln Thr Asn Glu Leu Ser Asp Leu Val Thr Ser Thr
            835                 840                 845

Leu Asn Ser Ser Ile Pro Phe Glu Leu Ser
    850                 855
```

<210> SEQ ID NO 42
<211> LENGTH: 1337
<212> TYPE: DNA
<213> ORGANISM: Artificial Sequence
<220> FEATURE:
<223> OTHER INFORMATION: Synthetic polynucleotide sequence for the
      light chain of of C. botulinum Type G,
      optimized for expression in E. coli.

<400> SEQUENCE: 42

```
catatgccgg tcaatattaa gaacttcaat tacaacgacc cgatcaataa tgacgatatc      60
attatgatgg agccttttcaa cgacccaggt ccaggcacgt attacaaggc ttttcggatc    120
atcgaccgca tttggatcgt cccggagcgc ttcacgtacg gcttccaacc tgaccagttc    180
aatgcaagca caggggttttt cagcaaggac gtctacgagt actatgaccc aacttacctg    240
aagactgacg cggagaagga caaattcctg aagacgatga tcaagttgtt caaccgcatt    300
aactccaagc cgtccggcca cgactgctt gatatgattg tggacgccat cccttacctc    360
ggaaacgcct ctacgccacc ggacaagttc gcggcaaacg ttgcaaacgt gtccatcaac    420
aagaaaatta ttcagccggg ggccgaggac agattaagg gacttatgac taatctgatc    480
atcttcgggc cggggcctgt actctcggaa acttcacgg acagcatgat tatgaacggc    540
cattcaccga tctcagaagg attcggggca cgtatgatga tccggttctg cccgagttgc    600
ctcaacgtct tcaacaacgt ccaggaaaat aaggatacat cgatcttctc ccgccgtgcc    660
tacttcgcgg acccagcgtt aaccccttatg cacgagttaa tccacgtatt gcacggcctc    720
tacggcatta agatctcgaa cttacctatt accccaaaca cgaaagagtt cttcatgcaa    780
cacagcgacc cggttcaggc cgaggaatta tacaccttcg gcgggcacga cccaagtgtt    840
atctcaccgt ctaccgatat gaatatctac aacaaggccc tgcaaaactt ccaggacatc    900
gcaaaccggc ttaacattgt ctcatcggca caggggtctg gtatcgacat ctccctgtat    960
aagcagatct acaagaataa gtacgacttc gtagaagacc cgaacggcaa gtactcggtg   1020
gacaaggaca gtttgacaa actctacaaa gctctcatgt tcggttttcac agagacaaat   1080
cttgccggag agtacgggat caagacgcgg tactcgtatt tttccgagta cctgccgcct   1140
```

```
attaagacgg agaagttgct cgataacacc atttacactc agaatgaggg gttcaacatc      1200
gcctctaaga atctcaagac cgagttcaat ggtcagaaca aggcggtgaa caaagaggcg      1260
tatgaggaga ttagtctgga acacttggtg atctaccgaa ttgcgatgtg taagcctgtg      1320
atgtactaat aggatcc                                                    1337
```

```
<210> SEQ ID NO 43
<211> LENGTH: 444
<212> TYPE: PRT
<213> ORGANISM: Artificial Sequence
<220> FEATURE:
<223> OTHER INFORMATION: Recombinant protein encoded by SEQ ID NO:42
<221> NAME/KEY: UNSURE
<222> LOCATION: (442)...(443)
<223> OTHER INFORMATION: Any amino acid at each position
```

<400> SEQUENCE: 43

```
Met Pro Val Asn Ile Lys Asn Phe Asn Tyr Asn Asp Pro Ile Asn Asn
  1               5                  10                  15

Asp Asp Ile Ile Met Met Glu Pro Phe Asn Asp Pro Gly Pro Gly Thr
             20                  25                  30

Tyr Tyr Lys Ala Phe Arg Ile Ile Asp Arg Ile Trp Ile Val Pro Glu
         35                  40                  45

Arg Phe Thr Tyr Gly Phe Gln Pro Asp Gln Phe Asn Ala Ser Thr Gly
     50                  55                  60

Val Phe Ser Lys Asp Val Tyr Glu Tyr Tyr Asp Pro Thr Tyr Leu Lys
 65                  70                  75                  80

Thr Asp Ala Glu Lys Asp Lys Phe Leu Lys Thr Met Ile Lys Leu Phe
                 85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
    290                 295                 300
```

```
Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Xaa Xaa Asp
        435                 440
```

<210> SEQ ID NO 44
<211> LENGTH: 2547
<212> TYPE: DNA
<213> ORGANISM: Artificial Sequence
<220> FEATURE:
<223> OTHER INFORMATION: Synthetic polynucleotide sequence for the
      light chain with Hn segment of of C.
      botulinum Type G, optimized for expression
      in E. coli.

<400> SEQUENCE: 44

```
catatgccgg tcaatattaa gaacttcaat tacaacgacc cgatcaataa tgacgatatc        60
attatgatgg agccttttcaa cgacccaggt ccaggcacgt attacaaggc ttttcggatc       120
atcgaccgca tttggatcgt cccggagcgc ttcacgtacg gcttccaacc tgaccagttc       180
aatgcaagca caggggttttt cagcaaggac gtctacgagt actatgaccc aacttacctg      240
aagactgacg cggagaagga caaattcctg aagacgatga tcaagttgtt caaccgcatt      300
aactccaagc cgtccggcca gcgactgctt gatatgattg tggacgccat cccttacctc      360
ggaaacgcct ctacgccacc ggacaagttc gcggcaaacg ttgcaaacgt gtccatcaac      420
aagaaaatta ttcagccggg ggccgaggac cagattaagg gacttatgac taatctgatc      480
atcttcgggc cggggcctgt actctcggac aacttcacgg acagcatgat tatgaacggc      540 cattaccga tctcagaagg attcggggca cgtatgatga tccggttctg cccgagttgc       600
ctcaacgtct tcaacaacgt tccaggaaaat aaggatacat cgatcttctc ccgccgtgcc    660
tacttcgcgg acccagcgtt aacccttatg cacgagttaa tccacgtatt gcacggcctc     720
tacggcatta agatctcgaa cttacctatt accccaaaca cgaaagagtt cttcatgcaa      780
cacagcgacc cggttcaggc cgaggaatta taccttcg gcgggcacga cccaagtgtt       840
atctcaccgt ctaccgatat gaatatctac aacaaggccc tgcaaaactt ccaggacatc      900
gcaaaccggc ttaacattgt ctcatcggca caggggtctg gtatcgacat ctccctgtat      960
aagcagatct acaagaataa gtacgacttc gtagaagacc cgaacggcaa gtactcggtg     1020
gacaaggaca gtttgacaa actctacaaa gctctcatgt tcggttttcac agagacaaat   1080 cttgccggag agtacgggat caagacgcgg tactcgtatt tttccgagta cctgccgcct     1140
attaagacgg agaagttgct cgataacacc atttacactc agaatgaggg gttcaacatc     1200
```

```
gcctctaaga atctcaagac cgagttcaat ggtcagaaca aggcggtgaa caaagaggcg    1260
tatgaggaga ttagtctgga acacttggtg atctaccgaa ttgcgatgtg taagcctgtg    1320
atgtacaaga acaccggtaa gtccgagcag tgtatcatcg tcaacaacga ggacttgttc    1380
ttcatcgcca acaaggactc cttctccaag gacttggcca aggctgagac catcgcctac    1440
aacacccaga caacaccat cgagaacaac ttctccatcg accagctgat cttggacaac    1500
gacctgtcct ccggtatcga cctgccaaac gagaacaccg agccattcac caacttcgac    1560
gacatcgaca tcccagtcta catcaagcag tccgccctga gaagatctt cgtcgacggt    1620 gactccttgt tcgagtacct gcacgcccag accttcccat ccaacatcga gaaccagttg    1680
accaactccc tgaacgacgc tttgagaaac aacaacaagg tctacacctt cttctcccact    1740 aacttggtcg agaaggccaa cactgtcgtc ggtgcctcct tgttcgtcaa ctgggtcaag    1800
ggtgtcatcg acgacttcac ctccgagtcc acccaaaagt ccaccatcga caaggtctcc    1860
gacgtctcca tcatcatccc atacatcggt ccagccctga acgtcggtaa cgagaccgct    1920
aaggagaact tcaagaacgc cttcgagatc ggtggtgccg ccatcctgat ggagttcatc    1980
ccagagttga tcgtcccaat cgtcggtttc ttcaccttgg agtcctacgt cggtaacaag    2040
ggtcacatca tcatgaccat ctccaacgcc ctgaagaaga gagaccagaa gtggaccgac    2100
atgtacggtt tgatcgtctc ccagtggttg tccaccgtca cacccagtt ctacaccatc    2160 aaggagagaa tgtacaacgc cttgaacaac cagtcccagg ccatcgagaa gatcatcgag    2220
gaccagtaca accgttactc cgaggaggac aagatgaaca tcaacatcga cttcaacgac    2280
atcgacttca gctgaacca gtccatcaac ctggccatca acaacatcga cgacttcatc    2340
aaccagtgtt ccatctccta cctgatgaac cgtatgatcc cactggccgt caagaagttg    2400
aaggacttcg acgacaacct gaagcgtgac ctgctggagt acatcgacac caacgagttg    2460
tacctgctgg acgaggtcaa catcttgaag tccaaggtca cagacacttt gaaggactcc    2520
atcccattcg acttgtcctt gtacacc                                        2547
```

<210> SEQ ID NO 45
<211> LENGTH: 848
<212> TYPE: PRT
<213> ORGANISM: Artificial Sequence
<220> FEATURE:
<223> OTHER INFORMATION: Recombinant protein encoded by SEQ ID NO:44

<400> SEQUENCE: 45

```
Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
```

```
            115                 120                 125
Phe Ala Ala Asn Val Ala Asn Val Ser Ile Asn Lys Lys Ile Ile Gln
130                 135                 140
Pro Gly Ala Glu Asp Gln Ile Lys Gly Leu Met Thr Asn Leu Ile Ile
145                 150                 155                 160
Phe Gly Pro Gly Pro Val Leu Ser Asp Asn Phe Thr Asp Ser Met Ile
                    165                 170                 175
Met Asn Gly His Ser Pro Ile Ser Glu Gly Phe Gly Ala Arg Met Met
                180                 185                 190
Ile Arg Phe Cys Pro Ser Cys Leu Asn Val Phe Asn Asn Val Gln Glu
            195                 200                 205
Asn Lys Asp Thr Ser Ile Phe Ser Arg Arg Ala Tyr Phe Ala Asp Pro
210                 215                 220
Ala Leu Thr Leu Met His Glu Leu Ile His Val Leu His Gly Leu Tyr
225                 230                 235                 240
Gly Ile Lys Ile Ser Asn Leu Pro Ile Thr Pro Asn Thr Lys Glu Phe
                    245                 250                 255
Phe Met Gln His Ser Asp Pro Val Gln Ala Glu Glu Leu Tyr Thr Phe
                260                 265                 270
Gly Gly His Asp Pro Ser Val Ile Ser Pro Ser Thr Asp Met Asn Ile
            275                 280                 285
Tyr Asn Lys Ala Leu Gln Asn Phe Gln Asp Ile Ala Asn Arg Leu Asn
            290                 295                 300
Ile Val Ser Ser Ala Gln Gly Ser Gly Ile Asp Ile Ser Leu Tyr Lys
305                 310                 315                 320
Gln Ile Tyr Lys Asn Lys Tyr Asp Phe Val Glu Asp Pro Asn Gly Lys
                    325                 330                 335
Tyr Ser Val Asp Lys Asp Lys Phe Asp Lys Leu Tyr Lys Ala Leu Met
                340                 345                 350
Phe Gly Phe Thr Glu Thr Asn Leu Ala Gly Glu Tyr Gly Ile Lys Thr
            355                 360                 365
Arg Tyr Ser Tyr Phe Ser Glu Tyr Leu Pro Pro Ile Lys Thr Glu Lys
370                 375                 380
Leu Leu Asp Asn Thr Ile Tyr Thr Gln Asn Glu Gly Phe Asn Ile Ala
385                 390                 395                 400
Ser Lys Asn Leu Lys Thr Glu Phe Asn Gly Gln Asn Lys Ala Val Asn
                    405                 410                 415
Lys Glu Ala Tyr Glu Glu Ile Ser Leu Glu His Leu Val Ile Tyr Arg
                420                 425                 430
Ile Ala Met Cys Lys Pro Val Met Tyr Lys Asn Thr Gly Lys Ser Glu
            435                 440                 445
Gln Cys Ile Ile Val Asn Asn Glu Asp Leu Phe Phe Ile Ala Asn Lys
450                 455                 460
Asp Ser Phe Ser Lys Asp Leu Ala Lys Ala Glu Thr Ile Ala Tyr Asn
465                 470                 475                 480
Thr Gln Asn Asn Thr Ile Glu Asn Asn Phe Ser Ile Asp Gln Leu Ile
                    485                 490                 495
Leu Asp Asn Asp Leu Ser Ser Gly Ile Asp Leu Pro Asn Glu Asn Thr
                500                 505                 510
Glu Pro Phe Thr Asn Phe Asp Asp Ile Asp Ile Pro Val Tyr Ile Lys
            515                 520                 525
Gln Ser Ala Leu Lys Lys Ile Phe Val Asp Gly Asp Ser Leu Phe Glu
530                 535                 540
```

-continued

```
Tyr Leu His Ala Gln Thr Phe Pro Ser Asn Ile Glu Asn Gln Leu Thr
545                 550                 555                 560

Asn Ser Leu Asn Asp Ala Leu Arg Asn Asn Lys Val Tyr Thr Phe
            565                 570                 575

Phe Ser Thr Asn Leu Val Glu Lys Ala Asn Thr Val Val Gly Ala Ser
            580                 585                 590

Leu Phe Val Asn Trp Val Lys Gly Val Ile Asp Asp Phe Thr Ser Glu
595                 600                 605

Ser Thr Gln Lys Ser Thr Ile Asp Lys Val Ser Asp Val Ser Ile Ile
    610                 615                 620

Ile Pro Tyr Ile Gly Pro Ala Leu Asn Val Gly Asn Glu Thr Ala Lys
625                 630                 635                 640

Glu Asn Phe Lys Asn Ala Phe Glu Ile Gly Gly Ala Ala Ile Leu Met
                645                 650                 655

Glu Phe Ile Pro Glu Leu Ile Val Pro Ile Val Gly Phe Phe Thr Leu
                660                 665                 670

Glu Ser Tyr Val Gly Asn Lys Gly His Ile Ile Met Thr Ile Ser Asn
            675                 680                 685

Ala Leu Lys Lys Arg Asp Gln Lys Trp Thr Asp Met Tyr Gly Leu Ile
690                 695                 700

Val Ser Gln Trp Leu Ser Thr Val Asn Thr Gln Phe Tyr Thr Ile Lys
705                 710                 715                 720

Glu Arg Met Tyr Asn Ala Leu Asn Asn Gln Ser Gln Ala Ile Glu Lys
                725                 730                 735

Ile Ile Glu Asp Gln Tyr Asn Arg Tyr Ser Glu Glu Asp Lys Met Asn
            740                 745                 750

Ile Asn Ile Asp Phe Asn Asp Ile Asp Phe Lys Leu Asn Gln Ser Ile
            755                 760                 765

Asn Leu Ala Ile Asn Asn Ile Asp Asp Phe Ile Asn Gln Cys Ser Ile
770                 775                 780

Ser Tyr Leu Met Asn Arg Met Ile Pro Leu Ala Val Lys Lys Leu Lys
785                 790                 795                 800

Asp Phe Asp Asp Asn Leu Lys Arg Asp Leu Leu Glu Tyr Ile Asp Thr
                805                 810                 815

Asn Glu Leu Tyr Leu Leu Asp Glu Val Asn Ile Leu Lys Ser Lys Val
            820                 825                 830

Asn Arg His Leu Lys Asp Ser Ile Pro Phe Asp Leu Ser Leu Tyr Thr
835                 840                 845
```

<210> SEQ ID NO 46
<211> LENGTH: 7
<212> TYPE: PRT
<213> ORGANISM: Artificial Sequence
<220> FEATURE:
<223> OTHER INFORMATION: Synthetic peptide; competitive inhibitor of
      Zn protease

<400> SEQUENCE: 46

```
Cys Arg Ala Thr Lys Met Leu
1               5
```

<210> SEQ ID NO 47
<211> LENGTH: 449
<212> TYPE: PRT
<213> ORGANISM: Artificial Sequence
<220> FEATURE:
<223> OTHER INFORMATION: Synthetic botulinum neurotoxin light chain of serotype A based on wild-type Clostridium
botulinum sequence

<400> SEQUENCE: 47

| Met | Val | Gln | Phe | Val | Asn | Lys | Gln | Phe | Asn | Tyr | Lys | Asp | Pro | Val | Asn |
| 1 | | | | 5 | | | | | 10 | | | | | 15 | |

| Gly | Val | Asp | Ile | Ala | Tyr | Ile | Lys | Ile | Pro | Asn | Val | Gly | Gln | Met | Gln |
| | | | 20 | | | | | 25 | | | | | 30 | | |

| Pro | Val | Lys | Ala | Phe | Lys | Ile | His | Asn | Lys | Ile | Trp | Val | Ile | Pro | Glu |
| | | 35 | | | | | 40 | | | | | 45 | | | |

| Arg | Asp | Thr | Phe | Thr | Asn | Pro | Glu | Glu | Gly | Asp | Leu | Asn | Pro | Pro | Pro |
| | 50 | | | | | 55 | | | | | 60 | | | | |

| Glu | Ala | Lys | Gln | Val | Pro | Val | Ser | Tyr | Tyr | Asp | Ser | Thr | Tyr | Leu | Ser |
| 65 | | | | | 70 | | | | 75 | | | | | | 80 |

| Thr | Asp | Asn | Glu | Lys | Asp | Asn | Tyr | Leu | Lys | Gly | Val | Thr | Lys | Leu | Phe |
| | | | | 85 | | | | | 90 | | | | | 95 | |

| Glu | Arg | Ile | Tyr | Ser | Thr | Asp | Leu | Gly | Arg | Met | Leu | Leu | Thr | Ser | Ile |
| | | | | 100 | | | | | 105 | | | | | 110 | |

| Val | Arg | Gly | Ile | Pro | Phe | Trp | Gly | Gly | Ser | Thr | Ile | Asp | Thr | Glu | Leu |
| | | | 115 | | | | | 120 | | | | | 125 | | |

| Lys | Val | Ile | Asp | Thr | Asn | Cys | Ile | Asn | Val | Ile | Gln | Pro | Asp | Gly | Ser |
| | 130 | | | | | 135 | | | | | 140 | | | | |

| Tyr | Arg | Ser | Glu | Glu | Leu | Asn | Leu | Val | Ile | Ile | Gly | Pro | Ser | Ala | Asp |
| 145 | | | | | 150 | | | | | 155 | | | | | 160 |

| Ile | Ile | Gln | Phe | Glu | Cys | Lys | Ser | Phe | Gly | His | Glu | Val | Leu | Asn | Leu |
| | | | | 165 | | | | | 170 | | | | | 175 | |

| Thr | Arg | Asn | Gly | Tyr | Gly | Ser | Thr | Gln | Tyr | Ile | Arg | Phe | Ser | Pro | Asp |
| | | | 180 | | | | | 185 | | | | | 190 | | |

| Phe | Thr | Phe | Gly | Phe | Glu | Glu | Ser | Leu | Glu | Val | Asp | Thr | Asn | Pro | Leu |
| | | | 195 | | | | | 200 | | | | | 205 | | |

| Leu | Gly | Ala | Gly | Lys | Phe | Ala | Thr | Asp | Pro | Ala | Val | Thr | Leu | Ala | His |
| | 210 | | | | | 215 | | | | | 220 | | | | |

| Glu | Leu | Ile | His | Ala | Gly | His | Arg | Leu | Tyr | Gly | Ile | Ala | Ile | Asn | Pro |
| 225 | | | | | 230 | | | | | 235 | | | | | 240 |

| Asn | Arg | Val | Phe | Lys | Val | Asn | Thr | Asn | Ala | Tyr | Tyr | Glu | Met | Ser | Gly |
| | | | | 245 | | | | | 250 | | | | | 255 | |

| Leu | Glu | Val | Ser | Phe | Glu | Glu | Leu | Arg | Thr | Phe | Gly | Gly | His | Asp | Ala |
| | | | 260 | | | | | 265 | | | | | 270 | | |

| Lys | Phe | Ile | Asp | Ser | Leu | Gln | Glu | Asn | Glu | Phe | Arg | Leu | Tyr | Tyr | Tyr |
| | | | 275 | | | | | 280 | | | | | 285 | | |

| Asn | Lys | Phe | Lys | Asp | Ile | Ala | Ser | Thr | Leu | Asn | Lys | Ala | Lys | Ser | Ile |
| | 290 | | | | | 295 | | | | | 300 | | | | |

| Val | Gly | Thr | Thr | Ala | Ser | Leu | Gln | Tyr | Met | Lys | Asn | Val | Phe | Lys | Glu |
| 305 | | | | | 310 | | | | | 315 | | | | | 320 |

| Lys | Tyr | Leu | Leu | Ser | Glu | Asp | Thr | Ser | Gly | Lys | Phe | Ser | Val | Asp | Lys |
| | | | | 325 | | | | | 330 | | | | | 335 | |

| Leu | Lys | Phe | Asp | Lys | Leu | Tyr | Lys | Met | Leu | Thr | Glu | Ile | Tyr | Thr | Glu |
| | | | 340 | | | | | 345 | | | | | 350 | | |

| Asp | Asn | Phe | Val | Lys | Phe | Phe | Lys | Val | Leu | Asn | Arg | Lys | Thr | Tyr | Leu |
| | | | 355 | | | | | 360 | | | | | 365 | | |

| Asn | Phe | Asp | Lys | Ala | Val | Phe | Lys | Ile | Asn | Ile | Val | Pro | Lys | Val | Asn |
| | 370 | | | | | 375 | | | | | 380 | | | | |

| Tyr | Thr | Ile | Tyr | Asp | Gly | Phe | Asn | Leu | Arg | Asn | Thr | Asn | Leu | Ala | Ala |
| 385 | | | | | 390 | | | | | 395 | | | | | 400 |

```
Asn Phe Asn Gly Gln Asn Thr Glu Ile Asn Asn Met Asn Phe Thr Lys
                405                 410                 415

Leu Lys Asn Phe Thr Gly Leu Phe Glu Phe Tyr Lys Leu Leu Cys Val
            420                 425                 430

Arg Gly Ile Ile Thr Ser Lys Thr Lys Ser Leu Asp Lys Gly Tyr Asn
            435                 440                 445

Lys
```

RECOMBINANT LIGHT CHAINS OF BOTULINUM NEUROTOXINS AND LIGHT CHAIN FUSION PROTEINS FOR USE IN RESEARCH AND CLINICAL THERAPY

This application is a continuation-in-part of U.S. patent application Ser. No. 09/910,186 filed Jul. 20, 2001, which is a continuation of U.S. patent application Ser. No. 09/611, 419 filed Jul. 6, 2000, which is a continuation of U.S. patent application Ser. No. 08/123,975, filed Sep. 21, 1993, now abandoned, wherein said application 09/611,419 is based on U.S. Provisional Applications Nos. 60/133,866, 60/133,868, 60/133,869, 60/133,865, 60/133,873, and 60/133,867, all filed May 12, 1999, all of which are incorporated herein by reference in their entirety. The instant application is also based on U.S. Provisional Application No. 60/246,774, filed on Nov. 6, 2000, and U.S. Provisional Application No. 60/311,966 filed Aug. 6, 2001, which are incorporated herein in their entirety by reference.

FIELD OF THE INVENTION

The invention is directed to construction, expression, and purification of synthetic DNA molecules encoding polypeptides comprising botulinum neutrotoxin (BoNT) light chains. The invention is also directed to methods of vaccination against botulism using the expressed peptides.

BACKGROUND OF THE INVENTION

The sporulating, obligate anaerobic, grain-positive bacillus Clostridium produces eight forms of antigenically distinct exotoxins. Tetanus neurotoxin (TeNT) is produced by Clostridium tetani while Clostridium botulinum produces seven different neurotoxins which are differentiated serologically by specific neutralization. The botulinum neurotoxins (BoNT) have been designated as serotypes A, B, $C_1$, E, F, and G. Botulinum neurotoxins (BoNT) are the most toxic substances known and are the causative agents of the disease botulism. BoNT exert their action by inhibiting the release of the neurotransmitter acetylcholine at the neuromuscular junction (Habermann, E, et al., (1986), "Clostridial Neurotoxins: Handling and Action at the Cellular and Molecular Level," *Cur. Top. Microbiol. Immunol.*, 129: 93–179; Schiavo, G., et al., (1992a), "Tetanus and Botulinum-B Neurotoxins Block Neurotransmitter Release by Proteolytic Cleavage of Synaptobrevin," *Nature*, 359:832–835; Simpson, L. L., (1986), "Molecular Pharmacology of Botulinum Toxin and Tetanus Toxin," *Annu. Rev. Pharmacol. Taxicol.*, 26:427–453) which leads to a state of flaccid paralysis. Indeed, only a few molecules of toxin are required to abolish the action of a nerve cell. Polyclonal antibodies derived from a specific neurotoxin can neutralize the toxic effects of that toxin but will not cross-neutralize another toxin serotype. Thus, to protect against all seven toxins, one needs seven vaccines.

Human botulism poisoning is generally caused by type A, B, E or rarely, by type F toxin. Type A and B are highly poisonous proteins which resist digestion by the enzymes of the gastrointestinal tract. Foodborne botulism poisoning is caused by the toxins present in contaminated food, but wound and infant botulism are caused by in vivo growth in closed wounds and the gastrointestinal tract respectively. The toxins primarily act by inhibiting the neurotransmitter acetylcholine at the neuromuscular junction, causing paralysis. Another means for botulism poisoning to occur is the deliberate introduction of the toxin(s) into the environment as might occur in biological warfare or a terrorist attack. When the cause of botulism is produced by toxin rather than by in vivo infection the onset of neurologic symptoms is usually abrupt and occurs within 18 to 36 hours after ingestion. The most common immediate cause of death is respiratory failure due to diaphragmatic paralysis. Home canned foods are the most common sources of toxins. The most frequently implicated toxin is toxin A, which is responsible for more than 50% of morbidity resulting from *botulinum* toxin.

Botulinum and tetanus neurotoxins are a new class of zinc-endopeptidases that act selectively at discrete sites on three synaptosomal proteins of the neuroexocytotic apparatus. See Montecucco and Schiavo, 1995, and Schiavo, 1995, for review. These neurotoxins are the most potent of all the known toxins. The *botulinum* neurotoxins (BoNT), designed A–G, produced by seven immunologically distinct strains of *Clostridium botulinum* cause death by flaccid muscle paralysis at the neuromuscular junction. Extreme toxicity of these toxins and their lability in purified preparations have limited any detailed characterizations.

These neurotoxins are expressed as 150-kDa single polypeptides (termed dichains) containing a disulfide bond between the 50-kDa N-terminal light chain (LC) and the 100-kDa C-terminal heavy chain (HC). A post-translational cryptic cleavage generates the two chains connected by a disulfide bond. The LC contains the toxic, zinc-endopeptidase catalytic domain. The 100-kDa HC may be further proteolyzed into a 50-kDa N-terminal membrane-spanning domain ($H_n$) and a 50-kDa C-terminal receptor-binding domain ($H_c$).

With three functional domains, the mechanism of action of these neurotoxins is multiphasic: (1) The $H_c$ domain plays a role in binding the toxins to specific receptors located exclusively on the peripheral cholinergic nerve endings (Black and Dolly, 1986). (2) The $H_n$ domain is believed to participate in a receptor-mediated endocytotic pore formation in an acidic environment, allowing translocation of the catalytic LC into the cytosol. Reducing the disulfide bond connecting the LC with the H upon exposure to the cytosol or within the acidic endosome (Montal et al., 1992) releases the catalytic LC into the cytosol. (3) The LC then cleaves at specific sites of one of the three different soluable NSF attachment protein receptor (SNARE) proteins, synaptobrevin, syntaxin, or synaptosomal associated protein of 25 kDa (SNAP-25) (Blasi et al., 1993; Schiavo et al., 1993, 1994; Shone et al., 1993; Foran et al., 1996). These proteins are essential for synaptic vesicle fusion in exocytosis. Their proteolysis inhibits exocytosis and blocks acetylcholine secretion, leading ultimately to muscular paralysis. The LC itself is nontoxic because it cannot translocate through the cholinergic nerve ending into the cytosol. However, in digitonin-permeabilized chromaffin cells, the LC inhibits exocytosis (Bittner et al., 1989), and direct microinjection of the LC into the cytosol results in blockage of membrane exocytosis (Bittner et al., 1989; Bi et al., 1995).

The LC of all known clostridial neurotoxins contain the sequence HExxH that is characteristic of zinc-endoproteinases (Thompson et al., 1990). The essential role of zinc on the structure and catalysis of the neurotoxins is established (Fu et al., 1998). A unique feature of the neurotoxins' protease activity is their substrate requirement. Short peptides encompassing only the cleavage sites are not hydrolyzed (Foran et al., 1994; Shone and Roberts, 1994). A specific secondary and/or tertiary structure of the substrate is most probably recognized (Washbourne et al., 1997; Lebeda and Olson, 1994; Rossetto et al., 1994) rather than a primary structure alone, as is the case with most other proteases. Most importantly, their identified natural substrates are proteins involved in the fundamental process of exocytosis (Blasi et al., 1993; Schiavo et al., 1993, 1994; Shone et al., 1993; Foran et al., 1996). Light chain also is the target of an intensive effort to design drugs, inhibitors, and vaccines. A detailed understanding of its structure and function is thus very important.

The present invention describes the construction and overexpression of a synthetic gene for the nontoxic LC of BoNT/A in *E. coli*. The high level of expression obtained enabled purification of gram quantities of LC from 1 L of culture as well as extensive characterization. The preparation of the rBoNT/A LC was highly soluble, stable at 4° C. for at least 6 months, and had the expected enzymatic and functional properties. For the first time, a cysteine residue was tentatively identified in the vicinity of the active site which, when modified by mercuric compounds, led to complete loss of enzymatic activity.

The BoNTs and their LCs are targets of vaccine development, drug design, and mechanism studies because of their potential role in biological warfare, wide therapeutic applications, and potential to facilitate elucidation of the mechanism of membrane exocytosis. In spite of such immense importance, studies of the LC have been limited by its availability. Commercially available LC is prepared by separating it from the dichain toxins under denaturing conditions. These preparations therefore retain some contaminating toxicity of the dichain, have low solubility, and often begin to proteolytically degrade and start losing activity within hours of storage in solution.

The LC of serotype A has been separated and purified from the full-length toxin by QAE-Sephadex chromatography from 2 M urea; however, the preparation suffers from low solubility (Shone and Tranter, 1995). The LC of serotype C was similarly obtained at a level of <5 mg/10 L culture of *C. botulinum* (Syuto and Kubo, 1981). These preparations almost invariably contain contaminating full-length toxins, and the commercially available preparations precipitate from solution or undergo proteolytic degradation upon hours of storage in solution. More recently the LC of tetanus neurotoxin (Li et al., 1994) and of BoNT/A (Zhou et al., 1995) were expressed in *E. coli* as maltose-binding proteins and purified in 0.5 mg quantities from 1-L cultures (Zhou et al., 1995). However, the poor expression of the cloned products, probably due to rare codon usage in clostridial DNA (Makoff et al., 1989, Winkler and Wood, 1988), remained a major hurdle in obtaining adequate amount of the protein for structural and functional studies.

Most of the clostridial strains contain specific endogenous proteases which activate the toxins at a protease-sensitive loop located approximately one third of the way into the molecule from the amino-terminal end. Upon reduction and fractionation (electrophoretically or chromatographically), the two chains can be separated; one chain has a Mr of ~100 kDa and is referred to as the heavy chain while the other has a Mr ~50 kDa and is termed the light chain.

The mechanism of nerve intoxication is accomplished through the interplay of three key events, each of which is performed by a separate portion of the neurotoxin protein. First, the carboxy half of the heavy chain (fragment C or $H_c$ is required for receptor-specific binding to cholinergic nerve cells (Black, J. D., et al., (1986), "Interaction of $^{125}$I-botulinum Neurotoxins with Nerve Terminals. I. Ultrastructural Autoradiographic Localization and Quantitation of Distinct Membrane Acceptors for Types A and B on Motor Nerves," *J. Cell Biol.*, 103:521–534; Nishiki, T.-I., et al., (1994), "Identification of Protein Receptor for *Clostridium botulinum* Type B Neurotoxin in Rat Brain Synaptosomes," *J. Biol. Chem.*, 269:10498–10503; Shone, C. C., et al., (1985), "Inactivation of *Clostridium botulinum* Type A Neurotoxin by Trypsin and Purification of Two Tryptic Fragments. Proteolytic Action Near the COOH-terminus of the Heavy Subunit Destroys Toxin-Binding Activity, *Eur. J. Biochem.*, 151:75–82). Evidence suggests that polysialogangliosides (van Heyningen, W. E., (1968), "Tetanus," *Sci. Am.*, 218:69–77) could act as receptors for the toxins but the data supporting a specific receptor remains equivocal (Middlebrook, J. L., (1989), "Cell Surface Receptors for Protein Toxins," *Botulinum Neurotoxins and Tetanus Toxin*, (Simpson, L. L., Ed.) pp. 95–119, Academic Press, New York). After binding, the toxin is internalized into an endosome through receptor-mediated endocytosis (Shone, C. C., et al., (1987), "A 50-kDa Fragment from the $NH_2$-terminus of the Heavy Subunit of *Clostridium botulinum* Type A Neurotoxin Forms Channels in Lipid Vesicles, *Euro. J. Biochem.*, 167:175–180).

The amino terminal half of the heavy chain is believed to participate in the translocation mechanism of the light chain across the endosomal membrane (Simpson, 1986; Poulain, B., et al., (1991), "Heterologous Combinations of Heavy and Light Chains from *Botulinum* Neurotoxin A and Tetanus Toxin Inhibit Neurotransmitter Release in *Aplysia*," *J. Biol. Chem.*, 266:9580–9585; Montal, M. S., et al., (1992), "Identification of an Ion Channel-Forming Motif in the Primary Structure of Tetanus and *Botulinum* Neurotoxins," *FEBS*, 313:12–18). The low pH environment of the endosome may trigger a conformational change in the translocation domain, thus forming a channel for the light chain.

The final event of intoxication involves enzymatic activity of the light chain, a zinc-dependent endoprotease (Schiavo, 1992a; Schiavo, G., et al., (1992b), "Tetanus Toxin is a Zinc Protein and its Inhibition of Neurotransmitter Release and Protease Activity Depend on Zinc," *EMBO J*, 11:3577–3583), on key synaptic vesicle proteins (Schiavo, 1992a; Oguma, K., et al., (1995), "Structure and Function of *Clostridium botulinum* Toxins," *Microbiol. Immunol.*, 39:161–168; Schiavo, G., et al., (1993), "Identification of the Nerve Terminal Targets of *Botulinum* Neurotoxin Serotypes A, D, and E," *J. Biol. Chem.*, 268:23784–23787; Shone, C. C., et al., (1993), "Proteolytic Cleavage of Synthetic Fragments of Vesicle-Associated Membrane Protein, Isoform-2 by *Botulinum* Type B Neurotoxin," *Eur. J. Biochem.*, 217:965–971) necessary for neurotransmitter release. The light chains of BoNT serotypes A, $C_1$, and E cleave SNAP-25 (synaptosomal-associated protein of M25,000), serotypes B, D, F, and G cleave vessicle-associated membrane protein (VAMP)/synaptobrevin (synaptic vesicle-associated membrane protein); and serotype $C_1$ cleaves syntaxin. Inactivation of SNAP-25, VAMP, or syntaxin by BoNT leads to an inability of the nerve cells to release acetylcholine resulting in neuromuscular paralysis and possible death, if the condition remains untreated.

The majority of research related to *botulinum* toxin has focused on the development of vaccines. Currently, a pentavalent toxoid vaccine against serotypes A through E (Anderson, J. H., et al., (1981), "Clinical Evaluation of *Botulinum* Toxoids," *Biomedical Aspects of Botulism*, (Lewis, G. E., Ed.), pp. 233–246, Academic Press, New York; Ellis, R. J., (1982), "Immunobiologic Agents and Drugs Available from the Centers for Disease Control. Descriptions, Recommendations, Adverse Reactions and Scrologic Response," 3rd ed., Centers for Disease Control. Atlanta, Ga.; Fiock, M. A., et al., (1963), "Studies of Immunities to Toxins of *Clostridium botulinum*. IX. Immunologic Response of Man to Purified Pentavalent ABCDE *Botulinum* Toxoid," *J. Immunol.*, 90:697–702; Siegel, L. S., (1988), "Human Immune Response to *Botulinum* Pentavalent (ABCDE) Toxoid Determined by a Neutralization Test and by an Enzyme-Linked Immunosorbent Assay," *J. Clin. Microbiol.*, 26:2351–2356), available under Investigational New Drug (IND) status, is used to immunize specific populations of at-risk individuals, i.e., scientists and health care providers who handle BoNT and military personnel who may be subjected to weaponized forms of the toxin. Though serotypes A, B, and E are most associated with botulism outbreaks in humans, type F has also been diagnosed (Midura, T. F., et al., (1972), "*Clostridium botulinum* Type F: Isolation from Venison Jerky," *Appl. Microbiol.*, 24:165–167; Green, J., et al., (1983), "Human Botulism (Type F)—A Rare Type," *Am. J. Med.*, 75:893–895; Sonnabend, W. F., et al., (1987), "Intestinal Toxicoinfection by *Clostridium botulinum* Type F in an Adult. Case Associated with Guillian-Barre Syndrome," *Lancet*, 1:357–361; Hatheway, C. L., (1976), "Toxoid of *Clostridium botulinum* Type F: Purification and Immunogenicity Studies," *Appl. Environ. Microbiol.*, 31:234–242). A separate monovalent toxoid vaccine against BoNTF is available under IND status. Hatheway demonstrated that the BoNTF toxoid could protect guinea pigs against a homologous challenge (Wadsworth, J. D. F., et al., (1990), "*Botulinum* Type F Neurotoxin," *Biochem. J.*, 268:123–128).

New-generation, recombinant vaccines have also been developed by USAMRIID (e.g. Dertzbaugh M T, Sep. 11, 2001, U.S. Pat. No. 6,287,566; U.S. Appln. Ser. No. 09/910, 186 filed Jul. 20, 2001; and U.S. Application. Ser. No. 09/611,419 filed Jul. 6, 2000) and commercial sources (e.g. Ophidian Pharmaceuticals, Inc. Williams J A, Jul. 6, 1999, U.S. Pat. No. 5,919,665; using clones supplied by USAMRIID).

Most vaccine studies have focused on the *botulinum* toxin heavy chain, leaving the light chain largely ignored. In 1995, Zhou et al. discovered that a single mutation in the light chain of *botulinum* neurotoxin serotype A abolished its neurotoxicity and its ability to cleave SNAP-25, one of the natural substrates, when reconstituted with the heavy chain. See Zhou, L. et al., (1995), "Expression and Purification of *Botulinum* Neurotoxin A: A Single Mutation Abolishes its Cleavage of SNAP-25 and Neurotoxicity after Reconstitution with the Heavy Chain," *Biochem.*, 34:15175–15181.) This raised the possibility that the mutated light chain might have various research or therapeutic uses. Further research produced a recombinant light chain (Li, L. and Singh, B. R., (1999), "High-Level Expression, Purification, and Characterization of Recombinant Type A *Botulinum* Neurotoxin Light Chain," *Protein Expression and Purification*, 17:339–344) and a construct comprising the minimum essential light chain domain (Kadkhodayan, S., et al., (2000), "Cloning, Expression, and One-Step Purification of the Minimal Essential Domain of the Light Chain of *Botulinum* Neurotoxin Type A," *Protein Expression and Purification*, 19:125–130).

Recombinant production methods alleviate many of the problems associated with the toxoid, such as the need for a dedicated manufacturing facility. Presently, many cGMP facilities are in existence and available that could manufacture a recombinant product. There would be no need to culture large quantities of a hazardous toxin-producing bacterium. Production yields from a genetically engineered product are expected to be high. Recombinant products would be purer, less reactogenic, and more fully characterized. Thus, the cost of a recombinant product would be expected to be much lower than a toxoid because there would be no expenditures required to support a dedicated facility, and the higher production yields would reduce the cost of therapeutic and research products.

However, recombinant methods as described in the publications above do not yield optimal results because *botulinum* codons are not translated well in other organisms commonly used for production, such as *E. coli* or yeast. Furthermore, no easily translatable, recombinant form of the non-neurotoxic, mutated light chain presently exists. Recombinant forms of both functional and non-neurotoxic *botulinum* neurotoxin that may be translated efficiently in either *E. coli* or yeast are needed for research and therapeutic purposes.

Commercially available BoNT LC is prepared by separation from the di-chain toxins. These preparations, therefore, retain some contaminating toxicity, have low solubility, and undergo proteolytic degradation within hours and days of storage in solution. Many clinical disorders are presently being treated with a *botulinum* neurotoxin complex that is isolated from the bacterium, *Clostridium botulinum*. There is no data to demonstrate that the binding proteins play any role in the therapeutic effects of the drug. The binding proteins, however, probably contribute to the immunological response in those patients that become non-responsive to drug treatment. Recombinant products could be manufactured under conditions that are more amenable to product characterization. Chimeras of the drug product could also be produced by domain switching. Chimeras could potentially increase the number of potential useful drug products.

Recently, the BoNT LC of serotype A has been expressed as a maltose-binding protein and purified in 0.5 mg quantities from 1 liter culture (Zhou et a., 1995). The poor expression of the native gene was probably due to the high A+T composition found in the clostridial DNA.

SUMMARY OF THE INVENTION

The present invention relates to the design and construction of synthetic DNA molecules that encode one of the seven light chains of *Clostridium botulinum* neurotoxin and are capable of being expressed in heterologous prokaryotic or eukaryotic hosts. The invention is based, in part, on modifying the wild-type BoNT sequence according to the codon usage normally found in genes that are highly expressed in the host organism. By selecting codons rich in G+C content, the synthetic DNA molecules may further be designed to lower the high A+T rich base composition found in clostridial genes.

The invention further relates to methods of expressing and purifying recombinant BoNT light chains. According to the invention, BoNT LC may be expressed in a heterologous host system by itself or as a fusion to another protein or carrier. For example, the BoNT LC may be fused to a synthetic or wild-type BoNT heavy chain or a fragment thereof. BoNT LC of the invention may or may not have catalytic activity as a zinc protease. In some embodiments of the invention, catalytically inactive BoNT LC is fused to a BoNT heavy chain forming a mutant holotoxin. Non-enzymatic, non-toxic mutant holotoxins are capable of being internalized into nerve cells. In addition, mutant holotoxins may be used as transporters to carry other molecules into colinergic nerve cells.

The invention further provides methods and compositions for eliciting an immune response to BoNT LC and BoNT HN. The invention provides preparations of BoNT LC and BoNT HN that are capable of eliciting protective immunity in a mammal.

BRIEF DESCRIPTION OF THE DRAWINGS

FIG. 3. UV-visible absorption spectrum of the rBoNT/A LC.

FIG. 4. Long-term stability at 4° C. (A) and thermal stability (B) of the rBoNT/A LC. (A) Aliquots of the LC from one single preparation were assayed at the indicated times; (B) 50 μl aliquots of the LC in buffer G containing 1 mM DTT and 50 μM $ZnCl_2$ were taken in Eppendorf tubes and heated for 5 min at the indicated temperatures. After cooling on ice for 60 min, the supernatants were assayed for proteolytic activity.

FIG. 18. Purification of LcA, LcA+Belt, and LcA+Hn from *E. coli* cells.

DETAILED DESCRIPTION OF THE INVENTION

Figures 1, 2:
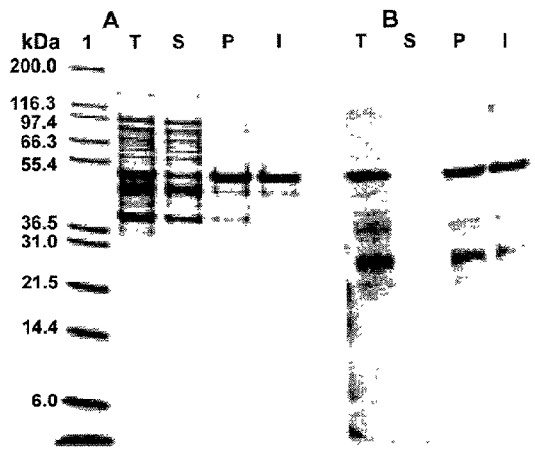
FIG. 1. Nucleotide sequence of rBoNT/A LC and the corresponding amino acid sequence. The codon in italics (i.e., encoding the penultimate Val residue) and at the 5' end of the gene was introduced to create and maintain the Nco I restriction enzyme site. Codons in italics (i.e., encoding LVPRGS; residues 450–455 of SEQ ID NO:5) at the 3' end of the gene encode a thrombin protease cleavage site for removing the His tag after purification.
FIG. 2. SDS-PAGE followed by Coomassie stain (A) and Western blot (B) of crude and purified BoNT/A LC expressed in *E. coli* containing the synthetic gene for BoNT/A LC in a multicopy plasmid pET24. Total cellular protein (T), soluble supernatant (S), insoluble pellet (P), and purified inclusion bodies (I) were prepared as described in Section 2. Lane 1 shows Novex wide-range molecular-mass markers (0.8–3.0 μg/band). The sarkosyl solubilized inclusion bodies of the LC had the same electrophoretic behavior as (I). About 20 μg of protein was applied per lane. Western blot used affinity-purified rabbit polyclonal antibodies against a 16-residue N-terminal sequence of the BoNT/A LC as the primary antibody and a peroxidase-coupled goat anti-rabbit IgG (H+L) as the secondary antibody. Bands were visualized by a chromogenic substrate.

In some embodiments the invention provides methods and nucleic acids for expressing *Clostridium botulinum* genes in other prokaryotes and eukaryotes. More specifically, the invention provides methods and nucleic acids for expressing *botulinum* neurotoxin (BoNT) light chains (LC) in *Escherichia coli* or *Pichia pastoris*. In order to be expressed in *Escherichia coli* or *Pichia pastoris*, the sequence of DNA encoding wild-type BoNT LC is engineered to replace some *Clostridium* codons that are rare or unrecognized in the host organism and to reduce the A+T content. The recombinant or synthetic DNA molecules of the invention are preferably designed with codon usage normally found in genes that are highly expressed in the host organism, e.g. *Escherichia coli* or *Pichia pastoris*. By selecting codons rich in G+C content, synthetic DNA molecules may also be designed to lower the A+T-rich base composition found in the Clostridial genes. According to the invention, a host cell is a cell of any organism other than *Clostridium*. Nonlimiting examples of host cells include gram negative bacteria, yeast, mammalian cells, and plant cells.

In some embodiments of the invention, upon expression of the DNA, a BoNT LC is produced in a heterologous host system by itself or as a fusion with another protein or a carrier. Proteins with which BoNT LCs may be fused include BoNT HCs, maltose-bonding proteins, other neurotoxins, neuropeptides, and autofluorescent proteins. A synthetic light chain gene may be genetically fused to a gene encoding a BoNT HC, producing recombinant *botulinum* toxin.

In some embodiments of the invention, BoNT LC is produced that is (i) substantially free of contaminating toxicity, (ii) moderately to highly soluble in aqueous media, (iii) stable for at least about six months at 4° C., (iv) catalytically active, (v) functionally active, or combinations thereof. In some embodiments of the invention, gram quantities of BoNT LC may be obtained per liter of culture medium. In some embodiments of the invention, a recombinant BoNT LC may reduce any immunological response that may result from the presence of binding proteins associated with the recombinant BoNT LC.

In some embodiments, the invention provides BoNT LC that substantially lacks catalytic activity as a zinc protease as measured by the SNAP-25 assay described in Examples 8, 17, and, 25 below. In some embodiments, the invention provides nucleic acids that encode recombinant BoNT LC substantially lacking catalytic activity as a zinc protease, wherein amino acids in or spatially near the active site are deleted, replaced or modified relative to wild-type native BoNT. Catalytically inactive BoNT LC may be fused with BoNT HC to form a mutant recombinant holotoxin. Such holotoxins may be used to carry molecules, e.g., drugs, into cholinergic nerve cells.

In some embodiments, this invention provides a nucleic acid comprising a nucleic acid sequence encoding the N-terminal portion of a full length *botulinum* neurotoxin (BoNT) selected from the group consisting of BoNT serotype A, BoNT serotype B, BoNT serotype C1, BoNT serotype D, BoNT serotype E, BoNT serotype F, and BoNT serotype G, wherein said nucleic acid is expressible in a recombinant organism selected from *Escherichia coli* and *Pichia pastoris*. In some preferred embodiments, the nucleic acid corresponds in length and encoded amino acid sequence to the BoNT light chain (LC). In some particularly preferred embodiments, the nucleic acid comprises a nucleic acid sequence selected from SEQ ID NO:4 (serotype A), SEQ ID NO:6 (serotype B), SEQ Id NO:8 (serotype C1), SEQ ID NO:10 (serotype D), SEQ ID NO:12 (serotype E), SEQ ID NO:14 (serotype F), SEQ ID NO:16 (serotype G), SEQ ID NO:22 (serotype B), SEQ Id NO:26 (serotype C1), SEQ ID NO:30 (serotype D), SEQ ID NO:34 (serotype E), SEQ ID NO:38 (serotype F), and SEQ ID NO:42 (serotype G).

In preferred embodiments, nucleic acids of the invention are synthetic nucleic acids. In some preferred embodiments, the sequence of the nucleic acid is designed by selecting at least a portion of the codons encoding BoNT LC from codons preferred for expression in a host organism, which may be selected from gram negative bacteria, yeast, and mammalian cell lines; preferably, the host organism is *Escherichia coli* or *Pichia pastoris*. The nucleic acid sequence encoding LC may be designed by replacing *Clostridium* codons with host organism codons that encode the same amino acid, but have a higher G+C content. Conservative amino acid substitutions are within the contemplation and scope of the invention. In preferred embodiments of the invention, a nucleic acid encoding a recombinant BoNT or fragment thereof is capable of being expressed in a recombinant host organism with higher yield than a second nucleic acid encoding substantially the same amino acid sequence, said second nucleic acid fragment having the wild-type *Clostridium botulinum* nucleic acid sequence.

Codon usage tables for microorganisms have been published. See e.g. Andersson S G E, Kurland C G, 1990, "Codon preferences in free-living microorganisms" Microbiol. Rev 54:198–210; Sreekrishna, 1993, "Optimizing protein expression and secretion in *Pichia pastoris*" in Industrial Microorganisms: Basic and Applied Molecular Genetics, Baltz, Hegeman, Skatrud, eds, Washington D.C., p. 123; Makofl A J, Oxer M D, Romanos M A, Fairweather N F, Ballantine S, 1989, "Expression of tetanus toxin fragment C in *E. coli*: high level expression by removing rare codons" Nuc. Acids Res. 17(24): 10191–10202. Table 3 of Skreekrishna is a chart depicting codon usage in *Pichia pastoris*. This table was generated by listing the codons found in a number of highly expressed genes in *P. pastoris*. The codon data was obtained by sequencing the genes and then listing which codons were found in the genes.

From such tables, it is clear that amino acid residues can be encoded by multiple codons. When constructing synthetic DNA molecules using *P. pastoris* codon usage, it is preferred to use only those codons that are found in naturally occurring genes of *P. pastoris*, and it should be attempted to keep them in the same ratio found in the genes of the natural organism. When the clostridial gene has an overall A+T richness of greater than 70% and A+T regions that have spikes of A+T of 95% or higher, they have to be lowered for expression in expression systems like yeast. Preferably, the overall A+T richness is lowered below 60% and the A+T content in spikes is also lowered to 60% or below. In preferred embodiments of the invention, maintaining the same codon ratio (e.g., for glycine GGG was not found, GGA was found 22% of the time, GGT was found 74% of the time, GGC was found 3% of the time) is balanced with reducing the high A+T content. In the construction of the DNA molecules of the invention, it is preferred to avoid spikes where the A+T content exceeds about 55%.

According to the invention, a spike may be a set of about 20 to about 100 consecutive nucleotides. A spike having an high A+T content greater than 80% or 90% may function as transcription termination sites in host systems, thereby interfering with expression. Preferred synthetic DNA molecules of the invention are substantially free of spikes of 50 consecutive nucleotides having an A+T content higher than about 75%. Alternatively, preferred synthetic DNA molecules of the invention are substantially free of spikes of 75 consecutive nucleotides having an A+T content higher than about 70%. Alternatively, preferred synthetic DNA molecules of the invention are substantially free of spikes of 100 consecutive nucleotides having an A+T content higher than about 60%.

A synthetic DNA molecule of the invention designed by using *E. coli* codons is expressed fairly well in *P. pastoris*. Similarly, a synthetic gene using *P. pastoris* codons also appears to be expressed well in *E. coli*.

In some embodiments, this invention provides an expression vector comprising a nucleic acid of this invention, whereby LC is produced upon transfection of a host organism with the expression vector. Another embodiment of this invention provides a method of preparing a polypeptide comprising the BoNT LC selected from the group consisting of BoNT serotype A, BoNT serotype B, BoNT serotype C, BoNT serotype D, BoNT serotype E, BoNT serotype F, and BoNT serotype G, said method comprising culturing a recombinant host organism transfected with an expression vector of this invention under conditions wherein BoNT LC is expressed. Preferably, the recombinant host organism is a eukaryote. In another preferred embodiment, the method of this invention further comprises recovering insoluble protein from the host organism, whereby a fraction enriched in BoNT LC is obtained. *E. coli* is a preferred host for expressing catalytically-active (i.e., proteolytically-active) LC. *Pichia pastoris* is a preferred host organism for expressing inactive or mutated LC. *Pichia pastoris* has SNARE proteins which probably get inactivated by catalytically-active LC.

In some embodiments, the invention provides an immunogenic composition comprising a suitable carrier and a BoNT LC selected from the group consisting of BoNT serotype A, BoNT serotype B, BoNT serotype C, BoNT serotype D, BoNT serotype E, BoNT serotype F, and BoNT serotype G. Preferably, the immunogenic composition is prepared by culturing a recombinant organism transfected with an expression vector encoding BoNT LC. More preferably, the immunogenic composition is prepared by a method wherein an insoluble protein fraction enriched in BoNT LC is recovered from said recombinant organism. More preferably, the immunogenic composition is prepared by the method of Example 30.

According to some non-limiting embodiments, the invention provides reagents and compositions that are useful for developing therapeutic interventions against BoNT. For example, the recombinant BoNT nucleic acids and polypeptides of the invention may be used to screen for *botulinum* neurotoxin inhibitors.

In some embodiments, the invention provides therapeutic agents for clinical disorders such as dystonias, spasticity, and pain. According to these embodiments, the agents may be prepared by first expressing and purifying BoNT LC independently of any portion of the heavy chain. The BoNT LC so produced is then fused to the heavy chain or fragments thereof, e.g., HN and HC. Alternatively, BoNT LC may be coexpressed and/or copurified with BoNT HC or fragments thereof and then fused to BoNT HC or fragments thereof. These agents may be used in clinical (human) or veterinary (non-human animal) applications.

In some embodiments, the invention provides agents that may be useful for treating disorders associated with cholinergic nerve function, SNAP-25, VAMP, syntaxin or combinations thereof. In some embodiments, the invention provides agents that may be useful for reducing any immunological response that may result from the presence of binding proteins associated with the agents. For example, the native BoNT holotoxin is highly immunogenic and some patients become refractory to continued treatment with it over time as their protective antitoxin titer rises. The efficacy of holotoxin-based drugs (e.g., BOTOX, Myobloc/Neurobloc, Dysport) may be improved by pretreating patients having a high titer of anti-holotoxin antibodies with a holotoxin fragment such as Lc, Hn, or Hc. These fragments may bind the anti-holotoxin antibodies making them unavailable for binding the subsequently administered holotoxin. This may work for a short time (months to a few years) realizing eventually that the antibody level may be built up so much that the drug can no longer be effective even with the addition of fragments. At this point in time, the patients will have to use a different serotype toxin drug or a chimera of the toxin (i.e., mixing toxin domains).

In further embodiments, the invention provides an immunogenic composition comprising a suitable carrier and a BoNT LC selected from the group consisting of BoNT serotype A, BoNT serotype B, BoNT serotype C, BoNT serotype D, BoNT serotype E, BoNT serotype F, and BoNT serotype G. Preferably, the immunogenic composition is prepared by culturing a recombinant organism transfected with an expression vector encoding BoNT LC. More preferably, the immunogenic composition is prepared by a method wherein an insoluble protein fraction enriched in BoNT LC is recovered from said recombinant organism.

The LC is present in immunogenic compositions of the invention in an amount sufficient to induce an immunogenic response thereto.

Two of the major advantages of the recombinant *botulinum* neurotoxins and fragments of the invention are the safety and high yields possible. First, the recombinantly-produced *botulinum* neurotoxin (rBoNT) protein fragments are completely nontoxic and are, thus, very safe. The fermentation of the host cell harboring the rBoNT gene (e.g., *Escherichia coli* or *Pichia pastoris*) does not require the high biological containment facilities presently needed to ferment the spore-forming *Clostridium botulinum* required for the production of the neurotoxin light chains. Second, synthetic DNA molecules of the invention can be placed in high expression systems and used to make much larger quantities of the BoNT fragments than toxin produced by the parent organism, *Clostridium botulinum*. Thus, there may be immense cost savings because it will be easier and safer to produce much larger quantities of the proteins for various uses including vaccination.

Synthetic DNA molecules as described herein may be transfected into suitable host organisms to create recombinant production organisms. Cultures of these recombinant organisms can then be used to produce recombinant BoNT fragments or holotoxins. Exemplary techniques for transfection and production of BoNT fragments are shown in the Examples. Alternative techniques are well documented in the literature See, e.g., Maniatis, Fritsch & Sambrook, "Molecular Cloning: A Laboratory Manual" (1982); Ausubel, "Current Protocols in Molecular Biology" (1991); "DNA Cloning: A Practical Approach," Volumes I and II (D. N. Glover, ed., 1985); "Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, ed., 1986); "Immobilized Cells and Enzymes" (IRL Press, 1986); B. Perbal, "A Practical Guide to Molecular Cloning" (1984), and Sambrook, et al., "Molecular Cloning: a Laboratory Manual" (1989). Such techniques are explained fully in the literature. Modification of these techniques within the scope of this invention is within the skill in the art.

Recombinant forms of *botulinum* neurotoxin light chain may be useful in one or more of the following applications: strabismus and other disorders of ocular motility, dystonia, blepharospasm, cervical dystonia, oromandibular dystonia, laryngeal dystonia (spasmodic dysphonia), limb dystonia, hemifacial spasm and other facial dyskinesias, tremors of the head and hands, eyelid, cervical, and other tics, spasticity (e.g. anal), Stiff-Person syndrome, bladder dysfunction (e.g. in patients with spinal-cord injury), segmental myoclonus and other hyperkinetic disorders, cosmetic treatment of glabelar frown lines and other facial wrinkles, and all conditions characterized by hyperactivity of the lower motor neuron. See Cardoso and Jankovic, 1995 "Clinical use of *botulinum* neurotoxins" Curr Top Microbiol Immunol. 195: 123–41 and references cited therein. The light chain may further be used to control autonomic nerve function (U.S. Pat. No. 5,766,605) or tiptoe-walking due to stiff muscles common in children with cerebral palsy, according to findings published in the November 2001 issue of *Pediatrics*.

Absolute contraindications to the use of BONT are allergy to the drug and infection or inflammation at the proposed injection site whereas myasthenia gravis, Eaton-Lambert syndrome, motor neuron disease, and coagulopathy are relative contraindications (National Institutes Of Health Consensus Development Conference Statement On Clinical Use Of *Botulinum* Toxin 1991; Report Of The Therapeutics And Technology Assessment Subcommittee Of The American Academy Of Neurology 1990). Safety for use during pregnancy and lactation has not been firmly established (National Institutes Of Health Consensus Development Conference Statement On Clinical Use Of *Botulinum* Toxin 1991).

The invention contemplates isoforms of the light chain as well as chimeras with other domains of the toxin or other proteins. In other words, gene fragments with DNA sequences and amino acid sequences not identical to those disclosed herein may be discovered in nature or created in a laboratory. The invention contemplates the production of any protein or polypeptide that has biological activity/functionality similar to the wild-type *botulinum* neurotoxin light chain, e.g. cell binding, translocation across membrane, catalytic activity sufficient to inactivate critical proteins in a cell involved with protein trafficking, release of various chemical transmitters (i.e., acetylcholine, glutamate, etc.), hormones, etc.

For example, the light chain and translocation domain may be combined with a protein or peptide that targets a different receptor and/or cell-type. In addition, the invention contemplates therapeutic delivery of synthetic DNA molecules of the invention to cells via viral vectors such as adenovirus or other gene therapy techniques.

EXAMPLES

In order to facilitate a more complete understanding of the invention, a number of nonlimiting Examples are provided below for illustration purposes only. To advance these purposes, the Examples are arranged in four sets: Examples 1–13, Examples 14–20, Examples 21–29, and Example 30.

Example 1

Chemicals, Buffers, and Reagents

Buffer T (20 mM Tris-HCl, pH 9.2) and buffer G (50 mM sodium glycine, pH 9.0) were used as indicated. SKL (sodium N-lauryl sarcosine or sarkosyl) was from Sigma. Highly purified (>95%) full-length BoNT/A was purchased from List Biologicals (Campbell, Calif.). Rabbit polyclonal antibodies against a 16-residue N-terminal sequence (PFVNKQFNYKDPVNGV; SEQ ID NO:1) of the BoNT/A LC were produced and affinity purified by Research Genetics (Huntsville, Ala.). Peroxidase-coupled goat anti-rabbit and anti-mouse IgG (H+L) and ABTS substrate were from Kirkegaard Perry Laboratories (Gaithersburg, Md.). Oligonucleotides, designed for *E. coli* codon usage (Anderson and Kurland, 1990) and ranging in size from 70 to 100 nucleotides, were synthesized by Macromolecular Resources (Fort Collins, Colo.).

Example 2

Construction and Expression of a Synthetic DNA Encoding rBoNT/A LC

The DNA encoding the enzymatic LC domain of BoNT/A was assembled from three segments, a 335-base pair (bp) Sal I-Sph I fragment, a 600-bp Sph I-Kpn I fragment, and a 460-bp Kpn I EcoR I fragment. To construct the first segment, six oligonucleotide pairs were annealed, ligated, and, after PCR amplification, inserted into pGEM3Zf at Sal I-Sph I restriction enzyme sites. The second segment was built by annealing and ligating eight oligonucleotide pairs, followed by its amplification and insertion into the Sph I and Kpn I sites of pGEM3Zf. The final segment was constructed by annealing and ligating six oligonucleotide pairs, followed by its amplification and insertion into the Kpn I-EcoR I sites of pGEM3Zf. Nucleotide sequencing of gene fragments in pGEM3Zf was performed to identify clones in each group with minimal misincorporations. In vitro mutagenesis was performed to correct the misincorporations in the BoNT/A LC minigene fragments. Directional gene assembly via 600-bp and 460-bp fragments in pGEM3Zf was followed by the insertion of the 335-bp fragment.

In the design of the synthetic DNA, the 5' oligonucleotide for amplifying the gene's 5' terminus consisted of an anchored Sal I site followed by an EcoR I site and an Nco I site to facilitate directional subcloning into the *E. coli* expression vector, pET24d. The 3' oligonucleotide contained a hexahistidine tag with a thrombin protease cleavage site for creating a carboxyl-terminal removable histidine tag. The 3' end also included the restriction enzyme sites for BamH I and EcoR I.

The full-length gene was excised from pGEM3Zf 5 with an Nco I-EcoR I and subcloned into a similarly digested pET24d vector. The resulting ligated construct was used to transform *E. coli* BL21(DE3) cells. Two clones were assayed for their ability to express rBoNTA LC. Single colonies were inoculated into 5 ml of Luria broth (LB) containing 50 µg/ml of kanamycin and grown overnight at 37° C. The overnight cultures (500 µL) were used to inoculate 50 ml of LB containing 50 µg/ml of kanamycin. When the cultures reached $OD_{600}$ of 0.8, induction was initiated by addition of isopropyl-β-D-thiogalactoside (IPTG) (final concentration, 1.0 mM). The cultures were induced for 2 hr at 37° C., harvested, and analyzed for expressed products on SDS-PAGE.

Results

A synthetic DNA encoding rBoNTA LC was designed with *E. coli* codon usage, constructed, and expressed in *E. coli*. The native nucleic acid sequence from *C. botulinum* type A NTCC 2916 (Thompson et al., 1990) was used as the template for preparing synthetic LC sequences of the invention.

At the 5' end of the DNA, an Nco I restriction enzyme site was employed as a cloning site and palindrome to provide an initiation codon. The use of this Nco I site necessitated the use of a filler codon (GTT) between the Met initiation codon (ATG) and the codon (CAG) specifying the first amino acid residue in the LC (i.e., Q). This resulted in the introduction of one extra amino acid, Val, as the N-terminal residue (after the initiating Met). This extra and new amino acid, however, did not interfere with expression or activity. The length of the LC (448 residues) to be expressed was chosen from the sequence of amino acids around the nicking site (DasGupta and Dekleva, 1990) (FIG. 1). At the C-terminal end (i.e., DKGYNK; residues 444–449 of SEQ ID NO:5), a hexa-His tag was incorporated for affinity purification and a thrombin cleavage site (LVPRGS; residues 450–455 of SEQ ID NO:5) was incorporated for removing the hexa-His tag. The expressed protein therefore contained a total of 461 (1+448+ 6+6) residues (FIG. 1 and SEQ ID NO:5). The synthetic gene thus constructed in pET24d vector was highly and efficiently expressed in *E. coli*, accounting for about 25% of the total protein (FIG. 2).

Example 3

Fermentation

A frozen stock seed culture of recombinant *E. coli* harboring the synthetic DNA encoding the LC of BoNT/A was grown at 37° C. to an $OD_{600}$ of 2.682 in a shake flask containing 100 ml of the following defined medium: casamino acids (1.4 g/L); yeast extract (2 g/L); $(NH_4)_2SO_4$ (1.85 g/L); $K_2HPO_4$ (30 g/L); $MgSO_4.7H_2O$ (2 g/L); thiamine.HCl (0.015 g/L); glucose (18.1 g/L); trace elements solution (3 ml/L) consisting of $FeCl_3.6H_2O$, 27 g; $ZnCl_2.4H_2O$, 1.3 g, $CoC_2.H_2O$, 2 g; $Na_2Mo_4.2H_2O$, 2 g; $CaCl_2.2H_2O$, 1 g; $CuCl_2.2H_2O$, 1 g; $H_3BO_3$, 0.5 g; distilled $H_2O$, 1000 ml; and HCl, 100 ml. In addition, 0.0156 g/L of ZnCl was added to trace minerals to make the concentration of Zn five times greater in the shake flask and fermentor. Kanamycin (50 µg/L) was added as an antibiotic. The shake flask culture was used to inoculate a 5-L BioFlo III fermentor (New Brunswick Scientific, Edison, N.J.) containing 4.3 L of the medium described above. Later in the growth (5.5 hr), 14.1 g/L of casamino acids was added and a glucose feed was initiated to maintain a glucose concentration of 1 g/L. Growth continued for 8 hr until an $OD_{600}$ of 49.9 was reached. Cell induction was then initiated at this time by adding IPTG (final concentration, 1.5 mM). Induction continued for 4 hr after adding IPTG, and cells ($OD_{600}$ of 112.62) were harvested by centrifugation (Beckman, Palo Alto, Calif.) at 7000 rpm for 15 min at 4° C. Cells were washed with cold 0.9% saline and centrifuged at 7000 rpm for 15 min and frozen at −70° C. Wet cell yield was 58 g/L.

Example 4

Extraction and Purification of Light Chain as Inclusion Bodies

In a typical preparation, 12 g of *E. coli* cells was suspended in a total volume of 30 ml of buffer T containing 5 mM $MgCl_2$, 1.5 mM PMSF, 10 mM β-mercaptoethanol, and 2 mg of DNAse. The cell suspension was subjected to 10 cycles of 2-min sonication (at 60% power in a Fisher Model 300 Sonic Dismembrator) and 2-min cooling on ice. After centrifugation for 15 min at 10,000 ×g, the supernatant was discarded. The pellet was suspended in 30 ml the above buffer. The cycle of sonication and centrifugation was repeated five more times; $MgCl_2$ and DNAse were omitted from the buffer during the last two cycles. The resulting pellet contained the rBoNT/A LC, that appeared ~70% pure by SDS PAGE (FIG. 2). The pellet was stored at 4° C. as a white suspension in 15 ml of buffer T containing 1.5 mM PMSF and 10 mM β-mercaptoethanol.

Results

The expressed LC appeared exclusively in the insoluble pellet fraction (FIG. 2). Including $MgCl_2$ and DNase in the cell suspension ensured a clean separation of the pellet from the supernatant after sonication and centrifugation. The white suspension of the purified BoNT/A LC migrated as a 52-kDa band and appeared to be ~70% pure on SDS-PAGE (FIG. 2A), as determined by densitometric analysis. Minor contaminant bands with ~100-kDa, 37–40 kDa, and ~25 kDa also reacted with the antibody in the Western blot (FIG. 2B). While fragments smaller than 50 kDa may have arisen from proteolysis of the LC (DasGupta and Foley, 1989), the origin of the 100-kDa species in the reducing SDS-PAGE gels is not clear since the species also reacts with the affinity-purified antibodies against a small sequence of the LC. Molecular mass determination by MALDI-MS gave 52.774 (±50) kDa as the predominant species along with minor species of 106.028 (±100) kDa and 25.00 (±25) kDa. Amino acid sequence determination of the LC identified V-Q-F-V-N-K-Q (residues 2 to 8 of SEQ ID NO:5) as the amino-terminal sequence, as expected for the constructed gene (FIG. 1) and identical (with the exception of the penultimate valine) to that of the published sequence of BoNT/A (Thompson et alt., 1990).

Example 5

Solubilization of the Inclusion Bodies to Obtain Active rBoNT/A LC

In a typical experiment, 0.75 ml of the white rBoNT/A LC suspension (from an equivalent of 600 mg of wet cells) was centrifuged in a 2-ml Eppendorf tube and the supernatant was discarded. The pellet was suspended by mild sonication in 0.9 ml of 50 mM Tris-HCl, pH 9. A 20% solution (0.9 ml) of SKL in water was added to the suspension at room temperature and was mixed by inversion several times. Within 2 min, the pellet became completely soluble. Any remaining turbidity was cleared by further diluting with 50 mM Tris-HCl, pH 9.0, or was removed by centrifugation. The SKL-solubilized LC was dialyzed against 200 volumes of buffer G containing 1 mM DTT with one to two daily changes at 4° C. for 1 week. The yield of the soluble rBoNT/A LC was 12 mg (3.9 mg/ml), which was stored in a glass tube at 4° C.

Results

The purified inclusion bodies were solubilized in 10% SKL and the SKL was removed by dialysis against buffer G containing 1 mM DTT (see Section 2). The use of a 10% SKL solution ensured solubilization within 2 min of incubation, and the LC solution was immediately subjected to extensive dialysis to remove the detergent. Starting with an equivalent of 600 mg of the wet E. coli cells, 12 mg of the soluble LC was obtained, corresponding to 20 mg LC per gram of wet cells. This corresponds to a yield of 1.16 g of the pure protein per liter of cell culture.

Example 6

Properties of the Purified BoNT/A LC

Figures 3, 4:
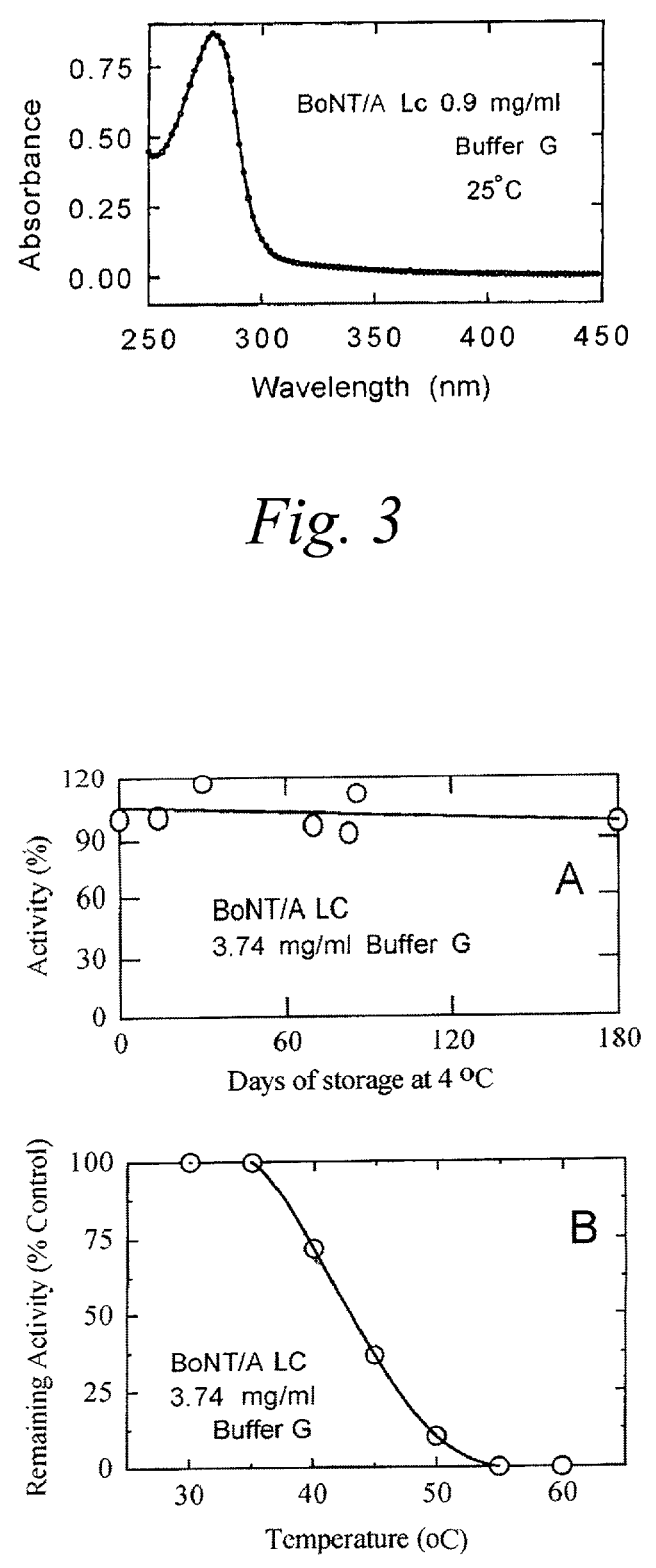

The UV-visible absorption spectrum (FIG. 3) shows the rBoNT/A LC with a single maximum at 278 nm as a simple protein. Although a number of minor band were observed in the SDS-PAGE gel (FIG. 2), absence of any other absorbance bands in the UV-visible range suggests the absence of any nonmetal cofactor in the preparation. The LC was expressed as a C-terminally His-tagged protein. In the presence of 6 M GuHCl, the rBoNT/A LC was bound to Ni-resin and was eluted with immiadzole-containing buffers as a more purified form. Without GuHCl, the rBoNT/A LC did not bind to Ni-resin. This result suggests that the LC retained the His-tag after expression and purification, but in the absence of GuHCl, the His-tag was not exposed to solvent to chelate with the Ni-resin. Because the rBoNT/A LC had catalytic properties comparable to those of the dicchain (see below), removal of the His-tag from the purified protein was not attempted.

The purified LC was stable for at least 6 months when stored at 4° C. in buffer G containing l mM DTT (FIG. 4A). During this period, the protein remained fully soluble, did not show any degradation as analyzed SDS-PAGE, and retained its initial catalytic activity. An LC preparation obtained by prolonged solubilization in 0.5% SKL at room temperature, however, precipitated after 3 months of storage at 4° C. and lost most of its initial catalytic activity. The LC (1 mg/ml of 50 mM Na-phosphate) precipitated from solution below pH 8 either at 4° C. or at 25° C. Thermal stability of the LC (3.74 mg/ml of buffer G containing 1 mM DTT and 50 µM ZnCl$_2$) was investigated by incubating aliquots for 45 min at various temperatures. After cooling on ice for 45 min, the catalytic activities in the supernatants were measured. The midpoint of thermal unfolding $T_m$ as measured by activity was 43° C. (FIG. 4B). At room temperature, increasing concentration of MgCl$_2$ also precipitated the LC from solution: at 6 mM MgCl$_2$, >80% of the LC precipitated.

Example 7

Preparation of Apo-rBoNT/A LC

One milliliter of rBoNT/A LC (2.73 mg) was dialyzed overnight against 250 ml of buffer G containing 5 mM EDTA and 1 mM DTT. EDTA was removed by further dialysis for 60 hr against three changes of 250 ml of buffer G containing 1 mM DTT.

Example 8

Assay of Proteolytic Activity of BoNT/A LC

BoNT/A cleaves the glutamyl-arginine bond between residues 197 and 198 of the 206-residue SNAP-25. Schmidt and Bostian (1995) showed that a synthetic 17-residue peptide representing residues 187–203 of SNAP-25 was sufficient for detecting endopeptidase activity of BONT/A and allowing routine assay for the neurotoxin activity. The peptide thus probably mimics the structure of SNAP-25 in vivo (Bi et al., 1995). The same peptide was used in an identical method to assay the proteolytic activity of the BONT/A LC.

The assay is based on HPLC separation and measurement of the nicked products from a 17-residue C-terminal peptide of SNAP-25 (FIG. 5), corresponding to residues 187–203, which is the minimum length required for BoNT/A proteolytic activity (Schmidt and Bostian, 1995, 1997). Unless otherwise noted, a 0.03-ml assay mixture containing 0.8–1.0 mM substrate, 0.25 mM ZnCl$_2$, 5.0 mM DTT, 50 mM Na-HEPES buffer (pH 7.4), and BONT/A LC was incubated at 37° C. for 15–80 min. The amounts of uncleaved substrate and the products were measured after separation by reverse-phase HPLC (Waters) on a Hi-Pore C 18 column, 0.45×25 cm (Bio-Rad Laboratories, Hercules, Calif.) with the Millennium software (Waters) package. Solvent A was 0.1% TFA and solvent B was 70% acetonitrile/0. 1% TFA. The flow rate was 1.0 ml/min at 25° C. After the column was equilibrated with 10% B, the sample was injected, and the column was held at 10% B for 2.5 min. A linear gradient to 36% B over 21 min was followed by 100% B for 6 min. Kinetic parameters for the synthetic substrate were calculated from Lineweaver-Burk plots of activity with peptide concentrations from 0.26 to 1.7 mM.

Catalytic Activity of the LC

Figure 5:
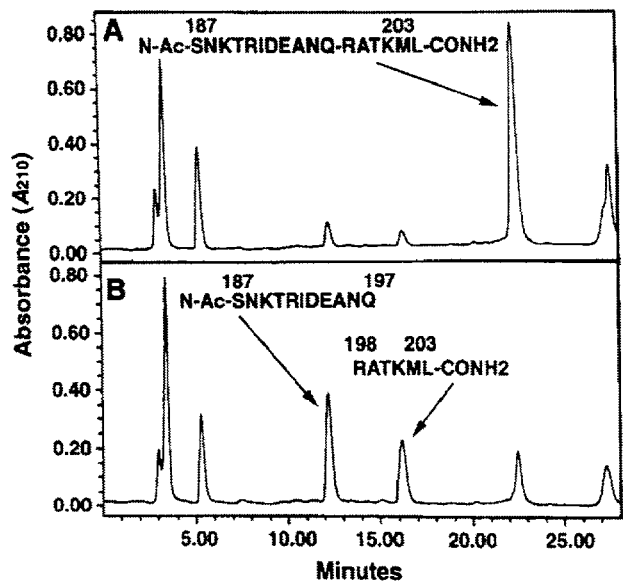
FIG. 5. Proteolysis of the synthetic peptide substrate by the rBoNT/A LC. The peptide (1.1 mM) was incubated for 5 min (A) or 200 min (B) with the rBoNT/A LC. The reaction products were analyzed by reverse-phase HPLC. The first three peaks represent the solvent front (<4 min) and reduced DTT (5.2 min) in the reaction mixture. Sequence of the substrate (SEQ ID NO:2) and the sequences of the products (residues 1 to 11 and residues 12 to 17 of SEQ ID NO:2) are shown in panels A and B, respectively. The numbers above the sequences represent the LC residue numbers corresponding to the sequence of SNAP-25. The product peaks (not labeled in Panel A) were identified by sequence determination by MS-MS.

The BoNT/A LC is zinc-endopeptidase specific for the cleaving the peptide bond between residues 197 (Glu) to and 198 (Arg) of SNAP-25. Incubating the 17-mer synthetic peptide representing residues 187–203 of SNAP-25 with the LC at 37° C. for 5–200 min generated only two peptides (FIG. 5). That no other peptide fragments were generated by this prolonged incubation proves that the contaminants present in the LC preparation were devoid of any proteolytic activity. Incubating the LC with BSA also failed to produce any proteolytic fragment. In contrast to the BoNT/A dichain, whose activity ruin is greatly enhanced by BSA (Schmidt and Bostian, 1997), the rate of cleavage of the synthetic peptide substrate was unaffected by the presence of BSA.

Proteolytic activity of the purified rBoNT/A LC linearly increased with the increasing amount of the LC in the reaction mixture. The time course of activity (at 0.8–1.0 mM substrate concentration), however, was not linear, but progressively declined, possibly due to a high $K_m$ for the substrate peptide (see below). Therefore, routine assays depended on initial activities representing <30% substrate conversion.

Substrate $K_m$ for the LC was fourfold lower than that reported for the dichain (Schmidt and Bostian, 1995). This may be due to shielding of the active site by a 'belt' from the translocation domain ($H_n$) in the dichain neurotoxin (Lacy et al., 1998; Lacy and Stevens, 1999). Thus, the 'belt' may pose a steric hindrance for substrate binding by the dichain (high $K_m$).

Nonetheless, the catalytic efficiency $k_{cat}/K_m$ of the free rBoNT/A LC was somewhat higher than that of the dichain.

Optimum pH, Salts, and Buffers

Figure 6:
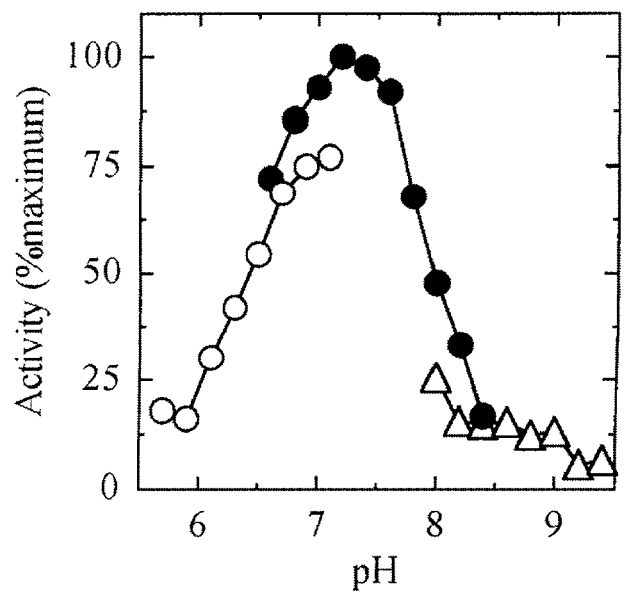
FIG. 6. Effect of pH on the endopeptidase activity of the rBoNT/A LC. Activities were measured at various pH of 0.1 M buffers: MES (-○-), HEPES (-●-), and tris-HCl (-Δ-) containing 0.9 mM substrate peptide Maximum activity (100%) was 334 nmol/min/mg LC.

An optimum pH of 7.2 for the proteolysis of the synthetic substrate by the rBoNT/A LC was determined by assaying in three different buffer systems (0.1 M) ranging in pH from 5.0 to 9.0 (FIG. 6). For comparison, the optimum pH values of BoNT/B and tetanus neurotoxin, two members of the clostridial neurotoxin family, are 6.5–7.0, and 6.5–7.5, respectively (Foran et al., 1994). Tris-HCl appeared to have an inhibitory effect on proteolysis, presumably due to chelation with the zinc at the active site. The activity at pH 7.4 was 25% higher in a 50 mM HEPES buffer than in 100 mM HEPES. Adding 50 mM NaCl, KCl, or NaPO$_4$ (pH 7.4) to the standard reaction mixture reduced activity 40–50%. Thus, high salt concentrations inhibited the proteolytic reaction.

Effect of Metals and Thiol Reagents on Activity

Figure 7:
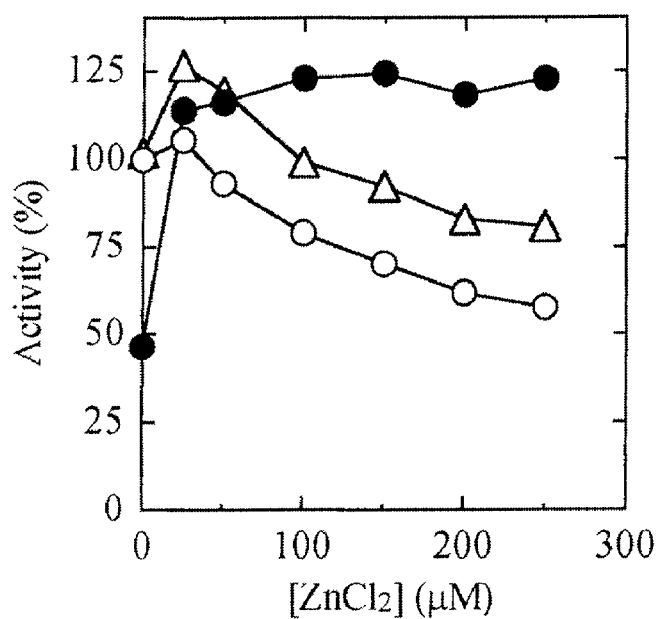
FIG. 7. Inhibition of endopeptidase activity of the rBoNT/A LC by excess $Zn^{2+}$ and protection from inhibition by DTT. The LC was assayed in SO mM HEPES, pH 7.4, containing 0.9 mM substrate peptide in the absence (-○-) and presence of 5 mM DTT (-●-) or 5 mM mercaptoethanol (-Δ-) containing the indicated concentrations of $ZnCl_2$. One hundred percent activity (290 nmol/min/mg LC) represents the activity obtained in the absence of any added thiol or $Zn^{2+}$.

BoNT/A LC is a zinc-endopeptidase. Activity of the rBoNT/A LC was completely inhibited by including the metal chelator EDTA (1 mM) in the reaction mixture (Table 1). Adding low concentrations of ZnCl$_2$ (1–50 μM) in the assay mixture slightly stimulated the activity (5%–10%) and higher concentrations of ZnCl$_2$ inhibited the activity (FIG. 7). The results suggest that the active site should be almost saturated with $Zn^{2+}$ for optimum activity. The metal was tightly bound to the active site of the LC, as the extraction, purification, or dialysis buffers were devoid of $Zn^{2+}$. Like $Zn^{2+}$, other divalent metal ions, notably, MnCl$_2$ and NiSO$_4$, also inhibited the LC reaction to various extents in the absence of added thiol (Table 1). Adding 5 mM DTT to the reaction mixture neutralized the inhibitory effect of $Zn^{2+}$ (FIG. 7).

Neurotoxic or proteolytic activity of the dichain BONT/A probably requires an initial reduction of the disulfide bond between the LC and the HC (de Paiva et al., 1993). Therefore, the proteolytic assay mixture of BONT/A with the synthetic or natural substrates were supplemented with 5–10 mM DTT (Washbourne et al., 1997; Schmidt and Bostian, 1995, 1997). In the absence of $Zn^{2+}$, 5 mM DTT in the reaction mixture significantly inhibited the activity of the LC (Table 1 and FIG. 7). Similarly, L-cys, dithioerythreitol, and glutathione inhibited the activity to various extents, while β-mercaptoethanol stimulated the activity in the absence of added $Zn^{2+}$. These results were unexpected as the LC does not possess any disulfide bonds and the invariant Cys responsible for the interchain disulfide is far from the active site. One explanation for these effects is the formation of a mixed disulfide between a protein thiol and the exogenous thiol. To investigate the importance of a protein Cys residue on activity, several sulfhydryl reagents were incubated in the proteolytic assay mixture (Table 1). Both HgCl$_2$ and p-Cl-mercuric benzoate completely abolished the activity of LC. Preincubating the LC with these two reagents, then diluting with the proteolytic reaction mixture, also gave the same results. These results suggest the presence of a protein thiol in the vicinity of the active site of the LC.

TABLE 1

Effect of Metal Ions and Thiols and Thiol Reagents on the Activity of the rBoNT/A LC

| Thiol reagent | Concentration (mM) | % Activity | Metal reagent | Concentration (mM) | % Activity |
|---|---|---|---|---|---|
| None[a] | | 100 | EDTA | 1 | 00 |
| Dithiothreitol | 5 | 45 | ZnCl$_2$ | 0.25 | 60 |
| Dithioerythreitol | 5 | 60 | — | 1 | 10 |
| β-Mercaptoethanol | 5 | 120 | — | 0.25 | |
| Glutathione, reduced | 5 | 75 | +Dithiothreitol | 5 | 125 |
| Glutathione, oxidixed | 5 | 75 | MnCl$_2$ | 1 | 40 |
| S-Nitrosoglutathione | 5 | 55 | MgCl$_2$ | 1 | 90 |
| L-Cysteine | 5 | 20 | CaCl$_2$ | 1 | 75 |
| p-Cl-Mercuribenzoate | 0.050 | 00 | FeCl$_3$ | 1 | 35 |
| Mercuric chloride | 0.013 | 00 | CoCl$_2$ | 1 | 90 |
| Iodoacetamide | 10 | 80 | CuSO$_4$ | 1 | 95 |
| | | | NiSO$_4$ | 1 | 55 |

[a]The reaction mixture contained only the substrate and the rBoNT/A Lc. Other conditions are as described in Examples 8–20.

Steady-State Kinetic Parameters

Figure 8:
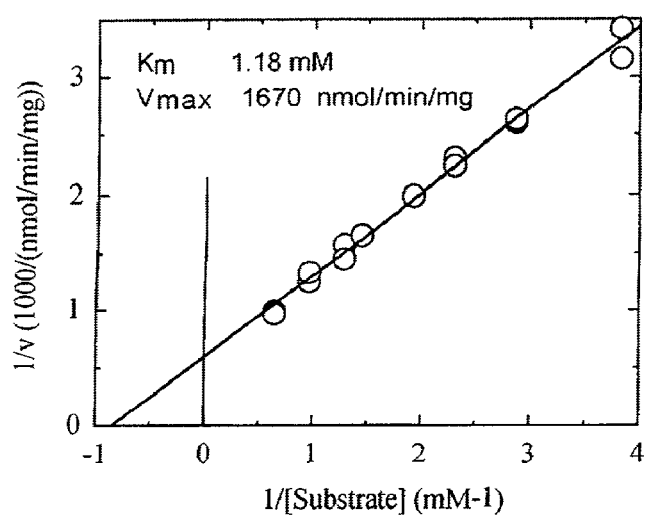
FIG. 8. Determination of $K_m$ and $V_{max}$ from the double-reciprocal (Lineweaver-Burke) plot of initial rates of proteolysis versus substrate concentration by the rBoNT/A LC. The reaction mixtures (0.03 ml) contained 0.25 mM $ZnCl_2$, 0.5 mM DTT, 50 mM HEPES, pH 7.4, and 0.016 mg rBoNT/A LC. The $K_m$ and $V_{max}$ were calculated as 0.9 mM and 1500 nmol/min/mg, respectively.
Figure 9:
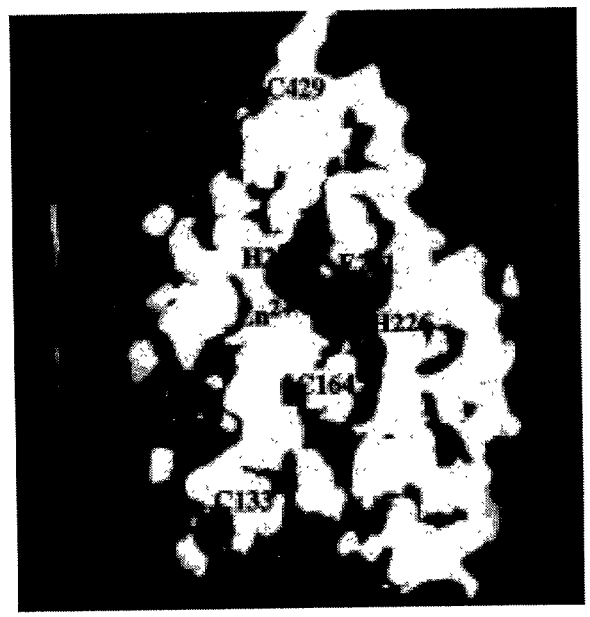
FIG. 9. Location of the three Cys residues in the BoNT/A LC. Molecular surface of the LC portion of the BoNT/A dichain based on its three-dimensional structure (Lacy and Stevens, 1999) is shown. The three Cys residues (yellow), active-site His and asp residues (red), the $Zn^{2+}$ atom (blue) at the active site, and the 'pit' leading to the active site are highlighted. The side chain of Cys-164 lines the surface and forms part of the wall of the 'pit' leading to the active site. The 'pit' acts as an access route of the substrate.

The dependence of reaction rates on the substrate concentration was determined at 0.26–1.7 mM substrate at pH 7.4. A double reciprocal plot of the reaction rates versus substrate concentrations (FIG. 8) yielded a $K_m$ of 1.18 mM and a $V_{max}$ of 1670 (equivalent to 2390 considering a 70% pure LC) nmol/min/mg LC ($k_{cat}$=1.39/sec or 1.99 if 70% pure). For comparison, the maximum rate of cleavage of the peptide substrate by the native, dichain toxin is reported to be 1900 nmol/min/mg ($k_{cat}$=4.7/sec), while the $K_m$ is 5 mM (Schmidt and Bostian, 1997). The lower $K_m$ for the LC may be due to a more exposed active site in the free LC than in the LC of the dichain, where the active site is shielded from the solvent by elements of the membrane-spanning domain $H_N$ (28–29). The catalytic efficiency $k_{cat}/K_m$ of the rBoNT/A LC, 1.18 (1.69 if 70% pure), is thus higher than that of the dichain, 0.94 (Schmidt and Bostian, 1995, 1997).

Apo-BoNT/A LC

The rBoNT/A LC was incubated with the metal chelator EDTA and after extensive dialysis, the activity of the apo-BoNT/A LC was measured in the standard reaction mixture. In the absence of any exogenous $Zn^{2+}$ or thiol, the preparation had 17% activity of the holo-BoNT/A LC from which the apoprotein was made (Table 2). This result suggests that the bound $Zn^{2+}$ was not completely removed by the EDTA treatment and dialysis. Nonetheless, adding 5 mM DTT and 250 µM $ZnCl_2$ to the assay mixture restored 70% of the activity of the holo-LC. Moreover, in the presence of 5 mM DTT and 250 µM $MnCl_2$, $MgCl_2$, or $CaCl_2$, 20–30% of the original activity was restored.

TABLE 2

Activities of the Apo-BoNT/A LC With and Without Addition of Divalent Metal Ions to the Reaction Mixtures

| LC form | Divalent metal | % Activity | % Activity recovered[a] |
|---|---|---|---|
| Holo-LC | $+Zn^{2+}$ | 100 | — |
| Apo-LC | +None | 15 | — |
| | $+Zn^{2+}$ | 70 | 65 |
| | $+Mn^{2+}$ | 20 | 10 |
| | $+Mg^{2+}$ | 20 | 10 |
| | $+Ca^{2+}$ | 30 | 20 |
| | $+Fe^{2+}$ | 0 | — |

[a]Represents percentage of the lost activity of Zn-free apo-rBoNT/A LC that was recovered by adding the indicated metal ions.

Example 9

Vaccination of Animals

Purified rBoNTA LC was tested for its ability to elicit protective immunity in Cr1:CD-1 (ICR) male mice (Charles River) weighing 16–22 g. Two concentrations of recombinant LC (5 and 15 micrograms) with and with-out adsorption to a 0.2% Alhydrogel (Superfos Biosector, Kvisgaard, Denmark) were administered in 0.9% saline in a total volume of 100 µl. Groups of 10 mice including a naive control (saline alone) received three doses of LC at 0, 2, and 4 weeks. Mice were bled from the retroorbital sinus 12 days postvaccination and their antibodies assayed for titers to toxin. Animals were challenged with native BoNT/A dichain toxin 15 days postvaccination.

The animal room was maintained at 21±2° C. with a relative humidity 30–70%, a 12/12-hr light/dark cycle with no twilight, and 10–15 air changes/hour. Mice were housed in solid-bottom, polycarbonate Micro-Isolator™ cages (Lab Products, Inc., Seaford, Del.) with paper chip bedding (Alpha-Dri™, Shepherd Specialty Papers, Inc., Kalamazoo, Mich.) and provided food (Harlan Teklad diet No. 7022, NIH-07) and water ad libitum. All procedures were reviewed and approved by the Institutional Animal Care and Use Committee and performed in an AAALAC International-accredited facility in accordance with recommendations in the *Guide for the Care and Use of Laboratory Animals*, 1996 (National Academy Press, National Academy of Sciences, Washington, D.C.).

Example 10

ELISA

Highly purified (>95%) BoNT/A toxin was diluted to 2 µg/ml in phosphate-buffered saline (PBS), pH 7.4 (Sigma Chemical Co., St Louis, Mo.) and was dispensed (100 µl/well) into microtiter plates (Immulon 2, Dynatech Laboratories, Chantilly, Va.). The plates were incubated overnight in a humidity box at 40° C. Five percent skim milk (Difco, Detroit, Mich.) in PBS with 001% Thimerosal® was used to block nonspecific binding and as an antibody diluent. The plates were washed with PBS plus 0.1% Tween 20 between each step. Mouse sera were initially diluted 1:100 and then diluted fourfold for a total of eight dilutions (1:100 to 1:1,600,000). Diluted sera were added in duplicate to toxin-coated wells (100 µl/well). The secondary antibody was horseradish peroxidase-conjugated, goat anti-mouse IgG diluted 1:1000. The primary and secondary antibodies were incubated 90 and 60 min, respectively at 37° C. ABTS substrate (100 µ/well) was added as the color developer. The plates were incubated at room temperature for 30 min. The absorbance was measured with a microplate reader at 405 nm. A mouse monoclonal antibody, 5BA2.3, was used as the positive control in each assay; naive mouse serum was added as a negative control in each assay. The titer was defined as the geometric mean of the ELISA titer to BoNT/A toxin.

Example 11

Biological Effects of the rBoNT/A LC

LC prepared from dichain BoNTs always had residual toxicity due to some contaminating dichain forms (Maisey et al., 1988). To demonstrate and confirm that the rBoNT/A LC was nontoxic, 5–15 µg of the LC was injected per mouse, a dose that was 15,000–45,000 times higher than an equivalent lethal dose of the BoNT/A dichain. Table 3 shows that all the mice survived three successive injections. All of their antisera had high titers against BoNT/A, but these antibodies failed to protect the animals upon subsequent challenge with relatively low doses ($10^2$ $LD_{50}$) of the toxic BoNT/A dichain. Even when the ELISA titers were boosted 20-fold by using the aluminum hydroxide adjuvant, the animals were not immune to modest levels of BoNT/A challenge (Table 3). Comparable vaccination with BoNT/A Hc protected animals from challenge with as high as $10^6$ $LD_{50}$ (Smith, 1998). These results clearly demonstrate that the rBoNT/A LC was nontoxic to the animals and confirms earlier observations that LC does not possess any neutralizing epitope(s) (Chen et al., 1997; Dertzbaugh and West, 1996).

TABLE 3

Survival of Mice After Vaccination with the rBoNT/A LC and Subsequent Challenge by BoNT/A Dichain

| Dose[a] | | Survival at given BoNT/A dichain challenge[c] | |
|---|---|---|---|
| (µg/mouse) | ELISA Titer[b] | $10^2 LD_{50}$ | $10^3 LD_{50}$ |
| 0[d] | <100 | 0/5 | 0/5 |
| 5[d] | 18,000 | 0/10 | 0/10 |
| 15[d] | 63,100 | 0/10 | 0/10 |
| 0[e] | <100 | 0/5 | 0/5 |
| 5[e] | 985 | 0/10 | 0/10 |
| 15[e] | 2800 | 0/10 | 0/10 |

Although the LC by itself is nontoxic, in digitonin-permeabilized chromaffin cells (Bittner et al., 1989) and direct microinjection into the cytosol of sea urchin eggs (Bi et al., 1995; Steinhardt et al., 1994), it blocks membrane exocytosis. To demonstrate that the rBoNT/A LC preparation retained this property of inhibiting membrane exocytosis, sea urchin eggs were microinjected with the LC. Eggs of the sea urchin, *Lytechinus pictus*, are an excellent model system for the study of exocytosis. Unfertilized eggs have a layer of vesicles, the cortical granules, docked at the plasma membrane. The SNARE complexes of docked vesicles are inaccessible to the BoNTs. Thus, plasma membrane resealing of the unfertilized sea urchin egg is unaffected by microinjection with *botulinum* toxins A, B, and C1 (Bi et al., 1995; Steinhardt et al., 1994). Fertilization triggers exocytosis of the cortical granuoles. After fertilization, the vesicles available for exocytosis are largely undocked and the docking proteins of undocked vesicles are susceptible to proteolysis by injected clostridial neurotoxins.

For fertilized eggs injected with rBoNT/A LC, about 100 min at 20° C. was required to inhibit plasma membrane resealing after mechanical wounding with a glass micropipet. Eggs that successfully resealed showed a transient dye loss for about 1–2 min after micropuncture. Eggs that failed to reseal continuously lost dye and lost control of intracellular free calcium, leading to cell death. Five of five fertilized eggs wounded between 36 and 70 min after injection with the rBoNT/A LC resealed successfully, as did five of five unfertilized injected eggs. Six of six fertilized eggs wounded between 106 and 145 min after injection failed to reseal, indicating that the recombinant light chain actively inhibited exocytosis. Thus, the rBoNT/A LC had a similar effect as BoNT/B in inhibiting membrane exocytosis and resealing of plasma membrane of sea urchin eggs (Steinhardt et al., 1994).

Example 12

Exocytosis Experiments

Plasma membrane resealing after micropuncture with a glass pipette requires calcium-regulated exocytosis (Bi et al., 1995). This exocytosis is dependent on docking proteins (the SNARE complex) that are sensitive to proteolysis by the clostridial neurotoxins (Steinhardt et al., 1994). Sea urchin (*Lytechinus pictus*) eggs were used to test the biological activity of the rBoNT/A LC. The microinjection medium contained 19 volumes of the rBoNT/A LC (3.7 mg/ml) in 45 mM potassium aspartate, 5 mM HEPES, pH 8.1, and one volume of 55 mM fura-2 in 100 mM KCl and 10 mM HEPES, pH 7.1. Injection levels were 5–10% of egg volume. The plasma membrane resealing after micropuncture with a glass pipette was monitored by recording the emission from fura-2 upon excitation at 358 nm (the calcium-insensitive wave-length).

Example 13

Other Analytical Methods

Protein concentration was determined by BCA assay (Pierce) with bovine serum albumin (BSA) as a standard. Reducing SDS-PAGE with 10% tricine-gels (Novex) was according to Laemli (1970). The gels were stained with Coomassie brilliant blue. Western blots were prepared by using a primary polyclonal antibody against a 16-residue N-terminal sequence of BONT/A LC and a peroxidase-coupled goat anti-rabbit IgG (H+L) as the secondary antibody. Absorption spectrum at 25° C. was recorded in a Hewlett-Packard 8452 diode array spectrophotometer. The N-terminal amino acid sequence of the BONT/A LC was determined by Edman degradation in an Applied Biosystems Procise Sequencer in the 0- to 20-pmol detection range. Molecular mass was determined by MALDI-MS in a PE Biosystems Voyager DE instrument. Sinapinic acid was used as the matrix and the sample was spotted on a stainless steel plate that was not washed with water or TFA. Other conditions in the experiment were accelerating voltage 25,000 V, guide wire voltage 0.3%, and laser 2500.

Example 14

Chemicals, Buffers and Reagents

Buffer P (50 mM Na-phosphate, pH 6.5) was used for Examples 14–20. TPEN and $ZnCl_2$ were from Sigma. Affinity-purified, peroxidase-coupled goat anti-rabbit and anti-mouse IgG (H+L) and ABTS substrate were from Kirkegaard Perry Laboratories (Gaithersburg, Md.). The inhibitor peptide (Ac-CRATKML-$NH_2$) (SEQ ID NO:46) (Schmidt et al., 1998) was synthesized and purified by Cell Essentials (Boston, Mass.).

Example 15

BoNT/A LC Purification

The rBONT/A LC was expressed by low-temperature IPTG induction in *E. coli* BL21 (DE3) cells as a soluble protein from a synthetic gene in a pET24a-derived multi-copy plasmid (Clontech, Inc.). Construction of the gene and expression of the protein as described (Ahmed and Smith, 2000) was modified as follows: a stop codon replaced the histidine tag at the carboxy terminus of the gene, and induction and expression was at 18° C. for 22–24 hr. The LC was purified to near homogeneity by NaCl gradient elution from each of two successive cation exchange columns (MonoS) in buffer P. A typical preparation had a specific activity of 2–3 µmol/min/mg in cleaving the 17-residue substrate peptide when assayed in the presence of 0.25 mM $ZnCl_2$; in the absence of added zinc, activity was 50%. The purified LC was thus partially resolved of the bound zinc. The purified protein (1–4 ml) in buffer P was stored at −20° C. Under this condition, the protein remains stable and retains its catalytic activity for at least 1 year.

Example 16

SDS-PAGE, Transfer on PVDF Membrane, and Western Blot

SDS-PAGE under reducing conditions (Laemmli, 1970) was carried out on a 1-mm-thick 10% tricine gels (Novex) as described (Schagger and von Jagow, 1987). Samples were prepared in 0.4% SDS, 5% β-mercaptoethanol, 12% glycerol, and 450 mM Tris-HCl, ph 8.45, by boiling for 5 min. The running buffer contained 0.1% SDS in 0.1 M Tris-0.1 M Tricine, ph 8.3. The gels were stained with Coomassie Brilliant Blue. Electrophoretic transfer of peptides from SDS-PAGE gels onto PVDF membrane used 10 mM CAPS-NaOH buffer, Ph 11.0, containing 10% methanol as the transfer buffer. Protein bands on the PVDF membranes were visualized by 1 min of staining with Coomassie Brilliant Blue followed by destaining in 10% acetic acid-5% methanol. The stained bands were cut out from the dried membranes for amino-terminal sequence determination. Western blots on nitro-cellulose membranes were prepared using a primary polyclonal antibody against a 16-residue N-terminal sequence of BoNT/A LC and a peroxidase-coupled goat anti-rabbit IgG (H+L) as the secondary antibody (Ahmed and Smith, 2000).

Example 17

Proteolysis Experiments

Before each experiment, aliquots of the protein were thawed to room temperature and were immediately passed through a PD-10 column to remove the EDTA. The protein was collected in buffer P and stored on ice. The EDTA-free BoNT/A LC was mixed with predetermined concentrations of $ZnCl_2$, EDTA, TPEN, or the inhibitor peptide and 20–50 μL was distributed in screw-capped Eppendorf tubes. The tubes were incubated at 4° C. or at 22° C. The final concentration of the protein was 0.18–0.20 mg/ml in these incubation mixtures. At various time intervals an equal volume (20–50 μl) of SDS-load buffer was added to a tube for SDS-PAGE analysis.

A 100 mM stock solution of TPEN was prepared in ethanol (95%). Stock solutions of the competitive inhibitor peptide Ac-CRATKML-$NH_2$ (SEQ ID NO:46) (Schmidt et al., 1998) (5 mM), $ZnCl_2$ (1–4 mM), and EDTA (20 mM) were prepared in buffer P. Unless otherwise mentioned, final concentrations of these reagents in the incubation mixtures with the LC were TPEN 5 mM, EDTA 5 mM, peptide 1 mM, and $ZnCl_2$ 0.25 mM.

Results: Cleavage and Fragmentation of BoNT/A LC

Figure 10:
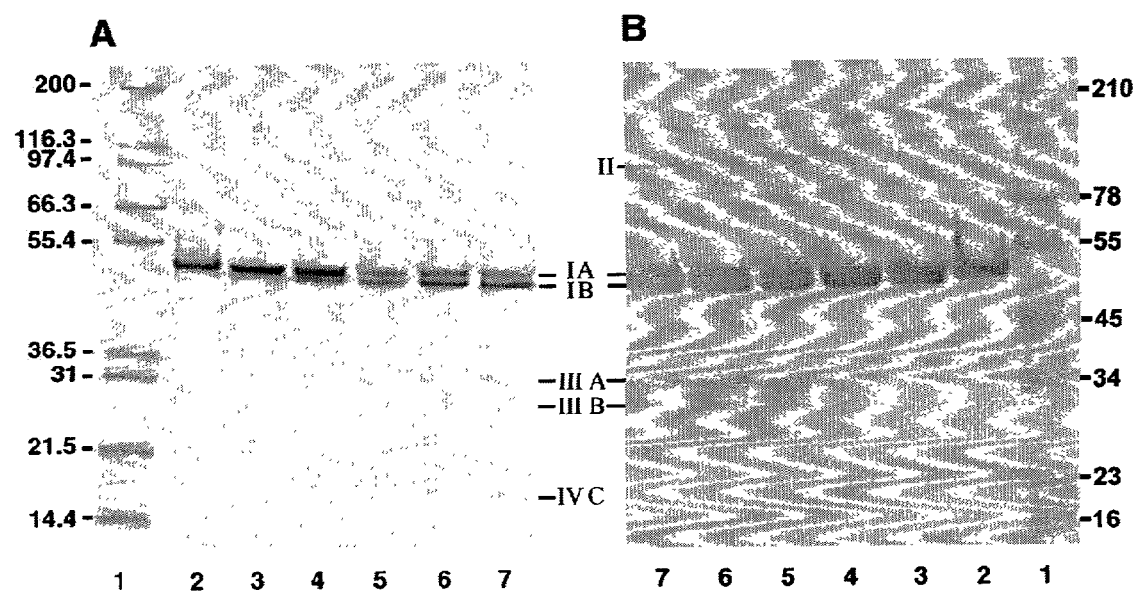
FIG. 10. Time course of proteolysis of BoNT/A LC as followed by SDS-PAGE (A) and Western blot (B). Aliquots of 25 ml of the LC (0.2 mg/ml) were incubated at 4° C. At intervals (see below), 25 μl of 2×SDS-load buffer was added to an aliquot and boiled. Two SDS gels were run in parallel. One gel was stained by Coomassie (A) and the proteins from the other were transferred to a nitrocellulose membrane for Western blot (B). Lane 1 in panel A shows Novex Mark-12 molecular weight markers and lane 1 in panel B shows the Novex prestained SeeBlue molecular weight markers. In both panels A and B, lanes 2–7 show 0, 2, 4, 14, 21, and 28 days of incubation, respectively, of LC. Identity of the protein bands between panels A and B is arbitrary, and the same nomenclature is used throughout the paper.

FIG. 10 shows that the BoNT/A LC undergoes cleavage and fragmentation that increases with time. The intensity of the band representing the full-length LC with a polypeptide mass of ~52 kDa (IA) gradually diminished with time and a new protein band of ~50 kDa (IB) appeared in its place. The results suggest truncation of about 2 kDa mass from the full-length LC. In Western blots (FIG. 10B), both IA and IB also reacted with a rabbit polyclonal antibody raised against a 16-residue amino-terminal sequence of LC. This result suggests that the truncation from the full-length LC must occur at the C-terminus. Indeed, amino-terminal sequencing of the isolated, truncated protein showed the amino terminus was intact. Interestingly, preservation of the N-terminus of full-length BoNT/A neurotoxin was also observed after its posttranslation modification in bacterial culture (DasGupta and Dekleva, 1990). As the truncated protein IB accumulated, a protein band of ~100 kDa (II) appeared that was detected easily in the Western blot (FIG. 10B). FIG. 10 also shows that at 2 weeks of incubation, the LC fragmented into IIIA+IIIB and IVC. The larger fragment (IIIA) above the 34-kDa marker was followed by a fainter fragment (IIIB) just below the 34-kDa marker. The results of this time course experiment also suggested that IIIB was formed from IIIA. Both of these fragments must represent the N-terminus of the LC, as they reacted with the antibody (FIG. 10B). On the other hand, a much smaller fragment (IVC) moving faster than the 23-kDa marker was probably the C-terminal fragment, as it failed to react with the antibody (specific for the N-terminus of the LC) in the Western blot. The truncation and fragmentation shown in FIG. 10 were independent of the batch of E. coli cell culture or the batch of purification of the LC.

Results: Zinc Accelerates the Truncation and Fragmentation

Figure 11:
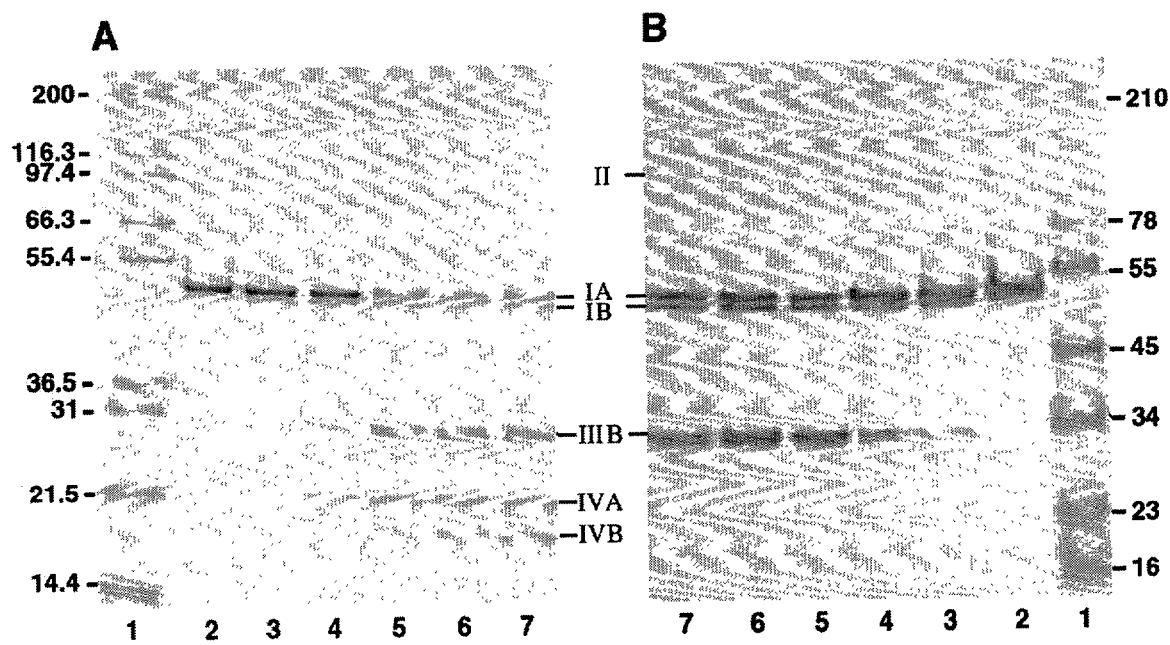
FIG. 11. Enhancement of the proteolysis of BoNT/A LC by $ZnCl_2$ as followed by SDS-PAGE (A) and Western blot (B). All conditions are same as in FIG. 10, except that 0.25 mM $ZnCl_2$ was added to the incubation mixture of the LC.

The BoNT/A LC is known to be highly substrate specific. Therefore, the truncation of about 2 kDa from the C-terminus or fragmentation into larger fragments upon storage of the LC at 4° C. described in FIG. 10 might appear to be due to the presence of some contaminating protease in the LC preparation. However, no additional Coomassie-stained protein bands were detected when 0.4–4.0 μg of the LC was electrophoresed in the presence of SDS. BoNT/A LC is a zinc-endopeptidase. FIG. 11 shows that when LC was incubated with 0.25 mM $ZnCl_2$, the rate of fragmentation was greatly increased so that the antibody-reacting fragment IIIB and an antibody-nonreacting fragment IVA appeared within 2 days of incubation (FIG. 11A, B). Fragment IVB appeared later in the time course. Qualitatively, the results are similar to those in FIG. 10 except that in the presence of $ZnCl_2$, the rate of fragmentation was higher, fragment IIIB was formed without showing the initial formation of IIIA, and initial formation of IVA gave rise to IVB. The rate enhancement by zinc could be partly due to formation of holo-LC from the partially Zn-resolved LC (see Section 2). Because there was no fragment IVC (FIG. 10) detected in this experiment (FIG. 11), zinc must also have a structural role in the LC. From the results shown in FIG. 11A it is not possible to judge if the C-terminal truncation of IA in forming IB and dimerization in forming II precede the fragmentation into III and IV. However, in some other experiments, using a lower concentration of $ZnCl_2$, it was possible to show that formation of IIIB occurred before formation of IB and that fragmentation was the last event.

The rates of C-terminal truncation and fragmentation of LC either in the absence or in the presence of $ZnCl_2$ were much higher when incubated at 22° C. than at 4° C. In fact, amino-terminal sequence was determined on the fragments generated by incubation at 22° C. for 2 days only.

Results: Metal Chelator TPEN Inhibits Truncation and Fragmentation

Figure 12:
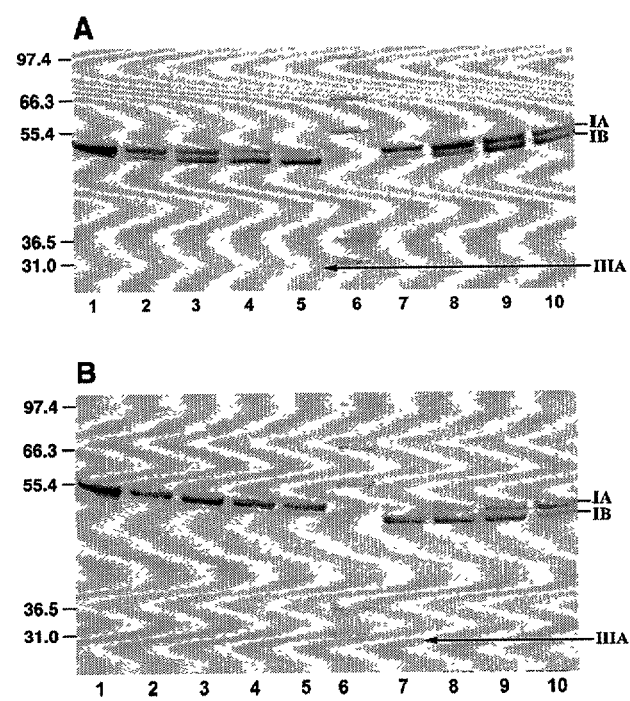
FIG. 12. Protection of BoNT/A LC from proteolysis by the metal chelator TPEN (A) and the competitive peptide inhibitor CRATKML (SEQ ID NO:46) (B), followed as a time course by SDS-PAGE. (A) the LC (0.2 mg/ml) was incubated in small aliquots with 10 mM EDTA (lanes 2–5) or with 5 mM TPEN (lanes 7–10). Lanes 2 and 7, 3 and 8, 4 and 9 and 5 and 10 show 6, 14, 21, and 28 days of incubation, respectively, (B) The LC was incubated with 1 mM peptide inhibitor containing 5 mM DTT (lanes 2–5) or without the peptide inhibitor (lanes 10–7) at 4° C. DTT, which does not have an effect on proteolysis, was added to maintain the peptide in monomer form. Lanes 2 and 10, 3 and 9, 4 and 8, and 5 and 7 show 6, 14, 21 and 28 days of incubation, respectively. In both panels A and B, lane 1 represents LC alone at day 0, and lane 6 has molecular weight markers (labels on left). The protein band IIIA (see FIG. 10) was faint in this experiment and was not captured in the photographic reproduction; therefore its location in the original gel is shown by arrows in the figure. Note that (a) presence (lanes 2–5, A) and absence (lanes 10–7, B) of EDTA had little effect on proteolysis of IA to IB and finally to IIIA, (b) TPEN (lanes 7–10, A) significantly reduced the rate of conversion of IA to IB and prevented formation of IIIA during the course of the experiment, and (c) the peptide inhibitor (lanes 2–5, B) drastically reduced the proteolysis of IA to IB and prevented the formation of IIIA.
Figure 13:
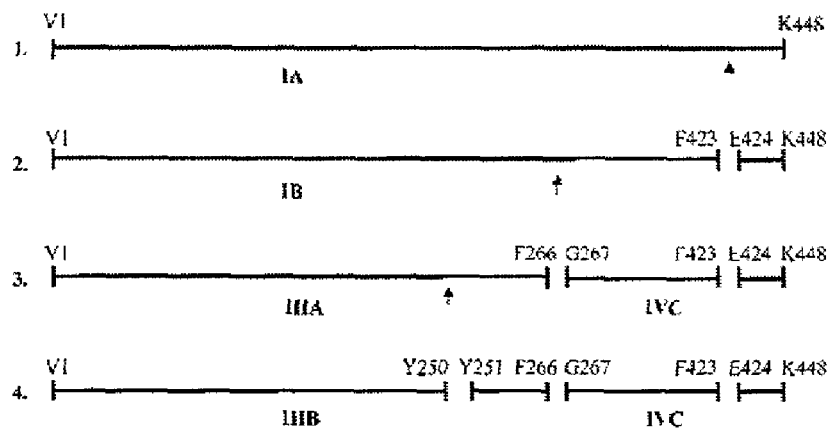
FIG. 13. Scheme I. Steps in the self-proteolysis of BoNT/A LC in the absence of added zinc. Arrows show the sites of proteolysis. Full-length LC is denoted by IA. The fragments IB, IIIB, and IVC correspond to the fragment designations in FIG. 10. The primary event is the C-terminal truncation to form IB followed by cleavage between Y286 and G287 producing IIIA and IVC. The fragment IIIA in turn is further proteolyzed between Y251 and Y252 to generate IIIB. Lengths of the fragments (e.g., IV-K448) are based on mass determined by MALDI-MS and N-terminal amino acid sequence shown in Table 5. The C-terminal peptide E424–K448, although shown here as a single peptide for convenience, is in fact a mixture of several peptides (see Tables 4 and 5).
Figure 14:
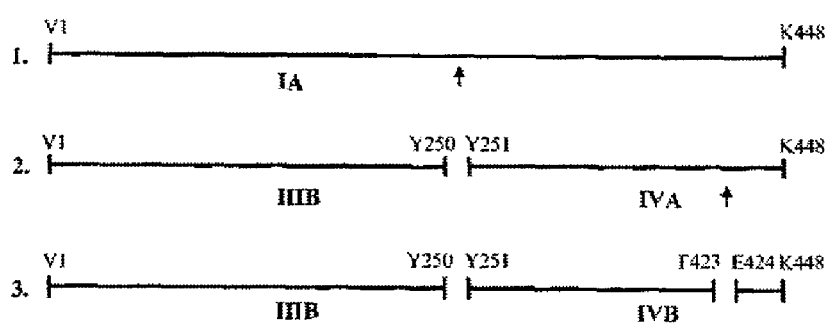
FIG. 14. Scheme II. Steps in the self-proteolysis of BoNT/A LC in the presence of added zinc. Arrows show the sites of proteolysis. The fragments IIIB, IVA, and IVB correspond to the fragment designations in FIG. 2. Unlike the steps shown in Scheme I, IA may bypass the C-terminal truncation and initial formation of IIIA but undergo proteolysis between Y251 and Y252 in directly forming IIIB. The fragment IVA is further cleaved into IVB. Although a C-terminal cleavage of IVB into IVC is possible, it was not observed here (see FIG. 11) this species in the presence of added zinc. See FIG. 11 and Scheme I for other explanations.

As shown in FIG. 11, if the C-terminal truncation and fragmentation of the LC was indeed dependent on the presence of zinc, removing zinc from the incubation mixture and from the active site of the LC would be expected to abolish the truncation and fragmentation events. However, zinc is very tightly bound to the active site of LC. Extensive treatment with 10 mM EDTA in the cold (Ahmed and Smith, 2000) or with 10 mM EDTA at room temperature (Li and Singh, 2000) failed to completely remove zinc from the active site of the LC. In agreement with these observations, including 10 mM EDTA failed to protect the LC from C-terminal truncation and processing (FIG. 12A). In contrast, the metal chelator TPEN largely protected the LC from truncation and fragmentation (FIG. 12A). It was also found that, at 1 mM TPEN, the LC showed no activity when assayed for 5 min. Because the incubation mixture with TPEN did not contain any exogenous metal or zinc, any chelation by TPEN must have involved the active-site zinc of the LC. These results also suggest that truncation and fragmentation of the LC upon storage 4° C. or at room temperature were autocatalytic.

Example 18

Separation of Peptides with HPLC and Their Characterization by ESIMS-MS

For mass and sequence determination, peptides were separated on an Agilent Technologies Series 1100 liquid chromatograph with a 0.8×100 mm Poros-2 R/H column (PerSeptive Biosystems, Inc.). The mobile phase was 0.1% formic acid (solvent A) and 80% acetonitrile in 0.1% formic acid (solvent B). The peptides were eluted with a linear gradient of 0–100% B over 15 min at a flow rate of 0.2 ml/min. The injection volume was 10 μl. The peptides were detected and structurally characterized on a Finnigan LCQ Deca mass spectrometer employing data-dependent MS/MS. Molecular mass was also determined by MALDI-MS with a PE Biosystems Voyager DE instrument. Sinapinic acid was used as the matrix, and the sample was spotted on a stainless steel plate that was not washed with water or TFA. Other conditions in the experiment were accelerating voltage 25,000 V, guide wire voltage 0.3%, and laser 2500.

Results: Amino Acid Sequence of the Small Peptides Generated by C-Terminal Processing To map the sites of proteolysis, the small peptides were isolated by ultrafiltration of a C-terminally truncated LC mixture. Amino acid sequences of these peptides were determined by ESIMS-MS (Table 4). The peptides with G433 at the amino terminus (peptide 4) and K438 at the carboxy terminus (peptide 5) indicated cleavage by a trypsin-like protease on the R432–G433 and K438–T439 bonds, respectively. Of these, only the lysyl bond at K438 was reported to be cleaved by a clostridial endogenous protease or by trypsin (DasGupta and Dekleva, 1990). However, a cleavage at the K444–G445 bond as reported before by an endogenous clostridial protease (DasGupta and Dekleva, 1990) was not detected. Neither was cleavage detected at K440–S441 or at K427–L428 bonds, the other potential sites of tryptic cleavage. Although these results indicated that the LC preparations did not contain a protease activity that could cleave at K427–L428, K440–S441, and K444–G445, it is equally possible that some of the small peptides generated by cleavage at these sites were lost during sample preparation. Interesting findings of this experiment (Table 4) are the peptides with N-terminus of T420 (peptide 1) and V431 (peptide 3), as the preceding residues at F419–T420 and C430–V431 bonds, respectively, are certainly not the sites of "tryptic" cleavage.

The sequence data from the ESIMS-MS results for the peptides 2 and 5 agree very well with the residue stretches V432–K449 and with the residue stretches V432–K449 and with the residue stretches V431–K438, respectively. However the experimentally determined mass for "C430", the residue at the amino side of V431 in both peptides, was greater by 12.1 Dalton than the theoretical mass for cysteine. At this stage, there is some uncertainty regarding the discrepancy in the mass of this "cysteine." Chemical modification experiments using iodoacetamide or acidified methanol failed to shift the masses of these peptides, indicating that the suspected "cysteine" did not have a free sulfhydryl group nor was a contaminating aspartic acid. Cysteine in proteins are known to occur as derivatives such as cysteine sulfenic acids (Ahmad and Claiborne, 1992; Claiborne et al., 1999). Attempts are being made to decipher the chemical nature of this "cysteine." If indeed it was a modified C430, cleavages at the carboxy ends of F419, C430, and V431 in addition to R432, K438, and K438 indicate that the proteolytic activity in this preparation was not "tryptic" in nature, but had a broad specificity.

Results: Identity of the Large Peptides Generated by Fragmentation

The large peptides generated by fragmentation in the middle of the LC were identified by comparing the mass determined by MS with a calculated mass for a stretch of sequence based on the amino-terminal sequence determination (Table 5). Agreements between the experimental and calculated values were within 0.07%. Identity of IIIA as having a sequence range of V1–F266 was based on the kinetics of its (and of IVC's) appearance on SDS-PAGE (FIGS. 10 and 11) and N-terminal sequence of IVC. The sequence data along with Western blot results clearly demonstrated that the amino terminus of the LC (IA and IB) remained unchanged during the prolonged incubation period. Although the C-terminal sequence of the peptides IIIA and IIIB was not determined, N-terminal sequences of the peptides IVA, IVB, and IVC (Table 5) indicate that fragmentation of IA and IB (FIGS. 10 and 11) occurred by cleavage at the Y250–Y251 and F266–G267 bonds. Again, if the cleavages of these tyrosyl and phenylalanyl bonds were catalyzed by a protease, it must have been "nontryptic" in nature. Identity of the peptides IVB and IVC as having F423 at the C-terminal indicated that a C-terminal processing of the LC at F423–E424 remained undetected in the small peptide isolation experiment (see previous section).

TABLE 4

C-Terminal Peptides Generated after Initial Cleavage of the BoNT/A LC[a]

| Peptide | Mass[b] | 420  425  430  435  440  445<br>KNFTGLFEFYKLLCVRGIITSKTKSLDKGYNK[c] |
|---|---|---|
| 1 | 2188 (2188) | TGLFEFYKLLCVRGIITSK |
| 2 | 2124 (2112)[d] | CVRGIITSKTKSLDKGYNK[d] |
| 3 | 2008 (2008) | VRGIITSKTKSLDKGYNK |
| 4 | 1753 (1753) | GIITSKTKSLDKGYNK |
| 5 | 989 (977)[d] | CVRGIITSK[d] |

[a]The peptides were generated by incubating 0.4 mg of the LC in 0.5 ml of buffer P at 4° C. for 2 weeks. They were isolated by ultrafiltration through a Centricon CM10 (Amicon) membrane that was previously treated with 10 mM EDTA. The filtrate containing the peptides was stored at −20° C. for 1 week before mass and sequence determinations by ESIMS-MS. The sequence on the first row with the numbers above it represents the known C-terminal sequence of the LC (Ahmed and Smith, 2000).
[b]Experimentally determined mass from ESI-MS; calculated mass for the sequence shown is given in parentheses.
[c]Residues 417–448 of SEQ ID NO:5
[d]The calculated mass was 12.1 Da smaller than the experimental value. Except for cysteine in peptides 2 and 5, the experimentally determined masses of all other amino acid residues agree well with their calculated values. Note that cysteine in peptides 2 and 5 occurred at the N-terminus, but when it was in the middle of the peptide, there was no ambiguity in the results.

This result nonetheless supports that C-terminal processing occurred at phenylalanyl bonds in addition to lysyl, arginyl, valyl, and (most likely) cysteinyl bonds.

TABLE 5

Identity of the Polypeptides Generated by Proteolysis of the BoNT/A LC

| Peptide[a] | Mass (Exp) | Mass (Calc) | Sequence range | N-terminal sequence |
|---|---|---|---|---|
| IA | 51,315 | 51,318 | V1–K448 | 2-VQFVNKQ |
| IB | 48,866 | 48,870 | V1–Y426 | 2-VQFVNKQ |
| II | 97,727[b] | | | |
| | 97,870[b] | | | |
| IIIA | n.d.[c] | 32,270 | V1–F266 | 2-VQFVNKQ |
| IIIB | 28,111 | 28,130 | V1–Y251 | 2-VQFVNKQ |
| IVA | 23,207 | 23,207 | Y252–K448 | 252-YEMSGLE |
| IVB | 20,319 | 20,319 | Y252–F423 | 252-YEMSGLE |
| IVC | 18,400 | 18,400 | G267–F423 | 267-GGHDAKF |

[a]Peptide designations are from FIGS. 10 and 11. Mass was determined by ESIMS-MS. Masses of the peptides IA and IB were determined separately. Peptides were generated by incubating the LC (1.8 mg/ml buffer P) alone or in the presence of 0.25 mM $ZnCl_2$ for 2 days at 22° C. Partial precipitation of the protein was visible after 1 day and was removed by centrifugation before ESI analysis. Masses of IIIB, IVA, and IVB were determined in samples containing $ZnCl_2$ and those of IA, IB, IIIA, and IVC were determined in samples with no $ZnCl_2$. Calculated masses are for the sequence ranges shown based on N-terminal sequence and mass data. The N-terminal sequences were determined separately for IA, IB, and IIIA in solutions and for IIIB, IVA, IVB and IVC on PVDF membrane after separation by SDS-PAGE and transfer on membrane.
[b]Data from MALDI-MS determined in a sample containing IB with an initial concentration of 0.2 mg/ml.
[c]Mass could not be detected in several experiments, probably due either to precipitation or to irreversible binding to column resin. Although a peptide with a lower mass can have slower mobility than a homologous higher mass peptide in SDS-PAGE due to charge differences (Ahmed et al., 1986), the kinetics of appearance of IIIB from IIIA (FIG. 1) and their identification by N-terminal sequence determination suggest that IIIA must be larger than IIIB. Identity of IIIA as having a sequence of V1–F266 with a mass of 32,270 was based on N-terminal amino acid sequence determination and SDS-PAGE results (FIGS. 10 and 11).

Example 19

Other Analytical Methods

The enzymatic assay was based on HPLC separation and measurement of the nicked products from a 17-residue C-terminal peptide of SNAP-25 corresponding to residues 187–203 (Schmidt and Bostian, 1995). Initially protein concentrations were determined by BCA assay (Pierce) with bovine serum albumin (BSA) as a standard. After it was established by repeated measurements that a 1-mg/ml BoNT/A LC thus determined has $A^{0.1\%}$ (1 cm light path) value of 1.0 at 278 nm (0.98 at 280 nm), protein concentration was determined from absorbance at 278 nm. For comparison, the calculated $A^{0.1\%}$ value of the LC at 280 nm in water (Pace et al., 1995) is 0.948. Absorption spectra were recorded in a Hewlett-Packard 8452 diode array spectrophotometer. The N-terminal amino acid sequence of the LC was determined by Edman degradation in the Applied Biosystems Procise Sequences in the 0- to 20-pmol detection range.

Example 20

A Specific Competitive Inhibitor of LC Activity Was an Effective Inhibitor of Truncation and Fragmentation Autocatalytic truncation and fragmentation of proteins can arise from chemical catalysis and from enzymatic catalysis. To differentiate these two possibilities, a peptide specifically synthesized as a competitive inhibitor of BoNT/A proteolytic activity (Schmidt et al., 1998) was used. This peptide inhibitor, with a sequence of CRATKML (SEQ ID NO:46), competitively inhibits the cleavage of a 17-residue substrate peptide based on SNAP-25 by BoNT/A neurotoxin with a $K_i$ of 2 uM (Schmidt et al., 1998). At a 1 mM inhibitor peptide concentration, the LC showed no activity when assayed for 5 min. FIG. 12B shows that when the LC was incubated with 1 mM peptide inhibitor, both C-terminal truncation and fragmentation at the interior of LC were largely prevented. In the presence of the peptide inhibitor, however, the LC underwent a very slow cleavage, as can be expected in an enzymatic activity with a competitive inhibitor. Densitometric scanning of the gel showed that after 28 days, in the presence of the peptide inhibitor, less than 10% of the LC (IA) was converted into the C-terminally truncated form (IB). In contrast, in the absence of the peptide inhibitor, more than 80% of the LC (IA) was converted into the truncated form (IB). Results of this experiment prove that loss of 10–28 residues from the C-terminus of LC followed by fragmentation into two major peptides (FIGS. 10 and 11, Tables 4 and 5) occurred at the active site of the LC and that these reactions were enzymatic. The results also provide direct evidence that the cleavage reactions were not due to any contaminating protease in the preparation of the LC.

Example 21

Materials

PCR-TOPO and 1-Shot cells were from Invitrogen. pET24a plasmid and BL21 (DE3) cells were obtained from Novagen. All were prepared by standard methods. Proteins were visualized by SDS-PAGE and stained either with Coomasie or Colloidal Coomasie (Novex). Westerns (Novex) were reacted with a rabbit primary antibody (Research Genetics, Inc., Huntsville, Ala.) against the N-terminal 16 amino acids (PFVNKQFNYKDPVNGV; SEQ ID NO:1) of the LC of type A and were visualized with a horseradish peroxidase conjugated goat anti-rabbit secondary anti-body and TMB peroxidase substrate (Kirkegaard and Perry Laboratories). Bacterial media was from Difco. Purification of the expressed proteins was on a Pharmacia model 500 FPLC system with programmed elution and $A_{280}$ monitoring (Pharmacia, Uppsala, Sweden). Columns were a Pharmacia HR 10/10 Mono S cation-exchange column, a Pharmacia Mono S 5/5 cation exchange column, and a Perseptive Biosystems POROS 20 HS cation exchange column. Pretreatment of the expressed proteins was with DNase (Sigma, Inc.) and dialysis was with Pierce Slide-A-Lyzer 10k MWCO cassettes. The SNAP-25 substrate peptide (Quality Controlled Biochemicals, Hopkinton, Mass.) and its cleavage products were separated on a Hi-Pore C18 column, 0.45×25 cm (Bio-Rad Laboratories) and analyzed with the Millennium Software Package (Waters, Inc.). Src (p60c-src) recombinant phosphokinase, substrate peptide, and anti-phosphotyrosine monoclonal antibody 4G10 were from Upstate Biotechnology, Lake Placid, N.Y. [$\gamma$-$^{32}$P]ATP, 3000 Ci/mmol, was from Dupont-NEN.

Example 22

Preparation of Recombinant Neurotoxin Clones

New restriction sites were added by PCR to the 5' and 3' ends (NdeI and HindIII, respectively) of the synthetic DNA molecules coding for the Lc ($M_1$ to $K_{449}$), the Lc plus belt (LC+Belt; $M_1$ to $F_{550}$) and the Lc plus translocation region (LC+Xloc; $M_1$ to $Q_{659}$). These sequences correspond to GenBank accession numbers x, y and z respectively. PCR products were subcloned into pCR-TOPO and the sequences confirmed by DNA sequencing. The inserts were cut from the subcloning vector and ligated behind the NdeI site of pET24a, so as to begin expression with the initial methionine of the LC. The plasmid was transformed into *E. coli* BL21 (DE3) cells for expression.

Example 23

Expression of Neurotoxins

One hundred ml of Terrific Broth (TB) plus kanamycin was inoculated with the appropriate clone and grown overnight, with shaking, at 37° C. Fifty ml of LcA or 100 ml LcA+Belt and Lc+Hn of overnight growth was added to 1 liter TB plus kanamycin and shaking incubation continued at 37° C. for an additional 1.25 hours. While cultures were placed on ice for 5 to 10 minutes, the $OD_{600}$ was read and adjusted to approximately 0.4 to 0.6, then IPTG was added to 1 mM for induction of protein expression. Duplicate cultures were grown at 37° C. (4 hours), 30° C. (10 hours) and 18° C. (22 hours). At harvesting, the $OD_{600}$ was read again, cells were pelleted and frozen at −70° C. if not used immediately. Data points are the mean of three separate measurements of the appropriate bands from SDS-PAGE gels scanned and digitally analyzed with an AlphaImager 2000 densitometer and AlphaImager Documentation and Analysis Software (AlphaInotech, San Leandro, Calif.).

Figure 15A:
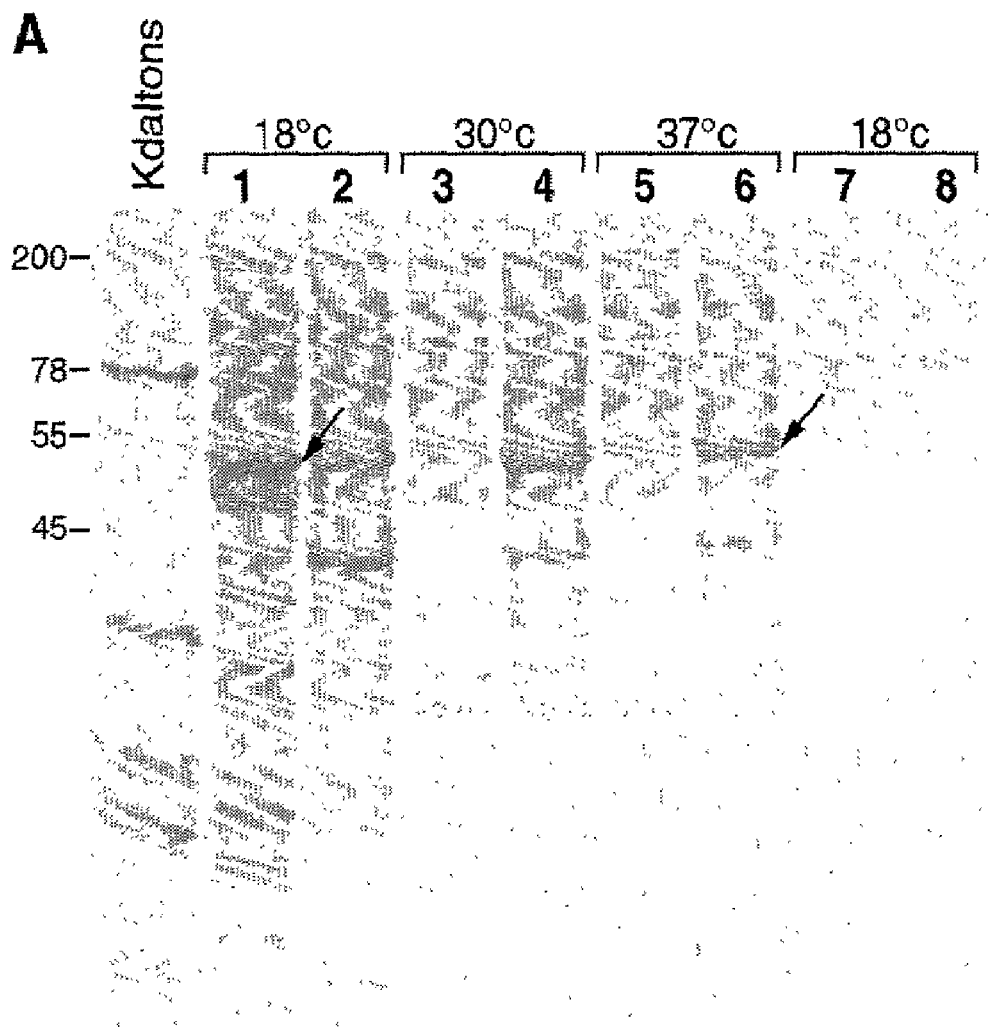
FIG. 15. SDS-PAGE of (A) LCA, (B) LCA+Belt, and (C) LCA+Xloc, expressed at 18° C., 30° C. and 37° C. Odd numbered lanes (1, 3, 5 and 7) are the soluble fractions and even number lanes (2, 4, 6 and 8) are the insoluble fractions. Lanes 7 and 8 are control cells with the plasmid lacking the insert. Arrows show the expressed product at 18° C. (soluble) and 37° C. (insoluble).
Figure 15B:
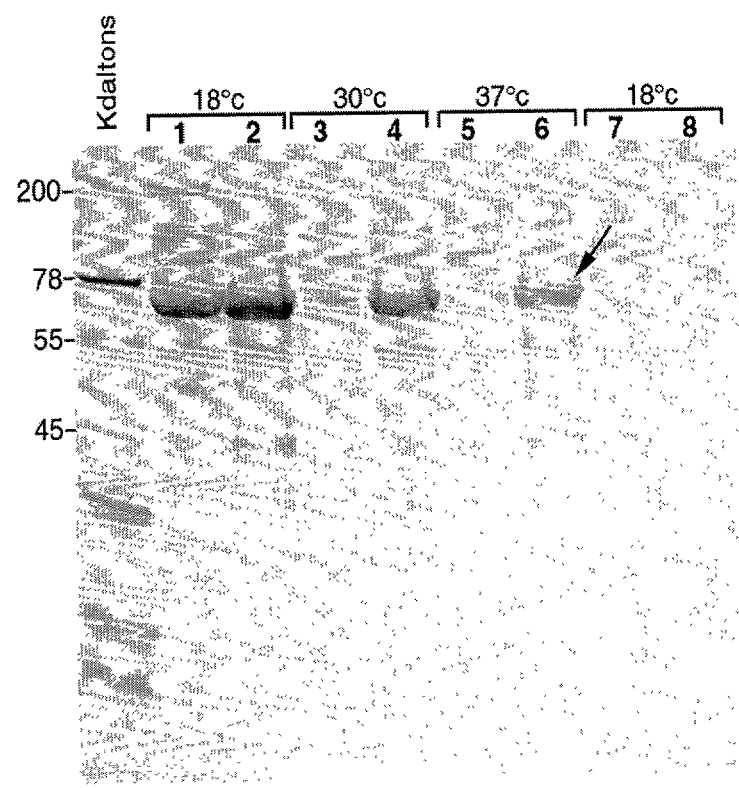
Figure 15C:
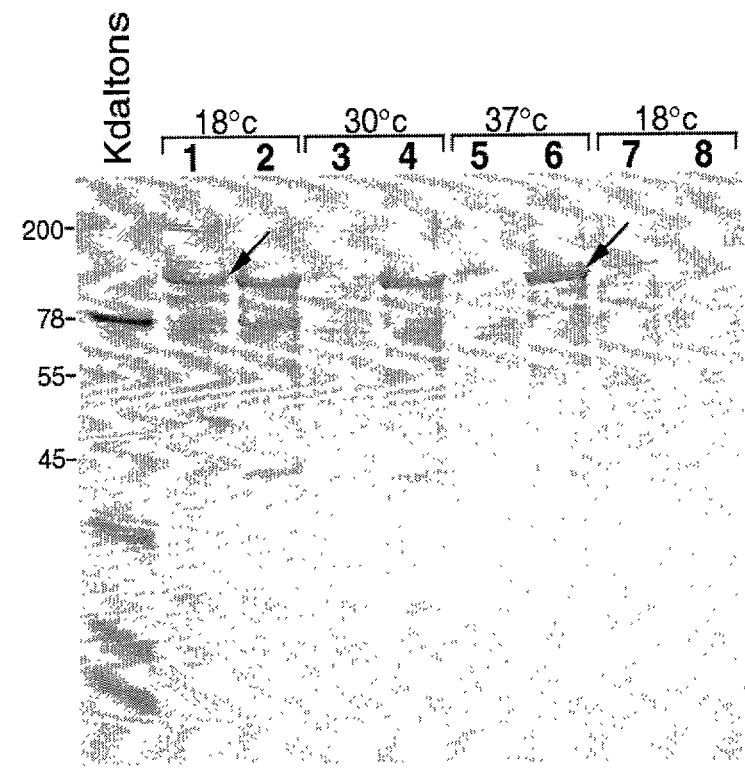

Expression at Low Temperatures Markedly Increases Yields of Soluble Product, While Addition of Portions of the Hn Does Not Increase the Yield of Soluble Product To study the effects of low temperature induction on the expression of LcA, expression was performed at 18° C., 30° C. and 37° C. FIG. 15A shows the decreasing solubility of LcA at these three temperatures, with concomitant decrease in the soluble product, from 55.5% at 18° C. to 5.2% at 37° C. Yields of soluble LcA were highest at 18° C., with LcA making up approximately 10% of the cell protein. Addition of the belt and Hn portions of the neurotoxin to LcA did not increase solubility (FIGS. 15A, 15B and 15C), although addition of the full Hn region reduced expression and yield (FIG. 15C).

Constructs were grown both in Luria Broth (LB) and Terrific Broth (TB), with no apparent difference in the quality or percent solubility of the products. Total yield was far greater for growth in TB, 17.97 g/l verses 7.77 g/l for LB. Optimal expression conditions for the Lc were considered to be the construct lacking either the belt or the Hn region at 18° C. for 20–24 hours in TB.

Example 24

Sample Preparation and Purfication of LC

One gram *E. coli* cell paste was resuspended into 20 ml of buffer A (20 mM NaAcetate, 2 mM EDTA, pH5.4). The suspended cells were disrupted by sonicating for 12 cycles of 30 seconds followed by 30 seconds of incubation on ice using a medium size probe at 65% output. The resulting cell lysate was centrifuged (Sorval) at 15,000×g for 15 minutes at 4° C. to separate the proteins into soluble and insoluble fractions. The soluble fraction was diluted 1:1 in equilibration buffer B (20 mM NaAcetate, 2 mM EDTA, pH5.8) and used as starting material for the chromatography.

A HR 10/10 Mono S cation-exchange column was extensively cleaned between runs by sequentially running through it: 1 M NaCl through at 3 ml/min for 5 minutes; 20 mM NaOH for 10 minutes at 1 ml/min; 70% ethanol in ddwater for 30 minutes at 1 ml/min; 1 M NaCl in buffer B for 15 minutes at 1 ml/min; then re-equilibrated with buffer B at 2 ml/min for 5 minutes. The diluted lysate was then loaded at a flow rate of 2 ml/min (150 cm/h). The column was washed with 24 ml (3 bed volumes) of buffer B. Flow through and wash were collected separately and stored for subsequent analysis. Protein was eluted from the column with a linear gradient from 0 to 70% 1 M NaCl in buffer B over 8 minutes. Two-ml fractions were collected throughout the gradient. Fractions eluting between 10 and 22 mSiemanns (mS) were positive for rBoNTA($L_c$) as shown by Western blot analysis. The pooled fractions were diluted 1:3 with buffer C (20 mM NaAcetate, 2 mM EDTA, pH6.2) and loaded onto a Mono S 5/5 cation exchange column equilibrated with buffer C at a flow rate of 2.5 ml/min. The column was washed with 10 ml (10 bed volume) of buffer C. Protein was eluted from the column with a linear gradient of 0–75% 1 M NaCl in buffer C over 15 minutes. The rBoNTA($L_c$) protein eluted from the Mono S column as a single band at 12 mS as shown by Western blot analysis. Fractions were pooled and stored frozen at −20° C. in plastic vials. The product was greater than 98% pure as determined by SDS-PAGE.

The LcA+belt and the LcA+Hn were similarly purified, except that sonication was in buffer A (20 mM NaAcetate, 2 mM EDTA buffer, pH 4.8) and dilution was not necessary after centifugation to obtain the soluble fraction. After extensive cleaning of the column, the soluble fractions of either LcA+Belt or LcA+Hn were loaded at 2 ml/min onto a Poros 20 HS column equilibrated with buffer A. After loading, the column was rinsed at 3 ml/min with buffer A for 5 minutes and a 5% step of 1 M NaCl in buffer A was performed to remove interferring cellular products. The LcA+Belt was then eluted with a 9% step and the LcA+Hn eluted with a 10–14% step of 1 M NaCl in buffer A. Fractions were pooled, diluted 1:3 with equilibration buffer A and re-run on the HS column, eluting with a 1 to 75% gradient of 1 M NaCl in buffer A. Verification of the peaks was by Western blot and SDS-PAGE. Each protein was 95% or greater pure. Fractions were pooled and stored frozen at −20° C. in plastic vials.

After the first column purification, aliquots of the expressed LcA+Hn were additionally nicked with trypsin at 10 μg/ml overnight, at room temperature. This semi-purified protein lysate was then diluted and run on a second Poros HS column as described above. Protein was similarly 95% or greater pure.

Total protein concentrations were determined by using either a Bio-Rad Protein assay at one-half volume of the standard protocol and bovine serum albumen as the protein standard or the Pierce BCA (bicinchoninic acid) protein assay with the microscale protocol as directed, with bovine serum alubumin as the protein standard.

Figure 16A:
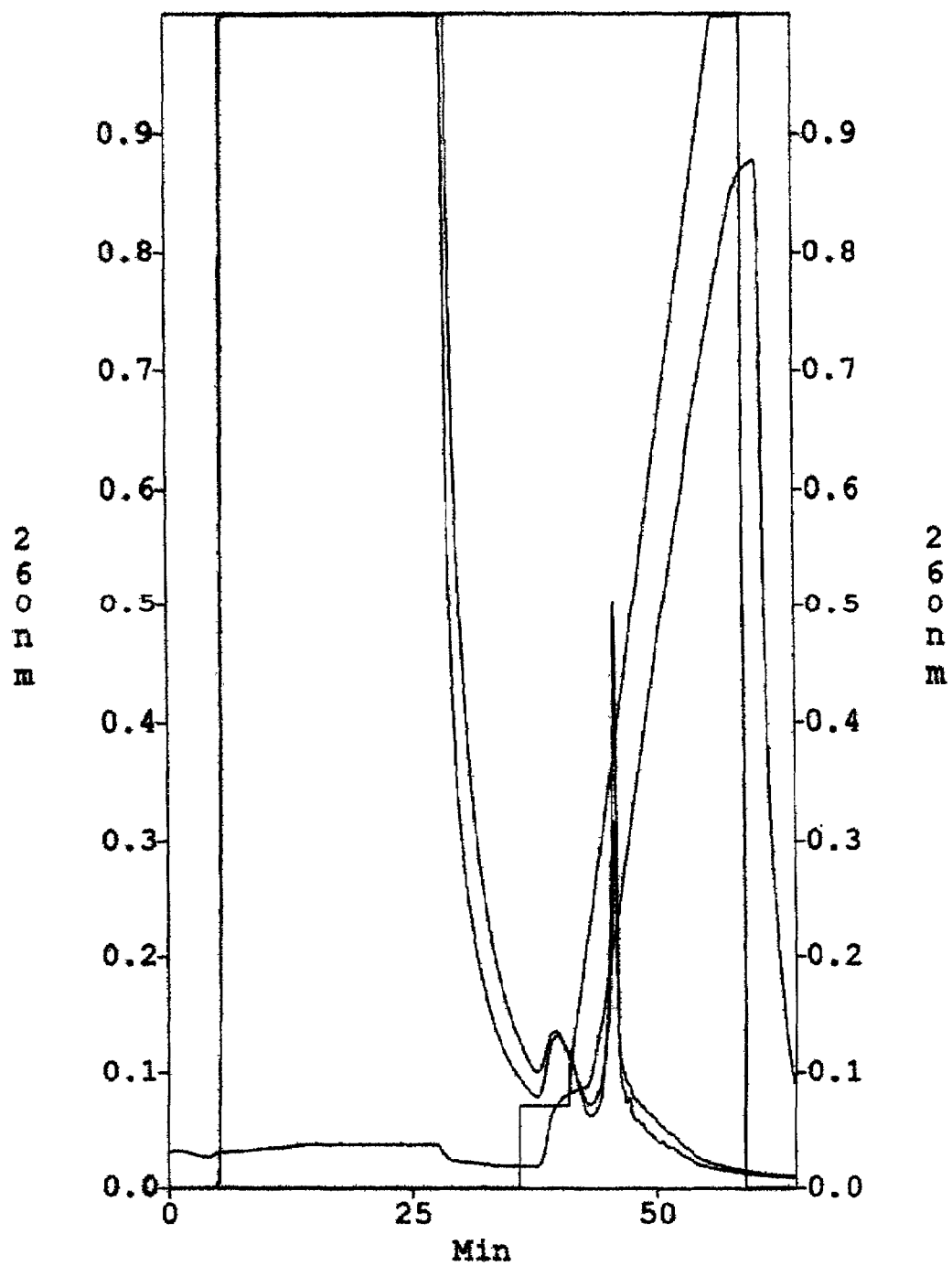
FIG. 16. HPLC elution profiles from HS column of LcA (A, B), LcA+Belt (C, D), LcA+Hn (E, F), and LcB (G,H) and from a Source S column of LcA (I, J).

Purification of the Lc From the Soluble Fraction of the Lowest Temperature Expressed Once conditions had been achieved for optimal yield of product, recovery of the Lc by simple cell sonication was deemed sufficient to release the protein. After removal of insoluble cell debris and proteins by centrifugation, this extract was directly loaded onto a cation exchange column and two isoforms of the Lc were observed to elute between 180 and 280 mM NaCl (FIG. 16A). Western analysis of collected fractions showed two peaks reactive to antisera, corresponding to a full length Lc, and a Lc truncated by approximately 2.5 kDa. Since both forms were reactive to the amino terminus specific sera, a carboxy terminus truncation was indicated. The calculated pI for a Lc lacking the terminal 21 residues is 6.39, suggesting that it would be eluted at a lower NaCl concentration, as was observed. This difference in elution conditions allowed for a separate purification of each Lc isoform. The products eluted from the cation exchange chromatography column were observed to be approximately 70% pure, with a total protein concentration of 1.1 mg/ml.

Figure 16B:
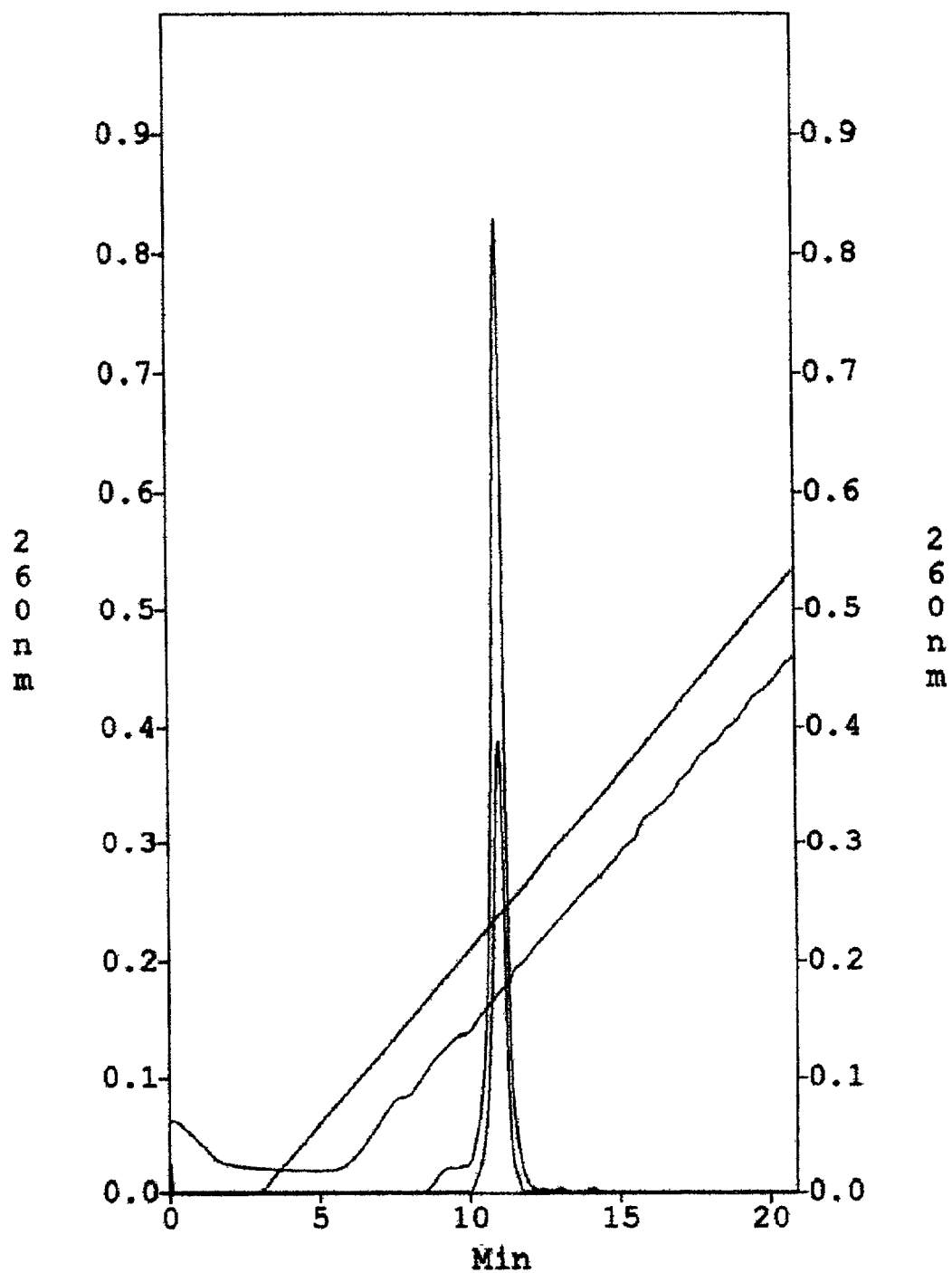
Figure 16C:
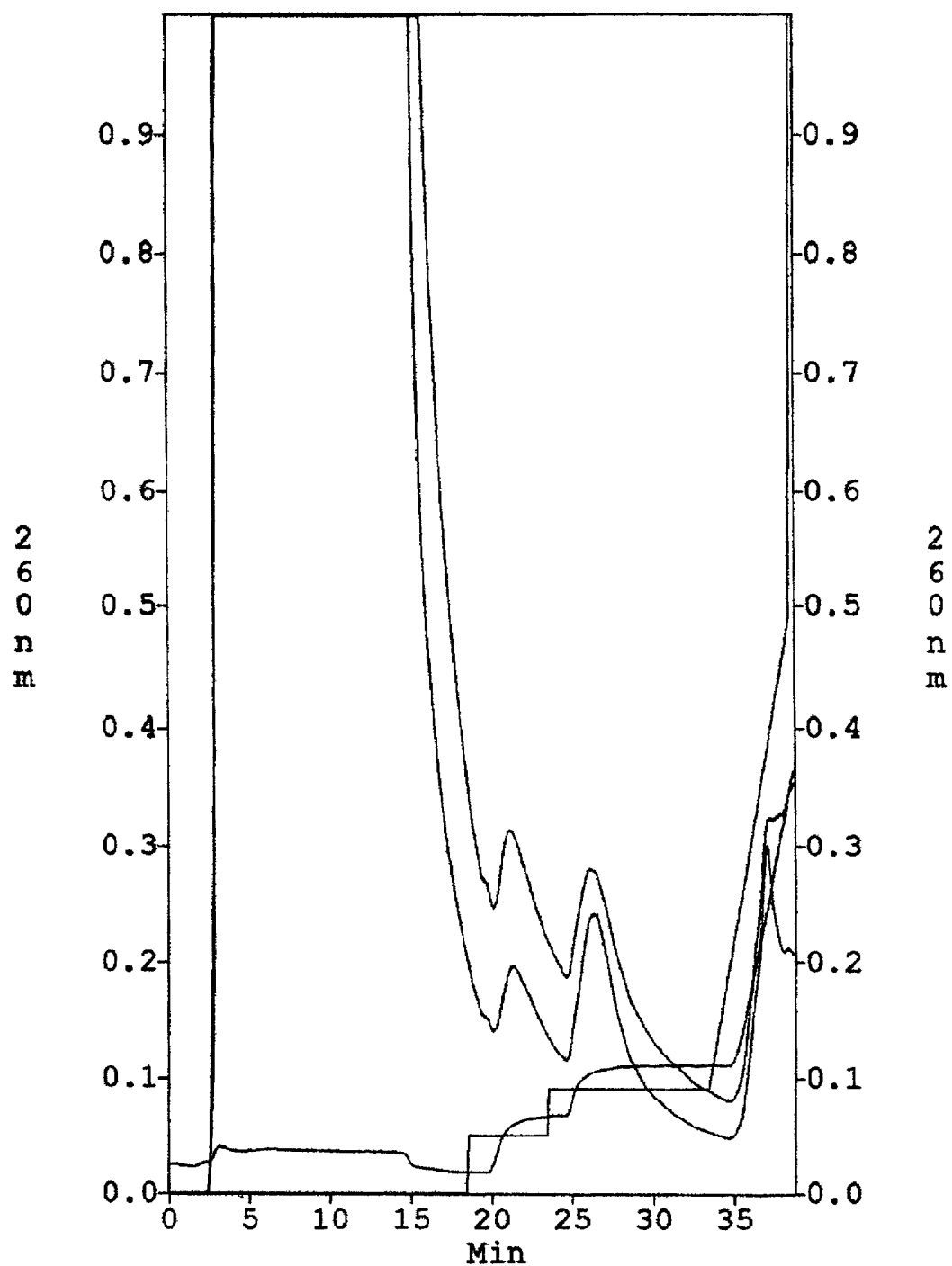
Figure 16D:
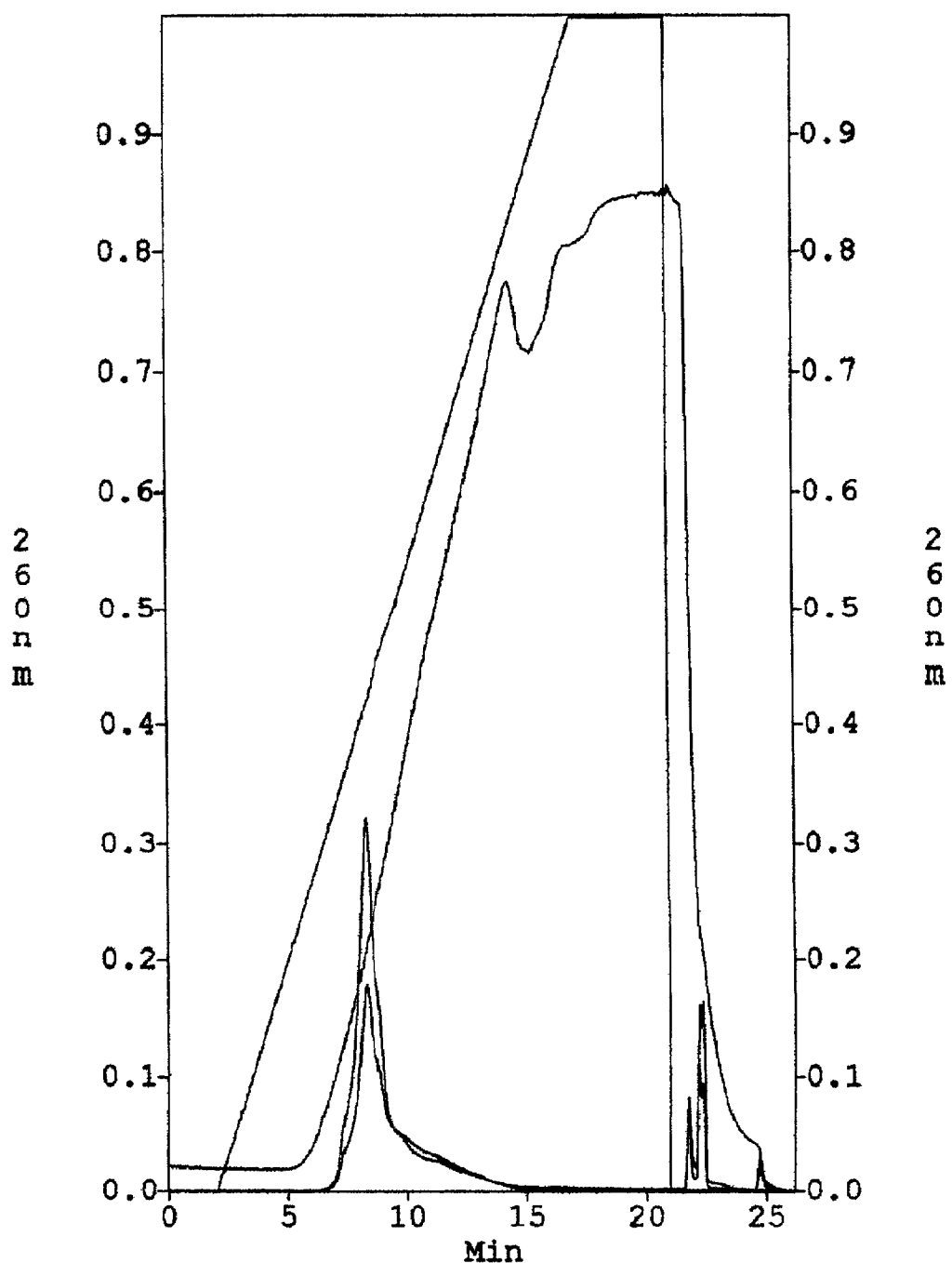
Figure 16E:
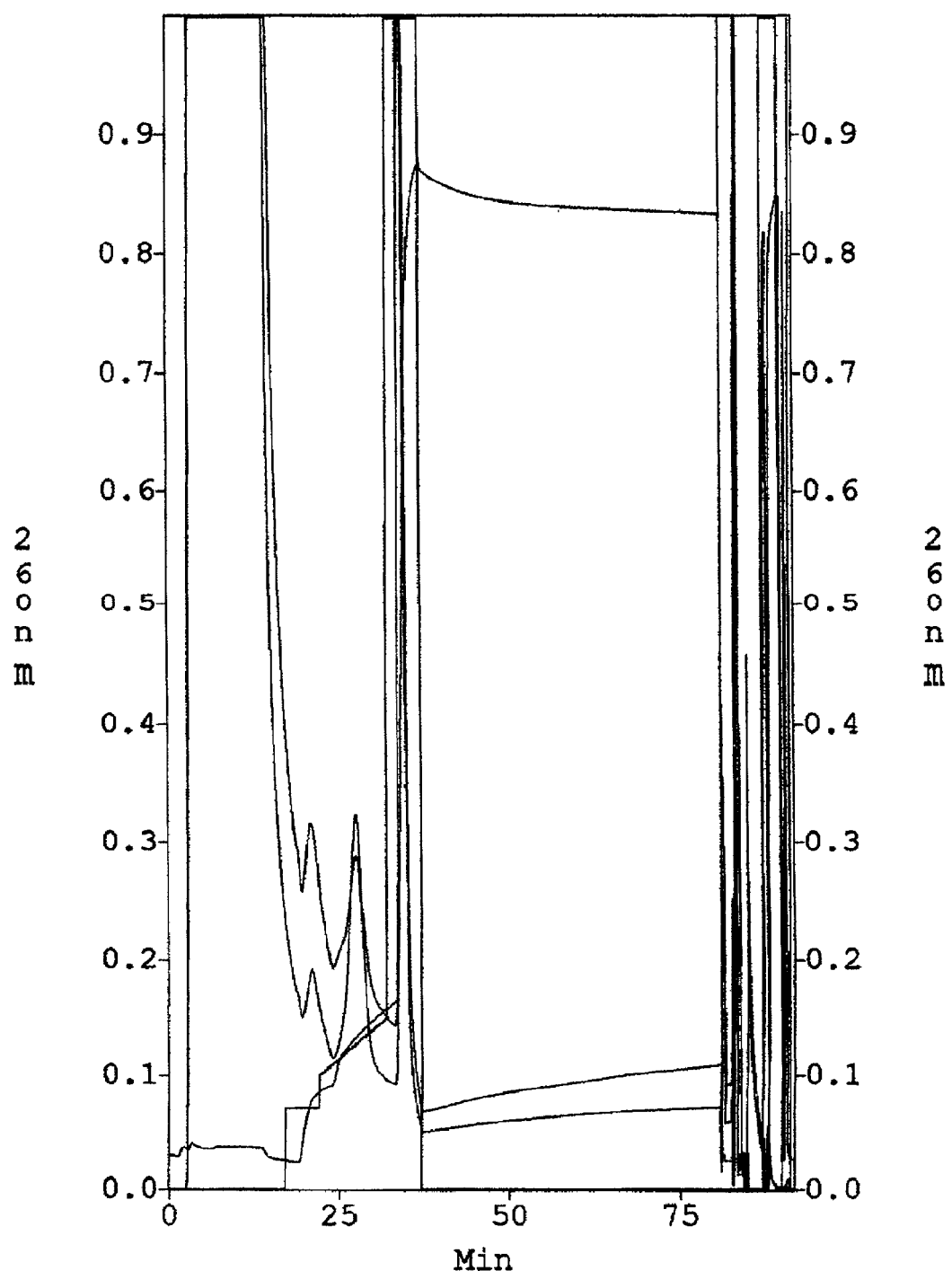
Figure 16F:
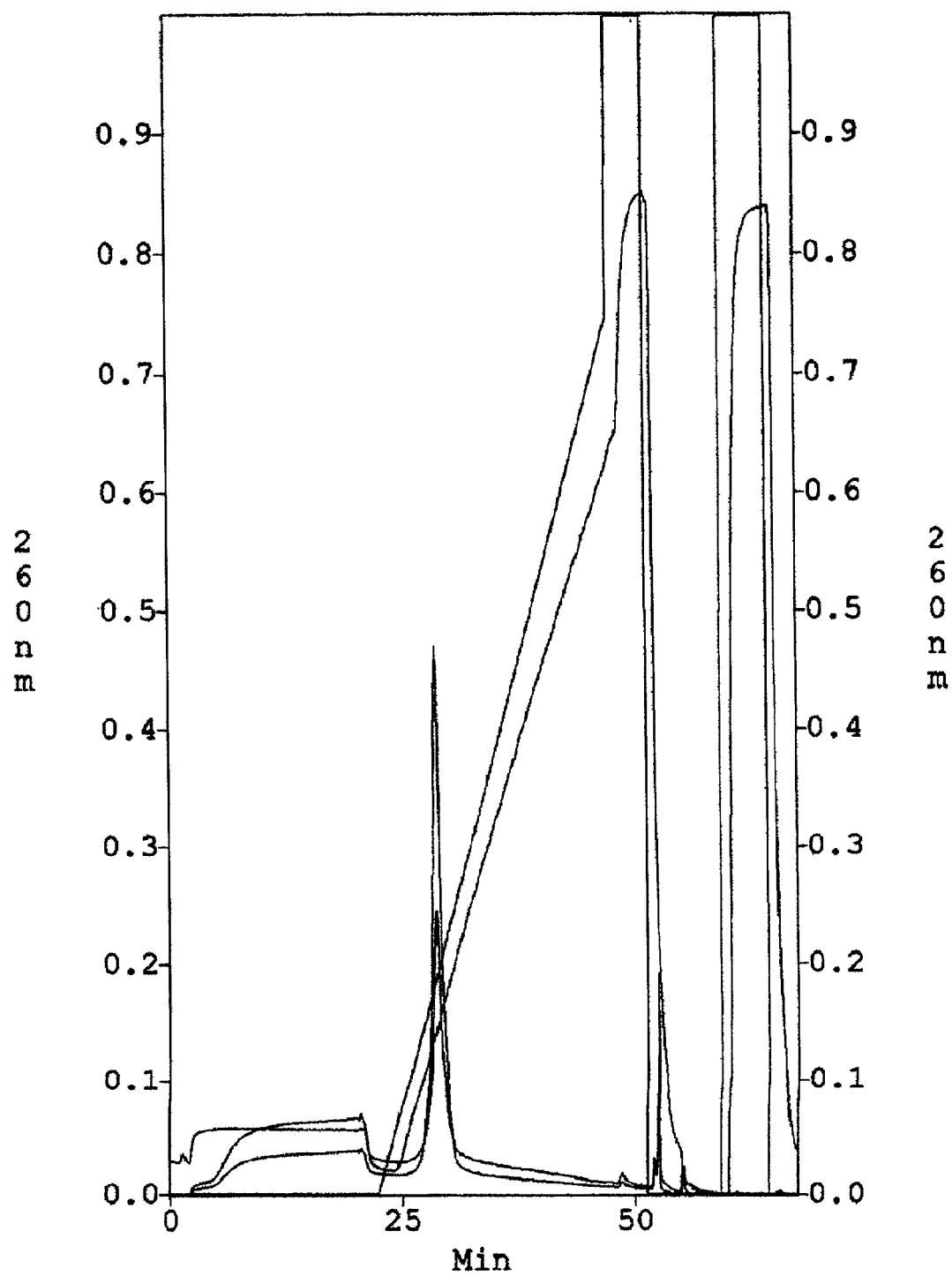
Figure 16G:
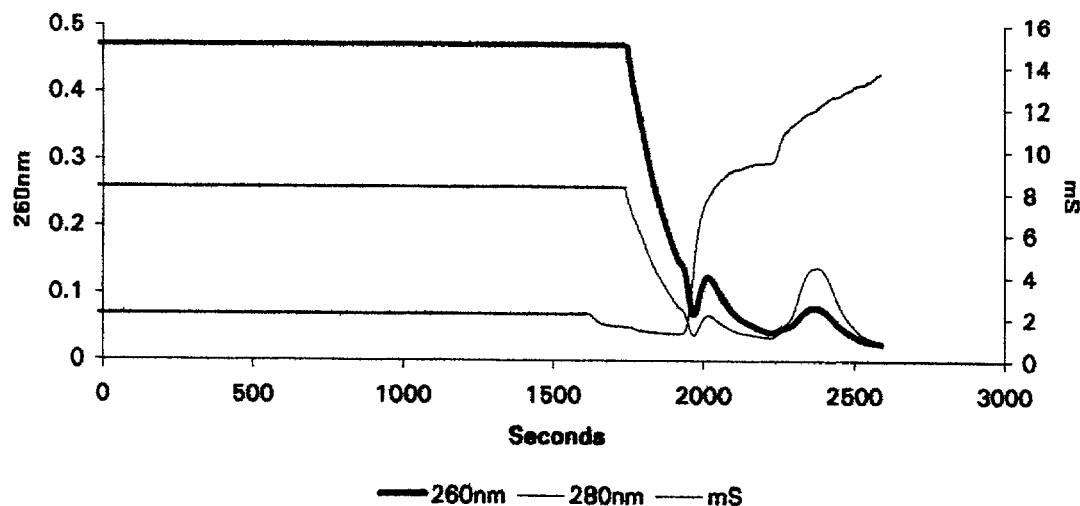
Figure 16H:
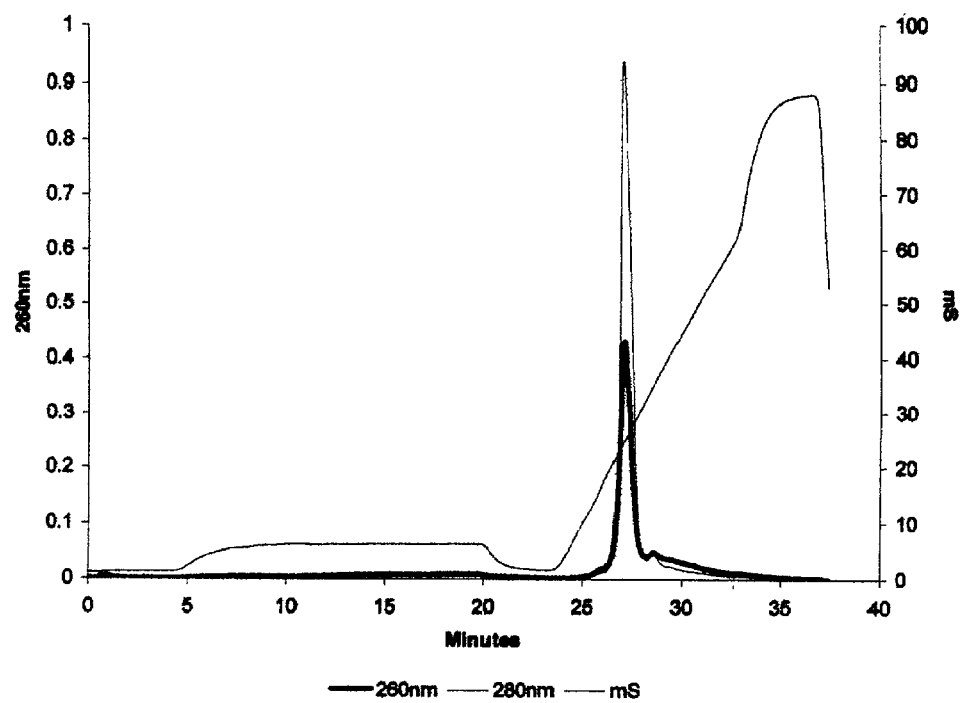
Figure 16I:
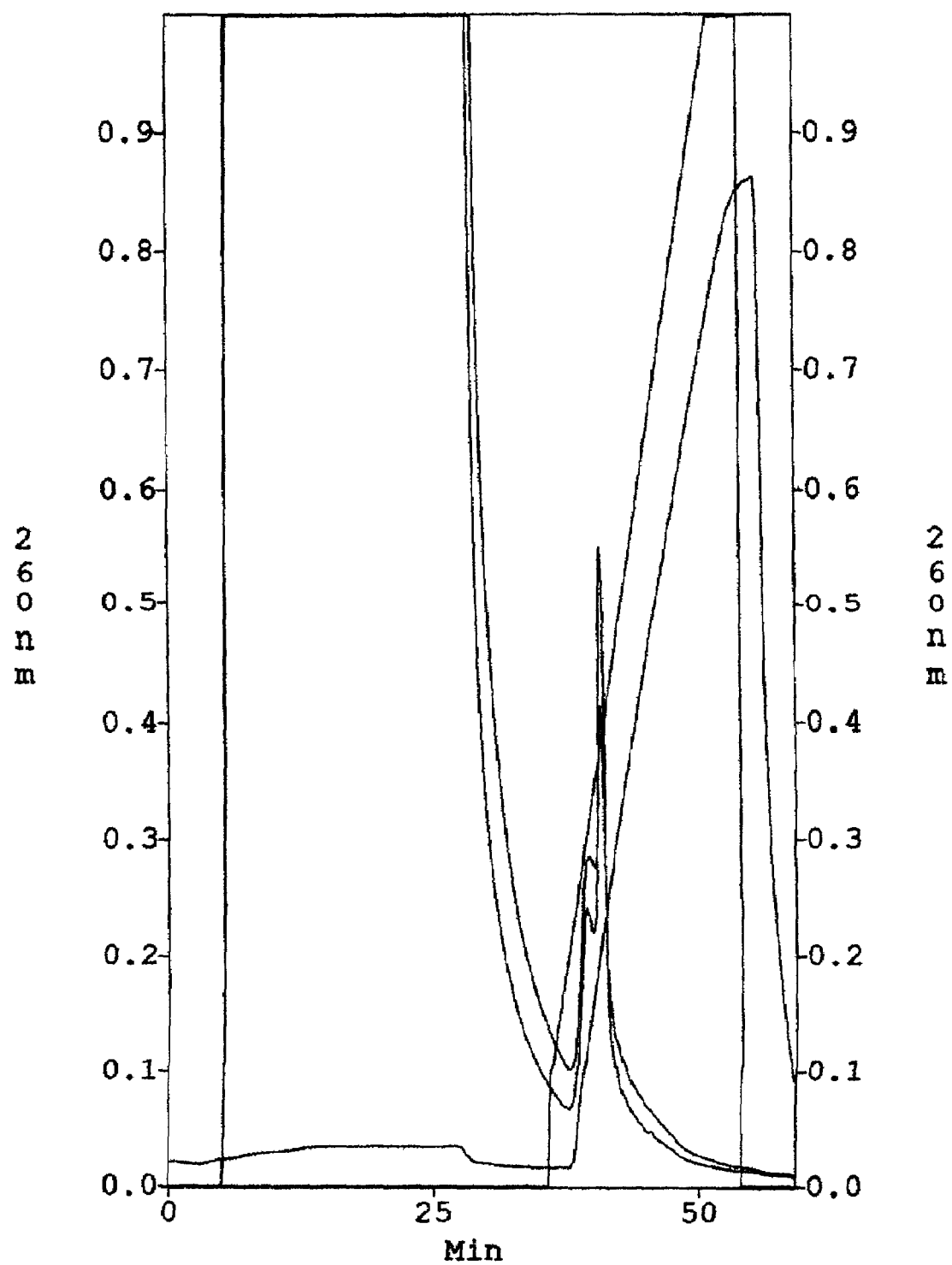
Figure 16J:
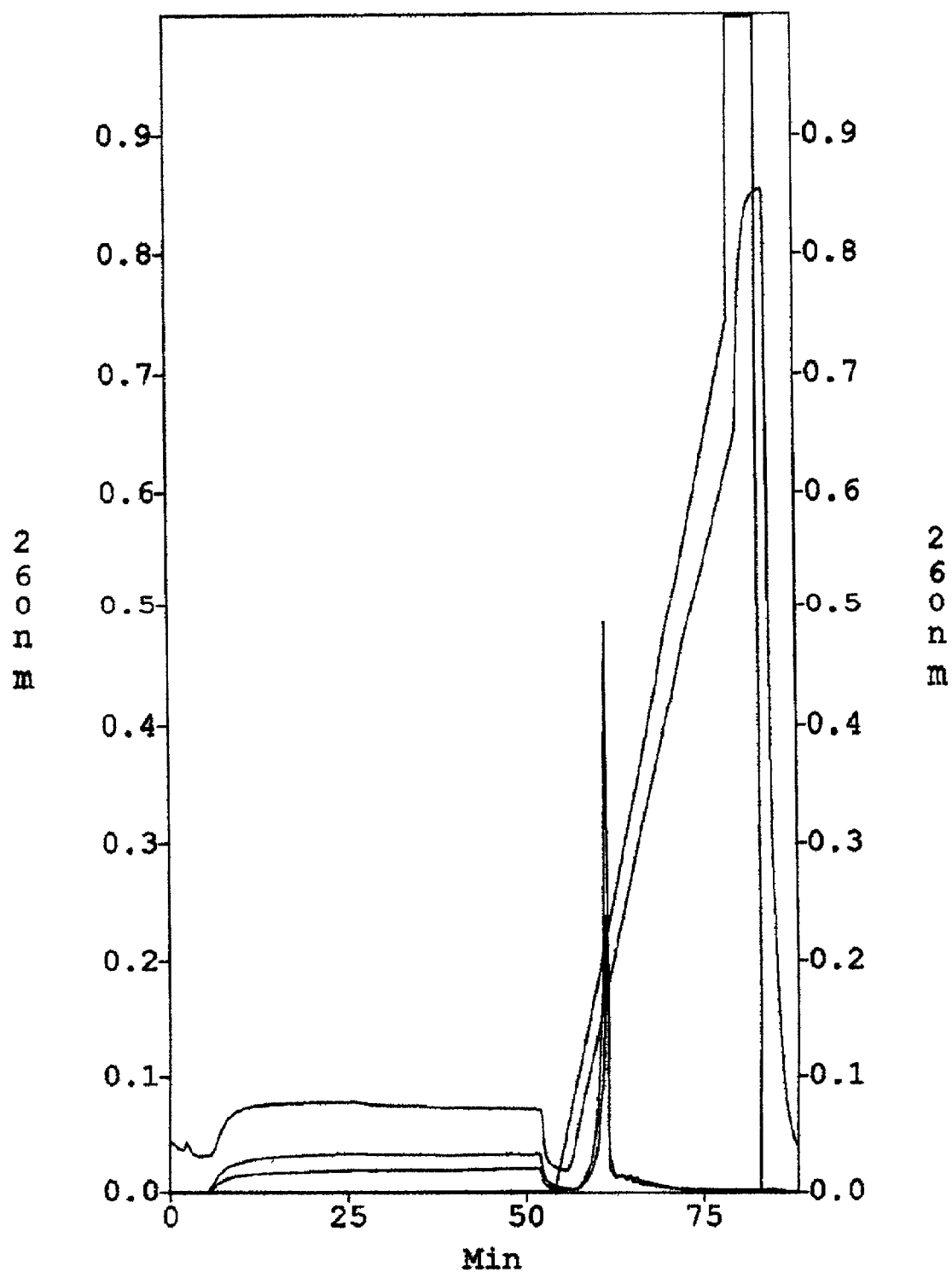
Figure 17A:
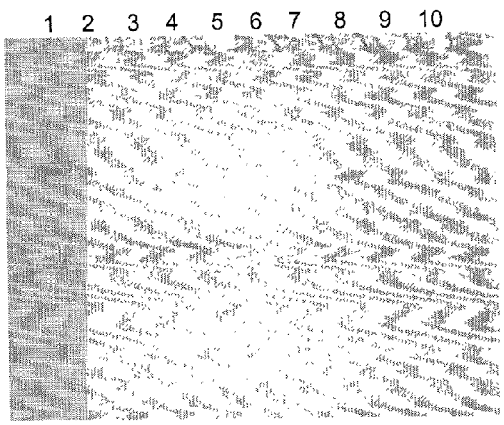
FIG. 17. SDS-PAGE (A) and Western blots of purified LcA constructs using rabbit peptide sera against LcA (B), LcA+Belt (C) and LcA+Hn (D). Lanes from all figures are identical. Lane 1, Novex See Blue prestained molecular weight markers; Lane 2, purified BoNt-A; Lane 3, LcA-HIS; Lane 4, LcA-phosphate buffer; Lane 5, LcA-NaAcetate buffer; Lane 6, LcA+Belt; Lane 7, LcA+Hn, nicked; Lane 8, LcA+Hn, un-nicked; Lane 9, negative control pET24a construct, no insert; Lane 10, LcB.
Figure 17B:
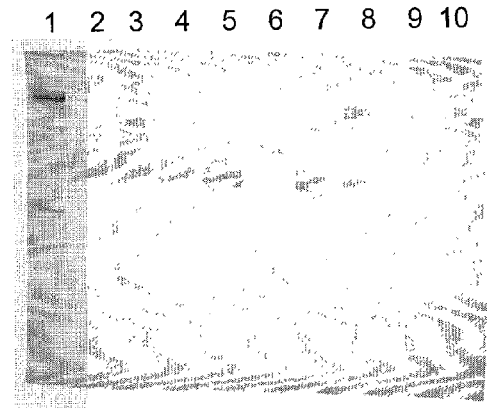
Figure 17C:
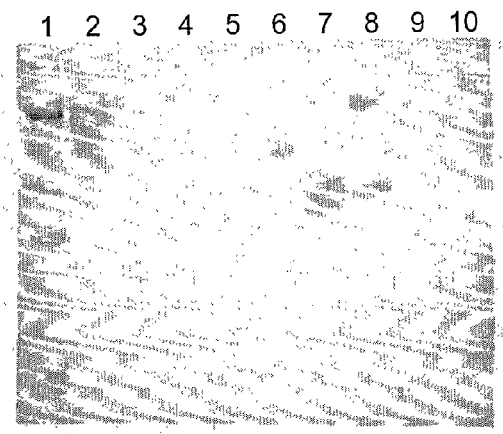
Figure 17D:

The material was reloaded onto the Mono S column for further purification. The larger, non-truncated, LcA eluted as a single peak at 12 mS (FIG. 16B). SDS-Page and western blot analysis showed only a single band at 51 k-Da (FIGS. 17A and 17B). The product was judged to be 98% pure after the final step and a protein determination determined the overall yield was 0.53 mg purified Lc per gram wet cells obtainable from our protocol.

The LcA+Belt eluted from the first column purification was approximately 85% pure, with a protein concentration of 0.454 mg/ml, in a total of 12 ml (FIG. 2C). After purification on the second column, a 4 ml pooled peak (FIG. 16D) had a concentration of 0.226 mg/ml, with 98% purity, producing a single band as observed by Western analysis (FIG. 17A and 17C). The overall yield was 0.347 mg/gm wet cells.

The LcA+Hn eluted from the first column purification was approximately 80% pure, with a protein concentration of 0.816 mg/ml, in a total of 12 ml (FIG. 16D). After purification on the second column, a 4 ml pooled peak (FIG. 16E) had a concentration of 0.401 mg/ml, with 98% purity, forming a single band, while the nicked form of the construct produced two bands (FIGS. 17A through 17D) corresponding to the Hn and Lc. The overall yield was 0.617 mg/gm wet cells.

Example 25

Assay for Cleavage of SNAP-25 Peptide

A 17-residue C-terminal peptide of SNAP-25 (acetyl-SNKTRIDEANQRATKML-amide) (SEQ ID NO:2) shown to be the minimum length required for optimal BoNT/A proteolytic activity (Schmidt and Bostian, 1997) was used as the substrate in a cleavage assay as described previously (Ashraf Ahmed et al.). Briefly, a 0.3 ml mixture containing 0.7–1.0 mM of the substrate peptide, 0.25 mM $ZnCl_2$, 5.0 mM DTT, 50 mM Na-HEPES buffer (pH=7.4) and purified LC (adjusted to produce 10–30% final cleavage) was incubated at 37° C. for 15–180 minutes. The reaction was stopped with 0.09 ml of 0.7% trifluoroacetic acid. Quantitation of cleaved and uncleaved peptide was done by reverse-phase HPLC separation and the fraction of the peptide proteolyzed was calculated by dividing the combined areas of the two cleaved peaks by the sum of the two product and uncleaved substrate peaks.

Catalytic Activity of the Expressed Constucts

Incubation of the 17-mer synthetic peptide representing residues 187–203 of SNAP-25 with the purified Lc at 37° C. generates only two peptides cleaving between residues 197 (glutamine) and 198 (arginine). No other peptide fragments were generated by prolonged incubation, indicating that any contaminants in the Lc preparation lacked proteolytic activity. FPLC purification run #71, which was the complete Lc, resulted in a specific activity of 2.36 μmol/min/mg of Lc. Native BoNT/A in previous assays with the SNAP-25 synthetic peptide had a specific activity of 0.241 μmol/min/mg (Schmidt and Bostian). Thus, the purified Lc produced had a specific activity increased by approximately 10-fold. Run #32 was the Lc+belt, and had an activity of 0.08 μmol/min/mg.

Example 26

Determination of the Length of the Purified Whole and Truncated Lc

HPLC-purified samples were mixed with sinapinic acid and deposited on a stainless steel target. Mass spectra were acquired with a Perseptive Biosystems Voyager DE MALDI-TOF system. Data were obtained in delayed extration mode (750 ns delay) with a 337 nm nitrogen laser (3 ns wide pulse), using an acquisition rate of 2 GHz, 50,000 channels, an accelerating voltage of 25000, 93% grid voltage, and a 0.3% guide wire voltage. Typically, 128 scans were averaged. The mass spectrometer was externally calibrated with myoglobin and bovine serum albumin.

The amino-terminal sequence of the expressed Lc was determined by automated Edman degradation performed on an Applied Biosystems Procise Sequencer (Applied Biosystems, Foster City, Calif.) in the 0–20 picomole detection range.

Determination of the Cleavage Point for Purified Lc

Purified Lc kept at −20° C. in purification buffer with 2 mM EDTA had no observable cleavage or truncation products. When the same product was placed at 30° C. for 1 hour, the truncated Lc seen after the first cation exchange column passage was observed. In a mass spectrum for cleaved BoNT/A Lc, the ion at mlz 49039.0 corresponds to the singly-charged molecule, whereas ions at m/z 24,556.9, and 98,280 correspond to doubly-charged and dimer species, respectively. The verified amino terminus for the Lc was VQFVNKQFNY (residues 2 to 11 of SEQ ID NO:5), with the terminal methione removed, resulting in a peptide of 448 residues. The observed principal mass of 49,039 is approximately 2279 daltons less than the calculated mass for type A Lc, which represents a loss of 2–22 amino acids. Since the amino terminus specific antibody still reacts with the truncated molecule, cleavage occurred near the C terminus of the molecule. Because of mass uncertainty with MALDI-TOFMS (0.05% maximum mass accuracy for this instrument), it was not possible to positively identify the site of cleavage. Nevertheless, it was determined that cleavage occurred at either $Y_{426}$, $K_{427}$, $L_{428}$. The most probable site of cleavage was between $K_{427}$ and $L_{428}$. Calculated mass for that product was 48,999, a difference of 40 daltons, which represents the best match to the observed ion and a mass accuracy to within 0.08%.

Addition of $MgCl_2$ to 125 mM and incubation for 1 hour at 30° C. resulted in two cleavage products after the Lc had lost the carboxy terminal residues. Amino terminus sequencing showed the cleavage to be between two tyrosines, $Y_{250}$ and $Y_{251}$.

Example 27

Phosphorylation of Purified Lc

Phosphorylation was at 30° C. for 1 to 24 hours in a final reaction volume of 40 μL with 30 units c-src kinase. Non-phosphorylated samples were those in which enzyme b was omitted. The amount of Lc in the reaction was from 6.25 nM to 1.25 nM. The 4× buffer used for the reaction consisted of 100 mM Tris-HCI, pH 7.2, 125 mM MgClz, 25 mM $MnCl_2$, 2 mM EGTA, and 2 mM DTT. ATP was at either 500 μM or 1 mM, with [$\gamma$-$^{32}$P]ATP added to a final concentration of 1 μCi/ul. In some cases, substrate peptide (KVEKIGEGTGV-VYK; SEQ ID NO:3) at 93 μM was substituted for the Lc to act as a control. Reactions were stopped by freezing at −20° C. Phosphorylated samples were run on SDS-PAGE gels, and either blotted and bands visualized with an antibody specific to phosphorylated tyrosine or the amino terminus of the Lc, or they were stained with Coomasie Blue, destained, dried and exposed to Kodak BioMax Light film.

Phosphorylation of Lc

Purified Lc that was tyrosine phosphorylated resisted cleavage at the $Y_{250}$–$Y_{251}$ site. During the initial 1 hour period of phosphorylation, the characteristic cleavage products were observed, but did not substantially increase over a 24 hour period of time. A possible explanation would be that phosphorylated Lc molecules were protected from cleavage, but not all of them could be modified prior to concurrent proteolysis. An identical reaction mixture lacking the enzyme showed rapid cleavage of the Lc, with very little remaining by 4 hours, and undetectable by 8 hours. A monoclonal antibody to phosphorylated tyrosine reacted to full length, src phosphorylated Lc, but not to either of the cleavage products in the phosphorylation reaction, even though cleavage products were clearly visible by SDS-PAGE at all time points. The reaction lacking the enzyme showed no phosphorylated tyrosine bands of any size. Antibody to the amino terminus of the Lc reacted to the full length and larger of the cleavage products, plus three additional bands of between 60 and 75 kDa. These additional bands above the Lc were observed by SDS-PAGE for all the samples and appear to be SDS-resistant complexes of either the Lc or amino terminus fragment with other fragments. Autoradiographs of the phosphorylated and unphosphorylated (lacking enzyme) Lc show incorporation of [$\gamma$-$^{32}$P]ATP in the src phosphorylated full length Lc at 1 hour, with none observed in smaller or larger fragments, nor in samples lacking the enzyme. At 24 hours, very faint bands corresponding to the cleavage products did appear. These could either have arisen from cleaved, phosphorylated, full length Lc, or they may have been phosphorylated after they became fragments.

Example 28

Immunity

Immunization of mice with the purified forms of the LcA, LcA+belt and LcA+Hn resulted in ELISA titers of between X and X for all construct forms. Protection was observed after challenge with $10^2$ to $10^3$ MLD$_{50}$ of purified Type A toxin. See Tables 6–8.

TABLE 6

Efficacy of Purified rBoNTA(LC + Belt) Solubly Expressed from *E. coli* to Elicit Protective Immunity in Mice

| Dosage[a,b] | Toxin Challenge (Survivors/Total) | | ELISA Titer |
|---|---|---|---|
| (μg) | $10^2$LD$_{50}$ | $10^3$LD$_{50}$ | (GMT)[c] |
| 5 | 10/10 | 10/10 | ND |
| 15 | 10/10 | 10/10 | ND |
| Controls | 0/10 | 0/10 | ND |

[a]Animals were vaccinated at 0, 2, and 4 weeks and challenged on week 6.
[b]Specific activity (i.e., proteolytic activity) of the rBoNTA(LC + belt) immunogen was not determined.
[c]Geometric mean of the ELISA titer to BoNTA neurotoxin (ND = not determined).

TABLE 7

Efficacy of Purified rBoNTA(LC + Hn) Solubly Expressed from *E. coli* to Elicit Protective Immunity in Mice

| Dosage[a,b] | Toxin Challenge (Survivors/Total) | | ELISA Titer |
|---|---|---|---|
| (μg) | $10^2$LD$_{50}$ | $10^3$LD$_{50}$ | (GMT)[c] |
| 5 | 5/9 | 1/9 | ND |
| 15 | 4/10 | 1/10 | ND |
| Controls | 0/10 | 0/10 | ND |

[a]Animals were vaccinated at 0, 2, and 4 weeks and challenged on week 6.
[b]Specific activity (i.e.. proteolytic activity) of the rBoNTA(LC − H$_n$) immunogen was not determined.
[c]Geometric mean of the ELISA titer to BoNTA neurotoxin (ND = not determined).

TABLE 8

Efficacy of Purified rBoNTA(LC) Solubly Expressed from *E. coli* to Elicit Protective Immunity in Mice

| Dosage[a,b] | Toxin Challenge (Survivors/Total) | | ELISA Titer |
|---|---|---|---|
| (μg) | $10^2$LD$_{50}$ | $10^3$LD$_{50}$ | (GMT)[c] |
| 5 | 9/10 | 10/10 | ND |
| 15 | 9/10 | 10/10 | ND |
| Controls | 0/10 | 0/10 | ND |

[a]Animals were vaccinated at 0, 2, and 4 weeks and challenged on week 6.
[b]Specific activity of the rBoNTB(LC) immunogen was 21 mmol/min/mg using 0.8–1.0 mM substrate (VAMP peptide, residues 54–94).
[c]Geometric mean of the ELISA titer to BoNTB neurotoxin (ND = not determined).

Example 29

Discussion

The system of expression of the invention for *botulinum* neurotoxin Hc (Byrne et al, 1998) and Lc fragments using an optimized synthetic gene, has previously shown success in achieving high levels of product. In an attempt to produce a molecule that more closely resembles the natural state of the toxin, a cloning and expression scheme that would give a large amount of correctly folded, untagged, Lc was initiated. The two basic strategies employed were to (1) express the Lc at a lower temperature, a classic method for ensuring proper folding, and (2) adding on portions of the rest of the neurotoxin polypeptide, mimicking the natural expression within the clostridial host. As expected, reducing the temperature for induction dramatically increased the solubility of the expressed product from 5.2% at 37° C. to 55.5% at 18° C. for the Lc. The slower rate of expression at the lower temperatures was compensated for by increasing the length of time for expression. This did not result in increased degradation of the product intracellularly, prior to harvest and purification. Addition of the belt and Hn portions of the toxin had no effect upon solubility of the expressed gene, although each was easily expressed at the lower temperature.

Although cloned and expressed Lc has been available for Lc study, it has been purified with either glutathione or his-tags (Zhou, et al, 1995; Li and Singh, 1999). Previous investigators have used native toxin (Lacy et al, 1998) for x-ray crystallography studies, and it was an object of the invention to produce Lc as close to the native product as possible, e.g., without tags or modifications. For this reason, traditional column chromatography methods were used instead of affinity columns. The calculated pI of the Lc of 8.13 suggested that the Lc would efficiently bind to a cation exchange column. Upon passage over an initial Mono S column, the product appeared relatively clean, although a second immunoreactive band immediately beneath the proper, calculated size for the Lc was noted. After passage over a second cationic exchange column, this band was not observed on Westerns.

Using the above methods of low temperature expression and cation exchange purification, a large quantity of Lc was acquired for assessment of catalytic activity. Activity of the purified Lc was calculated to be approximately 10-fold greater than that of the native toxin. Previous investigators have shown that the Lc must be activated by proteolytic cleavage of the Lc from the Hc (DasGupta and Dekleva, 1990), although the two halves must both be present for efficient intoxication of cells. It is interesting that the Lc with the belt attached lacked the high level of catalytic activity seen with the Lc by itself. Presumably, the belt is wrapped around the Lc, as is observed in x-ray crystallography studies (Lacy et al, 1998). As the entire translocation region is not there to occlude the active site, it may be that the belt in some manner is constricting the Lc, or a conformational change is prevented that is required for full activation. Comparison of the crystallography structure of Lc of the invention with and without the belt would be worth further study.

Two interesting and unexpected pieces of data came from expression of Lc without purification tags. The first was the truncation of the Lc from the carboxy terminus by 20 residues. A recent paper by Kadkhodayan et al, 2000, notes that this portion of the Lc is not required for full catalytic activity. The truncation is intriguing as it removes the Lc/Hc di-sulfide bond at a lysine proximal to the involved cysteine. The two other proteolytic cleavages known to occur at the carboxy terminus of the Lc are also at lysine residues (DasGupta and Dekleva, 1990). Lysine proteolysis is common, with ubiquitin, a lysine specific proteolysis factor found conjugated to cell receptors of eukaryotes being one of the most common routes (Doherty and Mayer, 1992). It has long been hypothesized that the di-sulfide bond holding the Lc and Hc together was reduced as the Lc was transported into the cell, freeing it from the receptor binding portion (de Paiva et al, 1993). Although the ten residue portion flanked by lysine residues seems to be removed during activation "nicking" of the polypeptide, the cysteine residue was assumed to remain as part of the Lc. Work with native toxin and cells has been initiated to determine if the natural state of the toxin inside cells is one lacking the terminal 20 residues and cysteine.

Example 30

Expression of BoNT LC

Reagents: Terrific Broth (Difco): 48 gm/liter with 4 ml of non-animal glycerol; autoclave 15 minutes. Store refrigerated. Kanamycin: stock solution is 50 mg/ml in distilled water, filter sterilized, store in aliquots at −20° C. Chloramphenicol: stock solution is 50 mg/ml in ethanol, filter sterilized, store in aliquots at −20° C. Add antibiotics to media just prior to use.

Expression of the Lc and Lc with Hc (translocation region) was performed for even numbered SEQ ID NOS: 20–44. Expression was essentially the same for all constructs within the given parameters.

Cultures of BL21(DE3) cells were grown in Terrific Broth (TB) plus 50 μg/mL kanamycin. Cultures of BL21(DE3) Codon Plus cells were grown in TB plus 50 μg/mL kanamycin and 50 μg/mL chloramphenicol. Cultures grown overnight at 37° C. while shaking at about 200 to about 250 rpm were diluted 1:20 with fresh antibiotic-containing media. Diluted cultures were returned to overnight growth conditions (37° C., shaking at 200–250 rpm) for 1¼ to 2½ hours. An optical density measurement was taken while the cultures were placed on ice for 5 minutes. Preferably, the $OD_{600}$ is between about 0.4 and about 0.6. The incubation time may be extended and/or fresh antibiotic-containing media may be added if the $OD_{600}$ is lower than 0.4 or higher than 0.6.

Next, sufficient IPTG was added to each chilled culture to make the concentration about 1 mM. IPTG-containing cultures were incubated about 24 to about 26 hours at 18° C. and shaking at about 200 to about 250 rpm. An optical density measurement was taken at the end of this incubation. Preferably, the $OD_{600}$ is between about 1.7 and about 2.1.

Cultures that satisfied this criteria were centrifuged at about 3000 rpm for about 20 minutes to obtain a cell paste for purification. The cell paste may be stored at −20° C. until ready for use.

Aliquots of 1 mL each were pelleted in a microfuge, resuspended in 1 mL of sonication buffer, and sonicated 12×30 seconds on ice over 12 minutes. Sonicated cells were microfuged for 10 minutes. The supernatant was aspirated and retained as the soluble fraction. 1 mL of 6M urea was added to each pellet and retained as the insoluble fraction. Appropriate amounts run on by SDS-PAGE should show approximately 50% soluble, 50% insoluble, at about 51 kDa. A western with rabbit anti-Lc sera will be at the same location.

Purification of BoNT LC

Cell paste was resuspended at 1 g/20 mL sonication buffer, sonicated 10×30 seconds on, 30 seconds off, on ice. Insoluble material and debris was pelleted by centrifuging for 10 minutes at 12,000 rpm (e.g. in a microfuge), decanting solute, and repeating one time in a fresh tube. The supernatant was decanted into a fresh tube. An equal volume of equilibration buffer may be optionally added to the supernatant to facilitate cation exchange chromatography, e.g., flow. For example, such dilution facilitates column loading and washing when using a Source S resin from Pharmacia whereas such dilution is unnecessary when using a Poros cationic resin. Filter sterilize the supernatant with 0.45 μm filters.

Run #1: A column (100 mm) was equilibrated with equilibration buffer, 2 minutes, 2.5 to 3 ml/min (same rate through out run). Cell paste (20–40 mL per run) was manually loaded. The column was washed for 3 minutes with equilibration buffer. Using gradient buffer, a 0 to 70% gradient was run over 8 minutes. For some cell lysates, a 5% NaCl (5 mS) 5 minutes step was performed. For example, where a Source S resin was used, no salt wash was was performed, but where a Poros resin was used, this salt wash was performed to elute contaminating proteins. Cell protein was collected at between 10 and 22 mS. Fractions (1 mL) were collected through out the gradient. The desired protein will elute at between 10 and 22 mS, depending upon the expression product used.

Run #2: The peak fractions from run #1 were pooled. Equilibration buffer was added to pooled fractions, at a 3:1 ratio. The column was equilibrated with equilibration buffer for 2 minutes, at 2.5 to 3 ml/min (same rate through out run). The run #1 pool was loaded onto the column; washed 2 minutes with equilibration buffer. Using gradient buffer, a 0 to 75% gradient was run over 15 minutes. Fractions (1 mL)

were collected and peak fractions were pooled. Aliquots of the pooled fractions were stored in plastic vials at −20° C.

A portion of the purified protein was used to measure the $A_{260/278}$. The ratio may be used as a measure of the presence of DNA and the $A_{280}$ to quantitate the protein by using the calculated molar extinction coefficient and molecular weight.

A cleaning procedure must be done on the column between each run. Run 1 M NaCl through column at 3 ml/min for 5 minutes. Run 20 mM NaOH through the column at 1 ml/min for 10 minutes. Run 70% ETOH through the column at 1 ml/min for 30 minutes. Run 1 M NaCl through it at 1 ml/min for 15 minutes. Re-equilibrate the column to the proper pH with a low salt buffer.

Buffers

A combination of sonication buffers, equilibration buffers and gradient buffers is used for each cell lysate. Sonication buffers are always chosen to be 0.4 pH below the equilibration buffer. Gradient buffers are the same as equilibration buffers except for addition of 1 M NaCl.

Gradient buffer A: 55 mM Na mono-phosphate, 2 mM EDTA, 1 M NaCl, in milliQ water; pH to 5.8; filter. Gradient buffer B: 20 mM NaAcetate, 1 M NaCl, in milliQ water, pH to 5.4, filter. Gradient buffer C1: 20 mM NaAcetate, 1 M NaCl, in milliQ water, pH to 4.8, filter. Gradient buffer C2: 20 mM NaAcetate, 2 mM EDTA, 1 M NaCl, in milliQ water, pH to 5.4, filter. Gradient buffer D: 20 mM NaAcetate, 2 mM EDTA, 1 M NaCl, in milliQ water, pH to 4.8, filter.

Results

Expression and purification of BoNT/A LC according to this method yielded protein with a specific activity (SNAP-25 assay) that was about 10-fold higher than when BoNT/A LC was purified from inclusion bodies (Ahmed and Smith (2000) J. Prot Chem. 19, 475–487).

REFERENCES

The references cited throughout this application and listed below are incorporated herein in their entirety by reference.

Adler, M., Dinterman, R. E., and Wannemacher, R. W. (1997). *Toxicon* 35, 1089–1110.

Ahmed, S. A. and Claiborne, A. (1992). *J. Biol. Chem.* 267, 3822–3840.

Ahmed, S. A. and Smith, L. A. (2000). *J. Protein Chem.* 19, 475–487.

Ahmed, S. A., Byrne, M. P., Jensen, M., Hines, H. B., Brueggemann, E., and Smith, L. A. (2001). *J. Protein Chem.* 20, 221–231.

Ahmed, S. A., Fairwell, T., Dunn, S., Kirschner, K., and Miles, E. W. (1986). *Biochemistry* 25, 3118–3124.

Alderton, J. M., Ahmed, S. A., Smith, L. A., and Steinhardt, R. A. (2000). *Cell. Calcium* 28, 161–169.

Andersson, S. G., and Kurland, C. G. (1990). *Microbial. Rev.* 54, 198–210.

Auld, D. S. (1995). *Meth. EnUmol.* 248, 228–242.

Bi, G. Q., Alderton, J. M., and Steinhardt, R. A. (1995). *J. Cell Biol.* 131, 1747–1758.

Bittner, M. A., DasGupta, B. R., and Holz, R. W. (1989). *J. Biol. Chem.* 264, 10354–10360.

Black, J. D., and Dolly, J. O. (1986). *J. Cell Biol.* 103, 535–544.

Blasi, J., Chapman, E. R., Link, E., Binz, T., Yamasaki, S., De Camilli, P., Sudhof, T. C. Niemann, H., and Jahn, R. (1993). *Nature* 365, 160–163.

Cai, S., Sarkar, H. K., and Singh, B. R. (1999). *Biochemistry* 38, 6903–6910.

Cardoso F, Jankivic J (1995). Clinical use of *botulinum* neurotoxins. In *Current Topics in Microbiology and Immunology* (Capron A et al., eds.), Springer-Verlag, Germany, pp. 123–141.

Chen, F., Kuziemko, G. M., Amersdorfer, P., Wong, C., Marks, J. D., and Stevens, R. C. (1997). *Infect. Immun.* 65, 1626–1630.

Claiborne, A., Yeh, J. I., Mallett, T. C., Luba, J., Crane, E. J., 3rd, Charrier, V., and Parsonage, D. (1999). *Biochemistry* 38, 15407–15416.

Creighton, T. E. (1984). *Proteins, Structures and Molecular Properties*, Freeman, New York.

Dalbey, R. E. and Kahn, A. (2000). *Annu. Rev. Cell Dev. Biol.* 16, 51–87.

DasGupta, B. R., and Dekleva, M. L. (1990). *Biochimie* 72, 661–664.

DasGupta, B. R., and Foley, J., Jr. (1989). *Biochimie* 71, 1193–1200.

Dekleva, M. L. and DasGupta, B. R. (1990). *J. Bacteriol.* 172, 2498–2503.

de Paiva, A., Poulain, B., Lawrence, G. W., Shone, C. C., Tauc, L., and Dolly, J. O. (1993). *J. Biol. Chem.* 268, 20838–20844.

Dertzbaugh, M. T., and West, M. W. (1996). *Vaccine* 14, 1538–1544.

Ettinger, R. A., Liu, A. W., Nepom, G. T., and Kwok, W. W. (2000). *J. Immunol* 165, 3232–3238.

Foran, P., Shone, C. C., and Dolly, J. O. (1994). *Biochemistry* 33, 15365–15374.

Foran, P., Lawrence, G. W., Shone, C. C., Foster, K. A., and Dolly, J. O. (1996). *Biochemistry* 35, 2630–2636.

Fu, F. N., Lomneth, R. B., Cai, S., and Singh, B. R. (1998). *Biochemistry* 37, 5267–5278.

Kadkhodayan, S., Knapp, M. S., Schmidt, J. J., Fabes, S. E., Rupp, B., and Balhorn, R. (2000). *Protein Expr. Purif.* 19, 125–130.

Kiyatkin, N., Maksymowych, A. B., and Simpson, L. L. (1997). *Infect. Immun.* 65, 4586–4591.

Klatt, P., Schmidt, K., Lehner, D., Glatter, O., Bachinger, H. P., and Mayer, B. (1995). *EMBO J.* 14, 3687–3695.

Knapp, M., Segelke, B., Balhorn, R., and Rupp. B. (2000). The crystal structure of *botulinum* toxin A zinc protease domain. Presented at the 37th Annual Meeting of the Interagency *Botulinum* Research Coordinating Committee, Alisomar, Calif.

Kreiglstein, K. G., DasGupta, B. R., and Henschen, A. H. (1994). *J. Protein Chem.* 13, 49–57.

Kurazono, H. Mochida, S., Binz, T., Eisel, U., Quanz, M., Grebenstein, O., Wetnars, K., Poulain, B., Tauc, L., and Niemann, H. (1992). *J. Biol. Chem.* 267, 14721–14729.

Lacy, D. B., and Stevens, R. C. (1999). *J. Mol. Biol.* 291, 1091–1104.

Lacy, D. B., Tepp, W., Cohen, A. C., DasGupta, B. R., and Stevens, R. C. (1998). *Nature Struct. Biol.* 5, 898–902.

Laemmli, U. K. (1970). *Nature* 227, 680–685.

Lebeda, F. J., and Olson, M. A. (1994). *Proteins* 20, 293–300.

Li, L., and Singh, B. R. (1999). *Protein Expr. Purif.* 17, 339–344.

Li, L. and Singh, B. R. (2000). *Biochemistry* 39, 10581–10586.

Li, Y., Foran. P., Fairweather, N. F., de Paiva, A., Weller, U., Dougan, G., and Dolly, J. O. (1994). *Biochemistry* 33, 7014–7020.

Maisey, E. A., Wadsworth, J. D., Poulain, B., Shone, C. C., Melling. J. Gibbs, P., Tauc, L., and Dolly, J. O. (1988). *Eur. J. Biochem.* 177, 683–691.

Makoff, A. J., Oxer, M. D., Romanos, M. A., Fairweather, N. F., and Ballantine, S. (1989). *Nucleic Acids Res.* 17, 10191–10202.

Montal, M. S., Blewitt, R., Tomich, J. M., and Mortal, M. (1992). *FEBS Lett.* 313, 12–18.

Montecucco, C., and Schiavo, G. (1994). *Mol. Microbiol* 13, 1–8.

Montecucco, C., and Schiavo, G. (1995). *Q. Rev. Biophys.* 28, 423–472.

Nowakowski, J. L., Courtney, B. C., Bing, Q. A., and Adler, M. (1998). *J. Protein Chem.* 17, 453–462.

Pace, C. N., Vajdos, F., Fee, L., Grimsley, G., and Gray, T. (1995). *Protein Sci.* 4, 2411–2423.

Rossetto, O., Schiavo, G., Montecucco, C., Poulain, B., Deloye, F. Lozzi, L., and Shone, C. C. (1994). *Nature* 372, 415–416.

Schiavo, G., Rossetto, O., Catsicas, S., Polverino de Laureto, P., DasGupta, B. R., Benfenati, F., and Montecucco, C. (1993). *J. Biol. Chem* 268, 23784–23787.

Schiavo, G., Malizio, C., Trimble, W. S., Polverino de Laureto, P. Milan, G., Sugiyama, H., Johnson, E. A., and Montecucco, C. (1994). *J. Biol. Chem.* 269, 20213–20216.

Schiavo, G. Rossetto, Tonello, F., and Montecucco, C. (1995). Intracellular targets and metalloprotease activity of tetanus and *botulinum* neurotoxins. In *Clostridial Neurotoxins: The Molecular Pathogenesis of Tetanus and Botulism* (Montecucco, C., ed.), Springer, New York, pp. 257–273.

Schmidt, J. J., and Bostian. K. A. (1995). *J. Protein Chem.* 14, 703–708.

Schmidt, J. J., and Bostian. K. A. (1997). *J. Protein Chem.* 16, 19–26.

Schmidt, J. J., Stafford R G, Millard C B (2001). *Analytical Biochemistry* 296, 130–137.

Shone, C. C., and Roberts, A. K. (1994). *Eur. J. Biochem.* 225, 263–270.

Shone, C. C., and Tranter, H. S. (1995). *Curr. Top. Microbiol. Immunol.* 195, 143–160.

Shone, C. C., Quinn, C. P., Wait, R., Hallis, B., Fooks, S. G., and Hambleton, P. (1993). *Eur. J. Biochem.* 217, 965–971.

Schagger, H. and von Jagow, G. (1987). *Anal. Biochem.* 166, 368–379.

Schmidt, J. J., Stafford, R. G., and Bostian, K. A. (1998). *FEBS Lett.* 435, 61–64.

Sheridan, R. E., Deshpande, S. S., Nicholson, J. D., and Adler, M. (1997). *Toxicon* 35, 1439–1451.

Simpson, L. L., Coffield, J. A., and Bakry, N. (1993). *J. Pharmacol. Exp. Ther.* 267, 720–727.

Smith, L. A. (1998). *Toxicon* 36, 1539–1548.

Steinhardt, R. A., Bi, G., and Alderton, J. M. (1994). *Science* 263, 390–393.

Strasser, A., O'Connor, L., and Dixit, V. M. (2000). *Annu. Rev. Biochem* 69, 217–245.

Syuto, B., and Kubo, S. (1981). *J. Biol. Chem.* 256, 3712–3717.

Thompson, D. E., Brehm, J. K., Oultram, J. D., Swinfield, T. J., Shone, C. C. Atkinson, T., Melling, J., and Minton, N. P. (1990). *Eur. J. Biochem.* 189, 73–81.

Washbourne, P., Pellizzari, R. Baldini, G., Wilson, M. C., and Montecucco, C. (1997). *FEBS Lett.* 418, 1–5.

Winkler, H. H., and Wood, D. O. (1988). *Biochimie* 70, 977–986.

Zhou, L., de Paiva, A. Liu, D., Aoki, R., and Dolly, J. O. (1995). *Biochemistry* 34, 15175–15181.

---

We claim:

1. A method for producing a *botulinum* neurotoxin light chain comprising:
   culturing, at a temperature below 30° C., a host cell comprising an expression control sequence operably linked to a nucleic acid sequence encoding the *botulinum* neurotoxin light chain;
   expressing the *botulinum* neurotoxin light chain;
   obtaining a protein fraction from the cultured host cell; and
   isolating the *botulinum* neurotoxin light chain from the protein fraction, wherein more than 100 mg of *botulinum* neurotoxin light chain is obtained per liter of culture.

2. The method of claim 1 wherein the nucleic acid encodes a polypeptide having the amino acid sequence selected from the group consisting of SEQ ID NO:7, SEQ ID NO:9, SEQ ID NO:11, SEQ ID NO:13, SEQ ID NO:15, SEQ ID NO:17, SEQ ID NO:23, SEQ ID NO:27, SEQ ID NO:31, SEQ ID NO:35, SEQ ID NO:39, and SEQ ID NO:43, and wherein the nucleic acid has a total A+T content that is less than about 70%.

3. The method of claim 1 wherein the host cell is *Pichia pastoris*.

4. The method of claim 1 wherein the host cell is *Escherichia coli*.

5. The method of claim 1 wherein more than about 500 mg of purified *botulinum* neurotoxin light chain is obtained per liter of culture.

6. The method of claim 1 wherein about 1 gram of purified *botulinum* neurotoxin light chain is obtained per liter of culture.

7. The method of claim 1 wherein the *botulinum* neurotoxin light chain is catalytically active.

8. The method of claim 1 wherein the nucleic acid sequence has the sequence of nucleotides 9–1337 of SEQ ID NO:4.

9. The method of claim 1 wherein the nucleic acid sequence encodes a *botulinum* neurotoxin light chain serotype A.

10. The method of claim 1 wherein the nucleic acid encodes a *botulinum* neurotoxin light chain selected from the group consisting of *botulinum* neurotoxin light chain serotype B, *botulinum* neurotoxin light chan serotype C1, *botuylinum* neurotoxin light chain serotype D, *botulinum* neurotoxin light chain serotype E, *botulinum* neurotoxin light chain serotype F, and *botulinum* neurotoxin light chain serotype G.

11. The method of claim 1 wherein the nucleic acid has a total A+T content that is less than about 70%.

12. The method of claim 1 wherein the nucleic acid encodes a polypeptide having the amino acid sequence selected from the group consisting of SEQ ID NO:47 and SEQ ID NO:21.

13. The method of claim 1 wherein the A+T content of any 50 consecutive nucleotides of the nucleic acid is less than about 75%.

14. The method of claim 1 wherein the A+T content of any 50 consecutive nucleotides of the nucleic acid is less than about 75%.

15. The method of claim 1 wherein the nucleic acid has a sequence selected from the group consisting of SEQ ID NOS:6, 8, 10, 12, 14, 16, 22, 26, 30, 34, 38, and 42.

16. The method of claim 1 wherein the *botulinum* neurotoxin light chain is non-toxic.

* * * * *